US008722887B2

(12) United States Patent
Van Loevezijn et al.

(10) Patent No.: US 8,722,887 B2
(45) Date of Patent: *May 13, 2014

(54) SULFONYLPYRAZOLE AND SULFONYLPYRAZOLINE CARBOXAMIDINE DERIVATIVES AS 5-HT$_6$ ANTAGONISTS

(75) Inventors: Arnold Van Loevezijn, Weesp (NL);
Wouter I. Iwema Bakker, Weesp (NL);
Hiskias G. Keizer, Weesp (NL); Jan Zorgdrager, Weesp (NL); Martina A. W. Van Der Neut, Weesp (NL);
Cornelis G. Kruse, Weesp (NL)

(73) Assignee: Abbvie Bahamas, Ltd., Nassau (BS)

( * ) Notice: Subject to any disclaimer, the term of this patent is extended or adjusted under 35 U.S.C. 154(b) by 623 days.

This patent is subject to a terminal disclaimer.

(21) Appl. No.: 12/706,279

(22) Filed: Feb. 16, 2010

(65) Prior Publication Data
US 2010/0145042 A1 Jun. 10, 2010

Related U.S. Application Data

(62) Division of application No. 11/859,323, filed on Sep. 21, 2007, now Pat. No. 7,728,018.

(60) Provisional application No. 60/846,406, filed on Sep. 22, 2006, provisional application No. 60/902,865, filed on Feb. 23, 2007.

(51) Int. Cl.
| C07D 231/06 | (2006.01) |
| C07D 401/12 | (2006.01) |
| C07D 403/12 | (2006.01) |
| C07D 413/12 | (2006.01) |
| C07D 417/12 | (2006.01) |
| C07D 471/10 | (2006.01) |

(52) U.S. Cl.
USPC .......... 546/20; 546/119; 546/172; 546/211; 546/275.4; 548/126; 548/131; 548/154; 548/178; 548/186; 548/243; 548/312.4; 548/357.5; 548/360.1; 548/364.4; 548/379.4

(58) Field of Classification Search
None
See application file for complete search history.

(56) References Cited

U.S. PATENT DOCUMENTS

| 6,974,810 B2 | 12/2005 | Lange et al. |
| 2001/0053788 A1 | 12/2001 | Lange |

FOREIGN PATENT DOCUMENTS

| CN | 1529595 A | 9/2004 |
| EP | 2 069 310 B1 | 6/2009 |
| WO | WO 01/070700 * | 9/2001 | ........... C07D 231/06 |
| WO | WO 03/026647 A | 4/2003 |
| WO | WO 03/026648 A | 4/2003 |
| WO | WO 2007/020286 | 2/2007 |

OTHER PUBLICATIONS

Svetlik et al. J. Chem. Soc., Perkin Trans. 1, (2002), pp. 1260-1265.*
STN database entry for CAS RN 876508-69-9, indexed on Mar. 12, 2006, Accessed via STN Registry on Feb. 10, 2011.*
Bentley et al., "Investigation of stretching behavior induced by the selective 5-HT$_6$ Receptor Ro 4-6790, in rats," British Journal of Pharmacology (1999) 126, pp. 1537-1542.
Woolley et al, "A role for 5-ht$_6$ receptors in retention of spatial learning in the Morris water maze," Neuropharmacology 41 (2001) pp. 210-219.
Journal of Psychopharmacology, Supplement to vol. 11, No. 3, (1997) A64.
Damasio, Antonio R.; Alzheimer's Disease and Related Dementias, Cecil Textbook of Medicine, 20$^{th}$ Edition (1996), vol. 2, pp. 1992-1996.
FDA mulls drug to slow late-stage Alzheimer's [online], [retrieved on Sep. 23, 2003]. Retrieved from the Internet, URL: http://www.cnn.com/2003/HEALTH/conditions/09/24/alzheimers.drug.ap/indez.html, pp. 1 and 2.

(Continued)

Primary Examiner — Alicia L Otton
(74) Attorney, Agent, or Firm — Finnegan, Henderson, Farabow, Garrett & Dunner

(57) ABSTRACT

This invention concerns compounds of the general formula (1):

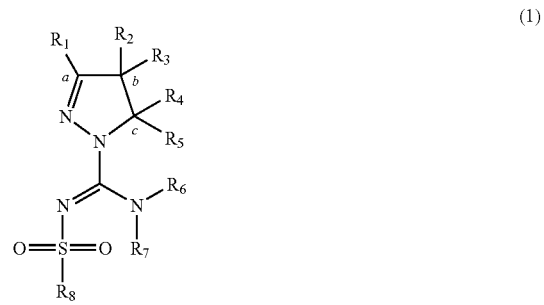

and derivatives thereof, which are antagonists of 5-HT$_6$ receptors, wherein the symbols have the meanings given in the description. The invention also concerns methods for the preparation of these compounds, to novel intermediates useful for their synthesis, and to uses of such compounds and compositions, particularly their use in administering them to patients to achieve a therapeutic effect in treating at least on disease or condition chosen from Parkinson's disease, Huntington's chorea, schizophrenia, anxiety, depression, manic depression, psychoses, epilepsy, obsessive compulsive disorders, mood disorders, migraine, Alzheimer's disease, age related cognitive decline, mild cognitive impairment, sleep disorders, eating disorders, anorexia, bulimia, binge eating disorders, panic attacks, akathisia, attention deficit hyperactivity disorder, attention deficit disorder, withdrawal from abuse of cocaine, ethanol, nicotine or benzodiazepines, pain, disorders associated with spinal trauma or head injury, hydrocephalus, functional bowel disorder, Irritable Bowel Syndrome, obesity and type-2 diabetes.

3 Claims, No Drawings

(56) References Cited

OTHER PUBLICATIONS

Molnar, "New drug policy in childhood obesity," 2005, International Journal of Obesity, 29:S62-S65.

"pain," Merck Manuals Online Medical Library: Home Edition. Accessed Mar. 24, 2009. http://www.merck.com/mmhe/sec06/ch078/ch078a.html.

Světlík, J. et al., "Unexpected Ring Closure Reaction of [alpha], [beta]-Unsaturated Ketones with Aminoguanidine. Entry into 1,3,5-Trisubstituted Pyrazoles," *Journal of Heterocyclic Chemistry*, U.S., vol. 39, No. 2, (2002), pp. 363-366, XP002468177.

Scott, F. L., et al., "Mechanism of Pyrazoline Formation from the Reactions of Substituted Hydrazines and Mannich Bases," *J. Chem. Soc. (C)*, 1971, pp. 80-86, XP009094752.

Database CHEMCATS [Online], *Chemical Abstracts Service*, Columbus, Ohio, US; (Apr. 7, 2004), XP002465985, Database accession No. 672331-19-0, compound of Registry No. 672331-19-0.

Database CAOLD [Online], *Chemical Abstracts Service*, Columbus, Ohio, US; (Jun. 11, 1988), XP002468179, Database accession No. 114794-17-1, compound of Registry No. 114794-17-1.

Database CHEMCATS [Online] Chemical Abstracts Service, Columbus, Ohio, US; (Sep. 2, 2003), XP002468180, Database accession No. 577791-34-5, compound of Registry No. 577791-34-5.

Scott, et al., "Nitrogen Systems. Part XIV[1]: The Synthesis of 1-Guanyl-Pyrazolines," *Chimia*, Aarau, Ch, vol. 12, 1958, pp. 148-150, XP009094703.

Morales, M. et al., "Coexistence of Serotonin 3 ($5-HT_3$) and CB1 Cannabinoid Receptors in Interneurons of Hippocampus and bentate Gyrus," *Hippocampus*, 2002, pp. 756-764, XP002468178.

International Search Report and Written Opinion, dated Mar. 3, 2008, issued in PCT/EP2007/059944.

Stillman, Mark; "Clinical approach to patients with neuropathic pain." Cleveland Clinic Journal of Medicine, 73(8), (2006) pp. 726-730; 733-739.

Davies et al., "Drug discovery targets: $5-HT_6$ receptor", Drugs of the Future 2005, vol. 30, No. 5, pp. 479-495.

Backvall, J. E., "Modern Oxidation Methods," Wiley-VCH Verlag GmbH & Co. KGaA, pp. 1-8, (2010).

Mitchell et al., "$5-HT_6$ receptors: a novel target for cognitive enhancement", Pharmacology & Therapeutics, 2005, vol. 108, pp. 320-333.

Holenz et al., "Medicinal chemistry strategies to $5-HT_6$ receptor ligands as potential cognitive enhancers and antiobesity agents", Drug Discovery Today, Apr. 2006, vol. 11, No. 7/8, pp. 283-299.

* cited by examiner

SULFONYLPYRAZOLE AND SULFONYLPYRAZOLINE CARBOXAMIDINE DERIVATIVES AS 5-HT$_6$ ANTAGONISTS

This is a divisional application of application Ser. No. 11/859,323, filed Sep. 21, 2007 now U.S. Pat. No. 7,728,018, which claims the benefit of U.S. Provisional Application Nos. 60/846,406, filed Sep. 22, 2006 and 60/902,865, filed Feb. 23, 2007, all of which are incorporated herein by reference.

This invention relates to the fields of pharmaceutical and organic chemistry, and provides sulfonylpyrazoline carboxamidine derivatives, intermediates, formulations and methods.

Serotonin (5-hydroxytryptamine or 5-HT), a key transmitter of the peripheral and central nervous system, modulates a wide range of physiological and pathological functions, mediated through a number of receptor families termed 5-HT$_1$, 5-HT$_2$, 5-HT$_3$, 5-H$_4$, 5-HT$_5$, 5-HT$_6$ and 5-HT$_7$. Although the functions of the latter three are less well understood than those of the others, it is generally accepted that compounds which selectively interfere with 5-HT-mediated signal transduction are important novel drug targets.

The rat 5-HT$_6$ receptor was cloned by two different groups (Ruat, 1993; Sebben, 1994), and that of the human, sharing a 89% sequence identity, shortly thereafter (Kohen, 1996). Much of the recent interest in the 5-HT$_6$ receptor is because several psychotropic agents are high affinity antagonists at the human 5-HT$_6$ receptor (Kohen, 1996; Roth, 1994). These compounds include amitriptyline ($K_i$=65 nM) and the atypical antipsychotics clozapine ($K_i$=9.5 nM), olanzapine ($K_i$=10 nM), and quetiapine ($K_i$=33 nM). None of these compounds, however, is selective. The first selective 5-HT$_6$ receptor antagonists reported are Ro 04-6790 and Ro 63-0563. Their usefulness is limited by their moderate affinity ($K_i$=50 nM and 12 nM, respectively) and poor pharmacokinetics (Sleight, 1998). With the recent development of the selective 5-HT$_6$ receptor antagonists Ro-04-6790 and SB-271046, there have been several reports on the activity of these compounds in models of cognitive function. SB-271046 improved performance in the Morris water maze (Rogers, 1999). These results are consistent with the finding that chronic intracerebroventricular administration of antisense oligonucleotides directed toward the 5-HT$_6$ receptor sequence led to improvements in some measures of performance in the Morris water maze (Bentley, 1999[b]). Recently, the effect of 5-HT$_6$ antagonists and 5-HT$_6$ antisense oligonucleotides to reduce food intake in rats has been reported (Bentley, 1997; Bentley, 1999[a]; Woolley, 2001). Obesity is a condition characterized by an increase in body fat content resulting in excess body weight above accepted norms. Obesity is the most important nutritional disorder in the western world and represents a major health problem in all industrialized countries. This disorder leads to increased mortality due to increased incidences of diseases such as cardiovascular disease, digestive disease, respiratory disease, cancer and type-2 diabetes.

5-HT$_6$ selective ligands have been identified as potentially useful in the treatment or prophylaxis of certain disorders of the central nervous system such as Parkinson's disease, Huntington's chorea and/or schizophrenia, anxiety, depression, manic depression, psychoses, epilepsy, obsessive compulsive disorders, mood disorders, migraine, Alzheimer's disease (enhancement of cognitive memory), age related cognitive decline, mild cognitive impairment, neurodegenerative diseases characterized by impaired neuronal growth, sleep disorders, feeding disorders such as anorexia and bulimia, binge eating disorders, panic attacks, akathisia, attention deficit hyperactivity disorder (ADHD), attention deficit disorder (ADD), withdrawal from drug abuse such as cocaine, ethanol, nicotine and benzodiazepines, and pain, and also disorders associated with spinal trauma and/or head injury such as hydrocephalus. 5-HT$_6$ selective ligands are also expected to be of use in the treatment of certain gastrointestinal disorders such as functional bowel disorder and Irritable Bowel Syndrome and in the treatment or prophylaxis of obesity and type-2 diabetes, to achieve reduction of body weight and of body weight gain. The reduction of body weight and of body weight gain (e.g., treating body-weight disorders) is achieved, inter alia, by reduction of food intake.

The goal of the present invention is to provide compounds that are potent and selective 5-HT$_6$ antagonists chemically unrelated to any of the known 5-HT$_6$ antagonists, which are useful for the treatment of certain CNS disorders.

DESCRIPTION OF THE INVENTION

Surprisingly it was found that certain sulfonylpyrazoline carboxamidine derivatives are 5-HT$_6$ receptor antagonists. In one embodiment, the invention relates to a compound of the general formula (1):

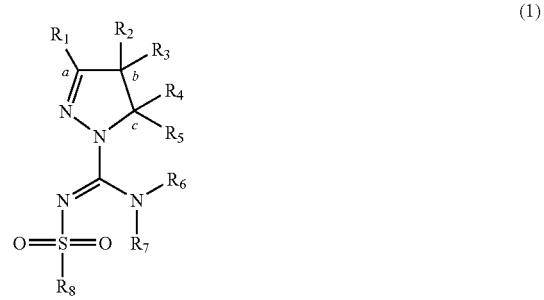

or a tautomer, stereoisomer, N-oxide, isotopically-labeled analogue, or a pharmacologically acceptable salt, hydrate or solvate of any of the foregoing, wherein:

$R_1$ is chosen from hydrogen, an unsubstituted alkyl($C_{1-4}$) group, an alkyl($C_{1-4}$) group substituted with one or more halogen atoms, and a phenyl group optionally substituted with one or more halogen atoms;

$R_2$ and $R_3$ independently are chosen from hydrogen, an unsubstituted alkyl($C_{1-4}$) group,
an alkyl($C_{1-4}$) group substituted with one or more halogen atoms, an alkyl($C_{1-4}$)—O-alkyl($C_{1-4}$)-phenyl group optionally substituted with one or more halogen atoms, and a phenyl group optionally substituted with one or more halogen atoms, or, $R_1$ and $R_2$, together with the carbon atoms marked 'a' and 'b' form a $C_{5-8}$-cycloalkyl ring, or, $R_2$ and $R_3$, together with the carbon atom marked 'b' form a $C_{3-8}$-cycloalkyl ring, or $R_2$ and $R_3$, together with the carbon atom marked 'b' form an optionally substituted $C_{5-8}$-heterocycloalkyl ring;

$R_4$ and $R_5$ independently are chosen from hydrogen, an unsubstituted alkyl($C_{1-4}$) group, an alkyl($C_{1-4}$) group substituted with one or more halogen atoms, an optionally substituted monocyclic aromatic group, an optionally substituted fused-bicyclic aromatic group, an optionally substituted monocyclic hetero-aromatic group, and an optionally substituted fused-bicyclic hetero-aromatic group, or, $R_3$ and $R_4$, together with the carbon atoms marked 'b' and 'c' form a $C_{3-8}$-cycloalkyl ring, or $R_3$ and $R_4$, together with the carbon atoms marked 'b' and form an optionally substituted $C_{5-8}$-heterocycloalkyl ring;

$R_6$ and $R_7$ independently are chosen from a hydrogen atom, an alkyl($C_{1-4}$) group, an alkyl($C_{1-4}$) group substituted with one or more halogen atoms, a ($C_{1-3}$) alkoxy group, a dialkyl($C_{1-3}$)-amino-alkyl($C_{1-3}$) group, an optionally substituted monocyclic, fused bicyclic aromatic, or hetero-aromatic group, an optionally substituted $C_{5-8}$-cycloalkyl group, and an optionally substituted $C_{5-8}$-heterocycloalkyl group, or $R_6$ and $R_7$, together with the nitrogen atom to which they are attached, form an optionally substituted $C_{5-8}$-heterocycloalkyl group; and $R_8$ is chosen from an optionally substituted monocyclic aromatic group, an optionally substituted fused-bicyclic aromatic group, an optionally substituted monocyclic hetero-aromatic group, an optionally substituted fused-bicyclic hetero-aromatic group, an —$CR_9$=$CR_{10}$-aryl group wherein $R_9$ and $R_{10}$ independently are chosen from hydrogen, an alkyl-($C_{1-3}$) group, an —C≡C-aryl group, an optionally substituted piperidinyl group, and a group —$NR_{11}R_{12}$, wherein $R_{11}$ and $R_{12}$ independently are chosen from hydrogen, an alkyl-($C_{1-3}$) group, and an optionally substituted phenyl or benzyl group, In another embodiment, the invention relates to racemates, mixtures of diastereomers as well as the individual stereoisomers of the compounds having formula (1). The invention also relates to the E isomer, Z isomer and E/Z mixtures of compounds having formula (1).

In another embodiment, the invention relates to a compound of the general formula (1) or a tautomer, stereoisomer, N-oxide, isotopically-labeled analogue, or a pharmacologically acceptable salt, hydrate or solvate of any of the foregoing, wherein:

$R_1$ is hydrogen, or $R_1$ and $R_2$, together with the carbon atoms marked 'a' and 'b' form a cyclohexyl ring;

$R_2$ and $R_3$ independently are chosen from hydrogen and an alkyl($C_{1-3}$) group, or $R_2$ and $R_3$, together with the carbon atom marked 'b' form a cyclopentyl or cyclohexyl ring;

$R_4$ and $R_5$ independently are chosen from hydrogen, and an alkyl($C_{1-3}$) group, or $R_3$ and $R_4$, together with the carbon atoms marked 'b' and 'c' form a $C_{3-8}$-cycloalkyl ring;

$R_6$ and $R_7$ independently are chosen from a hydrogen atom, an alkyl($C_{1-3}$) group, an alkyl($C_{1-4}$) group substituted with one or more halogen atoms, a methoxy group, a cyclohexyl group, a benzyl group, and a 4-piperidinyl group; and $R_8$ has the meaning as given above.

In another embodiment, the invention relates to compounds of the general formula (1) or a tautomer, stereoisomer, N-oxide, isotopically-labeled analogue, or a pharmacologically acceptable salt, hydrate or solvate of any of the foregoing, wherein: $R_1$, $R_4$, $R_5$ and $R_6$ are hydrogen, $R_2$ and $R_3$ independently are an alkyl($C_{1-3}$) group, or $R_2$ and $R_3$, together with the carbon atom marked 'b' form a cyclopentyl, or cyclohexyl ring, $R_7$ is an alkyl($C_{1-3}$) group, and $R_8$ has the meaning as given above.

In another embodiment the invention relates to compounds of formula (1) wherein either one, or both, of the two potentially asymmetric carbon atoms in the pyrazoline ring is the levorotatory or dextrorotatory enantiomer.

The compounds of the invention of formula (1), as well as the pharmacologically acceptable salts thereof, have 5-HT$_6$ receptor antagonistic activity. They are useful in treating disorders involving 5-HT$_6$ receptors, or treatable by manipulation of those receptors. For instance, the compounds of formula (1) can be used to treat at least one disease or condition chosen from Parkinson's disease, Huntington's chorea, schizophrenia, anxiety, depression, manic depression, psychoses, epilepsy, obsessive compulsive disorders, mood disorders, migraine, Alzheimer's disease, age related cognitive decline, mild cognitive impairment, sleep disorders, eating disorders, anorexia, bulimia, binge eating disorders, panic attacks, akathisia, attention deficit hyperactivity disorder, attention deficit disorder, withdrawal from abuse of cocaine, ethanol, nicotine or benzodiazepines, pain, disorders associated with spinal trauma or head injury, hydrocephalus, functional bowel disorder, Irritable Bowel Syndrome, obesity and type-2 diabetes.

Other embodiments of the invention include, but are not limited to:

pharmaceutical compositions for treating, for example, a disorder or condition treatable by blocking 5-HT$_6$ receptors, the composition comprising a compound of formula (1) or a pharmaceutically acceptable salt thereof, and a pharmaceutically acceptable carrier;

methods of treating a disorder or condition treatable by blocking 5-HT$_6$ receptors, the method comprising administering to a mammal in need of such treating a compound of formula (1) or a pharmaceutically acceptable salt thereof;

pharmaceutical compositions for treating, for example, a disorder or condition chosen from the disorders listed herein;

methods of treating a disorder or condition chosen from the disorders listed herein, the methods comprising administering to a mammal in need of such treating a compound of formula (1) or a pharmaceutically acceptable salt thereof;

pharmaceutical compositions for treating a disorder or condition chosen from the disorders listed herein, the compositions comprising a compound of formula (1) or a pharmaceutically acceptable salt thereof, and a pharmaceutically acceptable carrier;

methods for treating a disorder or condition chosen from the disorders listed herein, the methods comprising administering to a patient in need of such treating a compound of formula (1) or a pharmaceutically acceptable salt thereof; and methods of antagonizing a 5-HT$_6$ receptor that comprises administering to a subject in need thereof, an effective amount of a compound of formula (1).

The invention also provides the use of a compound or salt according to formula (1) for the manufacture of medicament.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for treating one or more of the conditions listed. Such other therapeutic agent(s) may be administered prior to, simultaneously with, or following the administration of the compounds of the invention.

The invention also provides compounds, pharmaceutical compositions, kits and methods for treating a disorder or condition chosen from the disorders listed herein, the method comprising administering to a patient in need of such treating a compound of formula (1) or a pharmaceutically acceptable salt thereof.

The compounds of the invention possess 5-HT$_6$ receptor antagonizing activity. This activity of the compounds of the invention is readily demonstrated, for example, using one or more of the assays described herein or known in the art.

The invention also provides methods of preparing the compounds of the invention and the intermediates used in those methods.

Isolation and purification of the compounds and intermediates described herein can be affected, if desired, by any suitable separation or purification procedure such as, for example, filtration, extraction, crystallization, column chromatography, thin-layer chromatography, thick-layer chromatography, preparative low or high-pressure liquid chromatography, or a combination of these procedures. Specific illustrations of suitable separation and isolation procedures can be taken from the preparations and examples. However, other equivalent separation or isolation procedures could, of course, also be used.

The compounds of the present invention may contain one or more asymmetric centers and can thus occur as racemates and racemic mixtures, single enantiomers, diastereomeric mixtures and individual diastereomers.

Depending on the nature of the various substituents, the molecule can have additional asymmetric centers. Each such asymmetric center will independently produce two optical isomers. AU of the possible optical isomers and diastereomers, in mixtures and as pure or partially purified compounds, belong to this invention. The present invention comprehends all such isomeric forms of these compounds. Formula (1) shows the structure of the class of compounds without preferred stereochemistry. The independent syntheses of these diastereomers, or their chromatographic separations, may be achieved as known in the art by appropriate modification of the methodology disclosed therein. Their absolute stereochemistry may be determined by the X-ray crystallography of crystalline products or crystalline intermediates, which are derivatized, if necessary, with a reagent containing an asymmetric center of known absolute configuration. Racemic mixtures of the compounds can be separated into the individual enantiomers by methods well-known in the art, such as the coupling of a racemic mixture of compounds to an enantiomerically pure compound to form a diastereomeric mixture, followed by separation of the individual diastereomers by standard methods, such as fractional crystallization or chromatography. The coupling often consists of the formation of salts using an enantiomerically pure acid or base, for example (−)-di-p-toluoyl-D-tartaric acid and/or (+)-di-p-toluoyl-L-tartaric acid. The diasteromeric derivatives may then be converted to the pure enantiomers by cleavage of the added chiral residue. The racemic mixture of the compounds can also be separated directly by chromatographic methods utilizing chiral stationary phases, which are methods well-known in the art. Alternatively, any enantiomer of a compound may be obtained by stereoselective synthesis using optically pure starting materials or reagents of known configuration by methods well-known in the art.

Cis and trans isomers of the compound of formula (1), or a pharmaceutically acceptable salt thereof, also belong to the invention, and this also applies to tautomers of the compounds of formula (1) or a pharmaceutically acceptable salt thereof.

Some of the crystalline forms for the compounds may exist as polymorphs, which are also intended to belong to the invention. In addition, some of the compounds may form solvates with water (i.e. hydrates), or common organic solvents. Such solvates also fall within the scope of this invention.

Isotopically-labeled compound of formula (1) or pharmaceutically acceptable salts thereof, including compounds of formula (1) isotopically-labeled to be detectable by PET or SPECT, also fall within the scope of the invention. The same applies to compounds of formula (1) labeled with [$^{13}$C]-, [$^{14}$C]-, [$^{3}$H]-, [$^{18}$F]-, [$^{125}$I]- or other isotopically enriched atoms, suitable for receptor binding or metabolism studies.

The compounds of the invention may also be used as reagents or standards in the biochemical study of neurological function, dysfunction and disease.

Definitions

General terms used in the description of compounds herein disclosed bear their usual meanings. The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, Pert-butyl, pentyl, isopentyl, neopentyl, Pert-pentyl, hexyl, isohexyl, heptyl, octyl, nonyl, decyl, undecyl, dodecyl, tridecyl, tetradecyl, pentadecyl, hexadocyl, heptadecyl, octadecyl, and the like. When qualified as 'lower', the alkyl group will contain from 1 to 6 carbon atoms. The same carbon content applies to the parent term "alkane", and to derivative terms such as alkoxy". The carbon content of various hydrocarbon containing moieties is indicated by a prefix designating the minimum and maximum number of carbon atoms in the moiety, i.e., the prefix $C_x$-$C_y$ defines the number of carbon atoms present from the integer "x" to the integer "y" inclusive. "Alkyl($C_{1-3}$)" for example, means methyl, ethyl, n-propyl or isopropyl, and alkyl($C_{1-4}$) means 'methyl, ethyl, n-propyl, isopropyl, n-butyl, 2-butyl, isobutyl or 2-methyl-n-propyl'. The term "alkenyl" denotes straight or branched hydrocarbon radicals having one or more carbon-carbon double bonds, such as vinyl, allyl, butenyl, etc., and for example represents ($C_{2-4}$alkenyl. In "alkynyl" groups the straight or branched hydrocarbon radicals have one or more carbon-carbon triple bonds, such as ethynyl, propargyl, 1-butynyl, 2-butynyl, etc., and for example represent ($C_{2-4}$alkynyl. Unless otherwise stated, alkenyl and alkynyl chains can contain from 1 to 18 carbon atoms. The term "acyl" means alkyl($C_{1-3}$) carbonyl, arylcarbonyl or aryl-alkyl($C_{1-3}$)carbonyl.

The term "aryl" embraces monocyclic or fused bicyclic aromatic or hetero-aromatic groups, including but not limited to furyl, thienyl, pyrrolyl, oxazolyl, thiazolyl, imidazolyl, imidazo[2,1-b][1,3]thiazolyl, pyrazolyl, isoxazolyl, isothiazolyl, pyridyl, pyridazinyl, pyrimidinyl, pyrazinyl, 1,3,5-triazinyl, phenyl, indazolyl, indolyl, indolizinyl, isoindolyl, benzo[b]furanyl, 1,2,3,4-tetrahydro-naphtyl, 1,2,3,4-tetrahydroisoquinolinyl, indanyl, indenyl, benzo[b]thienyl, 2,3-dihydro-1,4-benzodioxin-5-yl, benzimidazolyl, benzothiazolyl, benzo[1,2,5]thia-diazolyl, purinyl, quinolinyl, isoquinolinyl, phtalazinyl, quinazolinyl, quinoxalinyl, 1,8-naphthyridinyl, naphthyl, pteridinyl or azulenyl. "Halo" or "Halogen" means chloro, fluoro, bromo or iodo; "hetero" as in 'heteroalkyl, heteroaromatic' etc. means containing one or more N, O or S atoms. heteroalkyl includes alkyl groups with heteroatoms in any position, thus including N-bound O-bound or S-bound alkyl groups, The term "substituted" means that the specified group or moiety bears one or more substituents. Where any group may carry multiple substituents, and a variety of possible substituents is provided, the substituents are independently selected, and need not to be the same. The term "unsubstituted" means that the specified group bears no substituents. "Optionally substituted" means that a group may or may not be further substituted by one or more groups selected from $C_{1-8}$ alkyl, $C_{1-8}$ alkenyl, $C_{1-8}$ alkynyl, aryl, fluoro, chloro, bromo, hydroxyl, $C_{1-8}$ alkyloxy, alkenyloxy, aryloxy, acyloxy, amino, $C_{1-8}$ alkylamino, dialkyl($C_{1-8}$)-amino, arylamino, thio, $C_{1-8}$ alkylthio, arylthio, alkylsulfonyl, arylsulfonyl, alkylsulfinyl, arylsulfinyl, cyano, oxo, nitro, acyl, amido, $C_{1-8}$ alkylamido, dialkyl($C_{1-8}$)amido, carboxyl, or two optional substituents may together with the carbon atoms to which they are attached form a 5- or 6-membered aromatic or non-aromatic ring containing 0, 1 or 2 heteroatoms selected from nitrogen, oxygen or sulphur. Optional substituents may themselves bear additional optional substituents. Some examples of optional substituents include $C_{1-3}$ alkyl such as for example methyl, ethyl, and trifluoromethyl, fluoro, chloro, bromo, hydroxyl, $C_{1-3}$ alkyloxy such as for example methoxy, ethoxy and trifluoromethoxy, and amino. With reference to substituents, the term "independently" means that when more than one of such substituents are possible, they may be the same or different from each other.

"$C_{3-8}$-cycloalkyl" means cyclopropyl, cyclobutyl, cyclopentyl, cyclohexyl, cycloheptyl or cyclooctyl; "$C_{5-8}$ heterocycloalkyl" refers to heteroatom containing rings including but not limited to piperidinyl, morpholinyl, azepanyl, pyrrolidinyl, thiomorpholinyl, piperazinyl, tetrahydrofuryl, tetrahydropyranyl; "$C_{5-10}$ bicycloalkyl group" refers to carbobicyclic ring systems including but not limited to bicyclo [2.2.1]heptanyl, bicyclo[3.3.0]octanyl or the bicyclo[3.1.1] heptanyl group; "$C_{6-10}$ tricycloalkyl group" refers to carbotricyclic ring systems including but not limited to the 1-adamantyl, noradamantyl or the 2-adamantyl group. The abbreviation "$C_{8-11}$ tetracycloalkyl group" refers to carbotetracyclic ring systems including but not limited to the cubyl, homocubyl or bishomocubyl group.

The terms "oxy", "thio" and "carbo" as used herein as part of another group respectively refer to an oxygen atom, a sulphur atom and a carbonyl (C=O) group, serving as linker between two groups, such as for instance hydroxyl, oxyalkyl, thioalkyl, carboxyalkyl, etc. The term "amino" as used herein alone, or as part of another group, refers to a nitrogen atom that may be either terminal, or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. The terms "sulfinyl" and "sulfonyl" as used herein as part of another group respectively refer to an —SO— or an —SO$_2$— group.

As used herein, the term "leaving group" (L) shall mean a charged or uncharged atom or group that departs during a substitution or displacement reaction. The term refers to groups readily displaceable by a nucleophile, such as an amine, a thiol or an alcohol nucleophile. Such leaving groups are well known in the art. Examples include, but are not limited to, N-hydroxysuccinimide, N-hydroxybenzotriazole, halides (Br, Cl, I), triflates, mesylates, tosylates, and the like.

N-oxides of the compounds mentioned above belong to the invention. Tertiary amines may or may not give rise to N-oxide metabolites. The extent to what N-oxidation takes place varies from trace amounts to a near quantitative conversion. N-oxides may be more active than their corresponding tertiary amines, or less active. Whilst N-oxides can easily be reduced to their corresponding tertiary amines by chemical means, in the human body this happens to varying degrees. Some N-oxides undergo nearly quantitative reductive conversion to the corresponding tertiary amines, in other cases conversion is a mere trace reaction, or even completely absent (Bickel, 1969).

Any compound metabolized in vivo to provide the bioactive agent (i.e., the compound of formula (1)) is a prodrug within the scope and spirit of the application. Prodrugs are therapeutic agents, inactive per se, but transformed into one or more active metabolites. Thus, in the methods of treatment of the present invention, the term "administering" shall encompass treating the various disorders described with the compound specifically disclosed, or with a compound that not specifically disclosed, but that converts to the specified compound in vivo after administration to the patient. Prodrugs are bioreversible derivatives of drug molecules used to overcome some barriers to the utility of the parent drug molecule. These barriers include, but are not limited to, solubility, permeability, stability, presystemic metabolism and targeting limitations (Bundgaard, 1985; King, 1994; Stella, 2004; Ettmayer, 2004; Järvinen, 2005). Prodrugs, i.e. compounds that when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present that is easily removed after administration, for instance, but not limited to amidine, enamine, a Mannich base, a hydroxyl-methylene derivative, an O-(acyloxymethylene carbamate) derivative, carbamate, ester, amide or enaminone.

"Crystal form" refers to various solid forms of the same compound, for example polymorphs, solvates and amorphous forms. "Polymorphs" are crystal structures in which a compound can crystallize in different crystal packing arrangements, all of which have the same elemental composition. Polymorphism is a frequently occurring phenomenon, affected by several crystallization conditions such as temperature, level of supersaturation, the presence of impurities, polarity of solvent, rate of cooling. Different polymorphs usually have different X-ray diffraction patterns, solid state NMR spectra, infrared or Raman spectra, melting points, density, hardness, crystal shape, optical and electrical properties, stability, and solubility. Recrystallization solvent, rate of crystallization, storage temperature, and other factors may cause one crystal form to dominate. "Solvates" are generally a crystal form that contains either stoichiometric or non-stoichiometric amounts of a solvent. Often, during the process of crystallization some compounds have a tendency to trap a fixed molar ratio of solvent molecules in the crystalline solid state, thus forming a solvate. When the solvate is water, "hydrates" may be formed. The compound of formula (1) and pharmaceutically acceptable salts thereof may exist in the form of a hydrate or a solvate, and such a hydrate and solvate are also encompassed in the present invention. Examples thereof include 1/10 hydrate, 1/4 hydrate, 1/2 hydrate, monohydrate, dihydrochloride 1/2 hydrate, dihydrochloride dihydrate, dihydrochloride 3/2 hydrate, and the like. "Amorphous" forms are noncrystalline materials with no long range order, and generally do not give a distinctive powder X-ray diffraction pattern. Crystal forms in general have been described by Byrn (1995) and Martin 0995)

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The terms "selective" and "selectivity" refer to compounds that display reactivity towards a particular receptor (e.g. a $5\text{-HT}_6$ receptor) without displaying substantial cross-reactivity towards another receptor (e.g. other 5-HT receptor subtypes). Thus, for example, selective compounds of the present invention may display reactivity towards $5\text{-HT}_6$ receptors without displaying substantial cross-reactivity towards other 5-HT receptors. In one embodiment, a compound of the present invention has at least about 10-fold selectivity to the $5\text{-HT}_6$ receptor, at least about 50-fold selectivity to the $5\text{-HT}_6$ receptor, at least about 100-fold selectivity to $5\text{-HT}_6$ receptor, at least about 250-fold selectivity to the $5\text{-HT}_6$ receptor, or at least about 500-fold selectivity to the desired target.

Throughout the description and the claims of this specification the word "comprise" and variations of the word, such as "comprising" and "comprises" is not intended to exclude other additives, components, integers or steps.

While it may be possible for the compounds of formula (1) to be administered as the raw chemical, the compounds of formula (1) may be present as a component of a "pharmaceutical composition". According to a further aspect, the present invention provides a pharmaceutical composition comprising a compound of formula (1), or a pharmaceutically acceptable salt or solvate thereof, together with one or more pharmaceutically acceptable carriers thereof, and optionally one or more other therapeutic ingredients. The carrier(s) must be 'acceptable' in the sense of being compatible with the other ingredients of the formulation and not deleterious to the recipient thereof.

The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Within the context of this application, the term "combination preparation" comprises both true combinations, meaning a compound of formula (1) and one or more other medicaments physically combined in one preparation such as a tablet or injection fluid, as well as "kit-of-parts", comprising a compound of formula (1) and one or more other medicaments in separate dosage forms, together with instructions for use, optionally with further means for facilitating compliance with the administration of the component compounds, e.g. label or drawings. With true combinations, the pharmacotherapy by definition is simultaneous. The contents of 'kit-of-parts', can be administered either simultaneously or at different time intervals. Therapy being either concomitant or sequential will be dependant on the characteristics of the other medicaments used, characteristics like onset and duration of action, plasma levels, clearance, etc., as well as on the disease, its stage, and characteristics of the individual patient.

The affinity of the compounds of the invention for $5\text{-HT}_6$ receptors was determined as described above. From the binding affinity measured for a given compound of formula (1), one can estimate a theoretical lowest effective dose. At a concentration of the compound equal to twice the measured $K_i$-value, nearly 100% of the $5\text{-HT}_6$ receptors likely will be occupied by the compound. Converting that concentration to mg of compound per kg of patient yields a theoretical lowest effective dose, assuming ideal bioavailability. Pharmacokinetic, pharmaco-dynamic, and other considerations may alter the dose actually administered to a higher or lower value. The typical daily dose of the active ingredients varies within a wide range and will depend on various factors such as the relevant indication, the route of administration, the age, weight and sex of the patient, and may be determined by a physician. In general, total daily dose administration to a patient in single or individual doses, may be in amounts, for example, from 0.001 to 10 mg/kg body weight daily, and more usually from 0.01 to 1,000 mg per day, of total active ingredients. Such dosages will be administered to a patient in need of treatment from one to three times each day, or as often as needed for efficacy, and for periods of at least two months, more typically for at least six months, or chronically.

The term "therapeutically effective amount" as used herein refers to an amount of a therapeutic agent to treat a condition treatable by administrating a composition of the invention. That amount is the amount sufficient to exhibit a detectable therapeutic or ameliorative response in a tissue system, animal or human. The effect may include, for example, treating the conditions listed herein. The precise effective amount for a subject will depend upon the subject's size and health, the nature and extent of the condition being treated, recommendations of the treating physician (researcher, veterinarian, medical doctor or other clinician), and the therapeutics, or combination of therapeutics, selected for administration. Thus, it is not useful to specify an exact effective amount in advance.

The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids (Berge, 1977). The "free base" form may be regenerated by contacting the salt with a base or acid, and isolating the parent compound in the conventional matter. The parent form of the compound differs from the various salt forms in certain physical properties, such as solubility in polar solvents, but otherwise the salts are equivalent to the parent form of the compound for the purposes of the present invention.

"Complex" refers to a complex of the compound of the invention, e.g. formula (1), complexed with a metal ion, where at least one metal atom is chelated or sequestered. Complexes are prepared by methods well known in the art (Dwyer, 1964).

The term "treatment" as used herein refers to any treatment of a mammalian, for example human condition or disease, and includes: (1) inhibiting the disease or condition, i.e., arresting its development, (2) relieving the disease or condition, i.e., causing the condition to regress, or (3) stopping the symptoms of the disease.

The term "inhibit" includes its generally accepted meaning which includes prohibiting, preventing, restraining, alleviating, ameliorating, and slowing, stopping or reversing progression, severity, or a resultant symptom. As such, the present method includes both medical therapeutic and/or prophylactic administration, as appropriate.

As used herein, the term "medical therapy" includes prophylactic, diagnostic and therapeutic regimens carried out in vivo or ex vivo on humans or other mammals.

"Mammals" include animals of economic importance such as bovine, ovine, and porcine animals, especially those that produce meat, as well as domestic animals, sports animals, zoo animals, and humans. The term "subject" as used herein, refers to an animal, such as a mammal, for example, a human, who has been the object of treatment, observation or experiment.

As used herein, the term "body weight disorders" refers to the disorders caused by an imbalance between energy intake and energy expenditure, resulting in abnormal (e.g., excessive) body weight. Such body weight-disorders include obesity (Roth, 1994; Sibley, 1993; Sleigh, 1995, 1997). "Obesity" refers to a condition whereby a person has a Body Mass Index (BMI), calculated as weight per height squared (km/m$^2$), of at least 25.9. Conventionally, those persons with normal weight have a BMI of 19.9 to less than 25.9. The obesity herein may be due to any cause, whether genetic of environmental. Examples of disorders that may result in obesity or be the cause of obesity include overeating and bulimia, polycystic ovarian disease, craniopharyngioma, the Prader-Willi syndrome, Frohlich's syndrome, Type-II diabetes, GH-deficient subjects, normal variant short stature, Turners syndrome, and other pathological conditions showing reduced metabolic activity or a decrease in resting energy expenditure as a percentage of total fat-free mass, e.g. children with acute lymphoblastic leukemia.

| ABBREVIATIONS | |
|---|---|
| ACE-chloride | 1-chloroethyl chloroformate |
| ACN | acetonitrile |
| AcOH | acetic acid |
| ADD | attention deficit disorder |
| ADHD | attention deficit hyperactivity disorder |
| API | atmospheric pressure ionisation |
| BMI | body mass index |
| n-BuOH | n-butanol |
| t-BuOH | t-butanol |
| (t)-BOC | (tertiary)-butoxycarbonyl |
| CHO | Chinese Hamster Ovary (cells) |
| CNS | central nervous system |
| CUR | curtain gas |
| DBU | 1,8-diazabicyclo[5.4.0]undec-7-ene |
| (1,2)-DCE | (1,2)-dichloroethane |
| DCM | dichloromethane |
| DF | deflector voltage |
| DIPEA | N,N-diisopropylethylamine |
| DMAP | 4-dimethylaminopyridin |
| DMC | 2-chloro-1,3-dimethylimidazolinium chloride |
| DMF | N,N'-dimethylformamide |
| DMSO | dimethylsulfoxide |
| EA | ethylacetate |
| EP | entrance potential |
| EtOAc | ethylacetate |

-continued

| ABBREVIATIONS | |
|---|---|
| EtOH | ethanol |
| Et$_2$O | diethyl ether |
| FCS | fetal calf serum |
| FP | focusing potential |
| g | gram(s) |
| h | hour(s) |
| 5-HT | 5-hydroxytryptamine, serotonine |
| KOtBu | potassium tert-butoxide |
| MeI | methyl iodide |
| MeOH | methanol |
| mg | milligram(s) |
| min | minute(s) |
| ml or mL | milliliter(s) |
| m.p. | melting point c.q. melting range |
| MsCl | methanesulfonyl chloride (mesyl chloride) |
| MTBE | methyl tert-butylether |
| NaHMDS | sodium hexamethyldisilazane |
| NEB | nebulizer gas |
| PA | petroleum aether (40-60) |
| p-TsOH | paratoluene sulphonic acid |
| R$_f$ | retention factor (thin layer chromatography) |
| R$_t$ | retention time (LC/MS) |
| RT | room temperature |
| SCX | strong cation exchange |
| TBAB | tetrabutylammonium bromide |
| TEA | triethylamine |
| TEM | temperature |
| TFA | trifluoroacetic acid |
| THF | tetrahydrofuran |

EXAMPLE 1

Analytical Methods

Nuclear magnetic resonance spectra ($^1$H NMR) were determined in the indicated solvent using a Bruker ARX 400 ($^1$H: 400 MHz) or a Varian VXR200 ($^1$H: 200 MHz) instrument at 300 K, unless indicated otherwise. The spectra were determined in deuterated chloroform or DMSO obtained from Cambridge Isotope Laboratories Ltd. Chemical. Shifts (δ) are given in ppm downfield from tetramethylsilane (1H). Coupling constants J are given in Hz. Peak shapes in the NMR spectra are indicated with the symbols 'q' (quartet), 'dq' (double quartet), T (triplet), 'dt' (double triplet), 'd' (doublet), 'dd' (double doublet), 'ddd' (double doublet), 's' (singlet), 'bs' (broad singlet) and 'm' (multiplet). NH and OH signals were identified after mixing the sample with a drop of D$_2$O.

Flash chromatography refers to purification using the indicated eluent and silica gel (Merck silica gel 60: 0.040-0.063 mm). Melting points were recorded on a BUchi B-545 melting point apparatus. All reactions involving compounds sensitive to moisture and/or oxygen were carried out under an anhydrous nitrogen atmosphere. Reactions were monitored by using thin-layer chromatography (TLC) on silica coated glass plates (Merck precoated silica gel 60 F254) with the indicated eluent. Spots were visualised by UV light (254 nm) or I$_2$.

Liquid Chromatography-Mass Spectrometry (LC-MS): The LC-MS system consisted of 2 Perkin Elmer series 200 micro pumps. The pumps were connected to each other by a 50 μl tee mixer, connected to a Gilson 215 auto sampler. The method was as follows:

| step | total time | flow (μl/min) | A (%) | B (%) |
|---|---|---|---|---|
| 0 | 0 | 2000 | 95 | 5 |
| 1 | 1.8 | 2000 | 0 | 100 |
| 2 | 2.5 | 2000 | 0 | 100 |
| 3 | 2.7 | 2000 | 95 | 5 |
| 4 | 3.0 | 2000 | 95 | 5 |

A = 100% Water with 0.025% HCOOH and 10 mmol NH₄HCOO pH = ±3
B = 100% ACN with 0.025% HCOOH The auto sampler had a 2 μl injection loop, and was connected to a Waters Atlantis C18 30*4.6 mm column with 3 μm particles. The column was thermostated in a Perkin Elmer series 200 column oven at 40° C. The column was connected to a Perkin Elmer series 200 UV meter with a 2.7 μl flowcel. The wavelength was set to 254 nm. The UV meter was connected to a Sciex API 150EX mass spectrometer. The mass spectrometer had the following parameters:

Scanrange: 150-900 a.m.u.; polarity: positive; scan mode: profile; resolution Q1: UNIT; step size: 0.10 a.m.u.; time per scan: 0.500 sec; NEB: 10; CUR: 10 IS: 5200; TEM: 325; DF: 30; FP: 225 and EP: 10. The light scattering detector was connected to the Sciex API 150. The light scattering detector was a Sedere Sedex 55 operating at 50° C. and 3 bar N₂. The complete system was controlled by a G3 powermac.

EXAMPLE 2

General Aspects of Syntheses

Suitable syntheses of claimed compounds and intermediates containing pyrazoline moieties follow routes analogous to those previously disclosed in WO 01/70700, employing 4,5-dihydro-1H-pyrazole or 4,5-dihydro-3H-pyrazole building blocks, which are either commercially available or prepared as described below.

Route 1

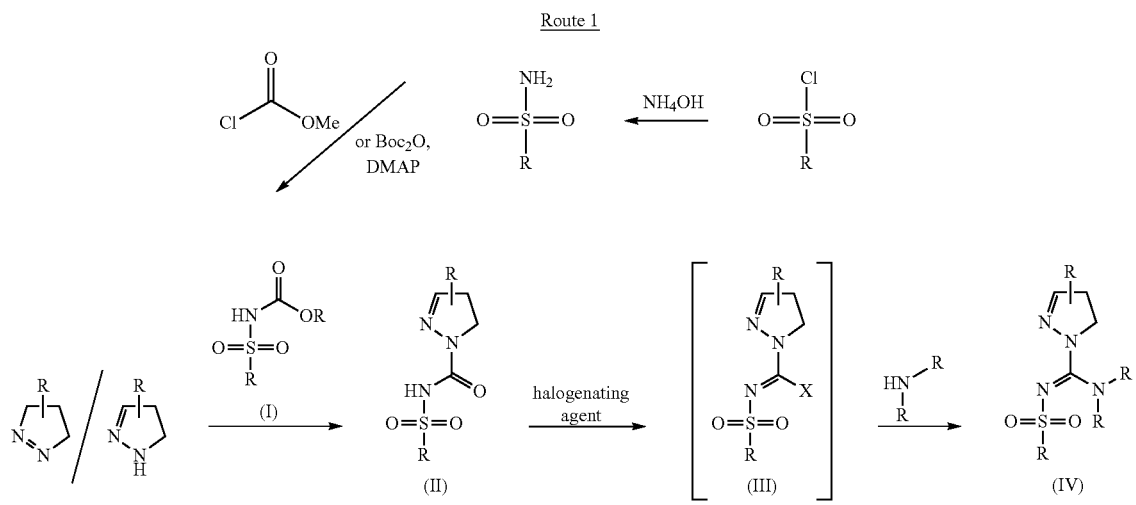

Route 1 employs sulfonyl carbamates of general formula (1), which can for instance be prepared by reaction of sulfonamides with methyl chloroformate or di-tert-butyl dicarbonate in the presence of base. Their reaction products with pyrazolines of general formula (II) can subsequently be converted into the chloroimine intermediates of general formula (III) using halogenating agents such as PCl₃, POCl₃/DMAP or 2-chloro-1,3-dimethylimidazolinium chloride (DMC), followed by reaction with amines to obtain sulfonylpyrazoline carboxamidine derivatives of general formula (IV).

Route 2

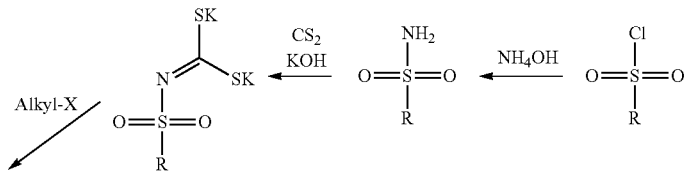

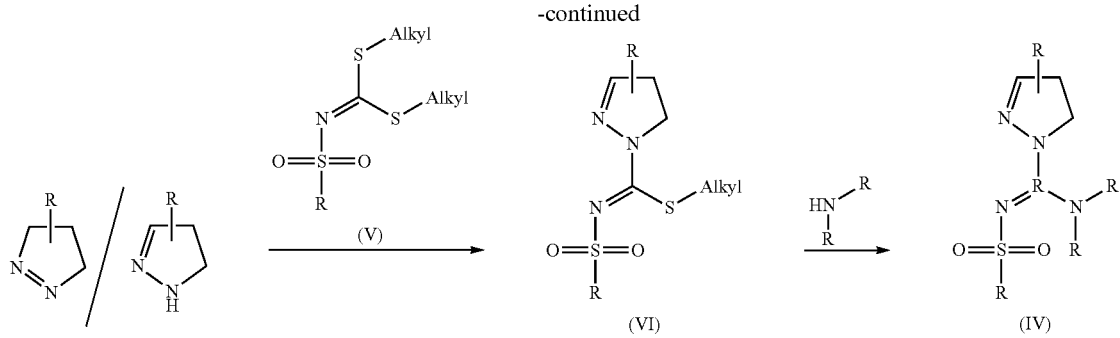

Route 2 employs N-(bis-alkylsulfanyl-methylene)-sulfonamide structures of general formula (V), which may be prepared from sulfonamides by reaction with $CS_2$ in the presence of KOH, followed by reaction with an alkyl halide such as methyl iodide. The two S-alkyl functionalities can subsequently be substituted by amines, for example, starting with the pyrazoline building blocks to obtain structures of general formula (VI), to end with sulfonylpyrazoline carboxamidine derivatives of general formula (IV).

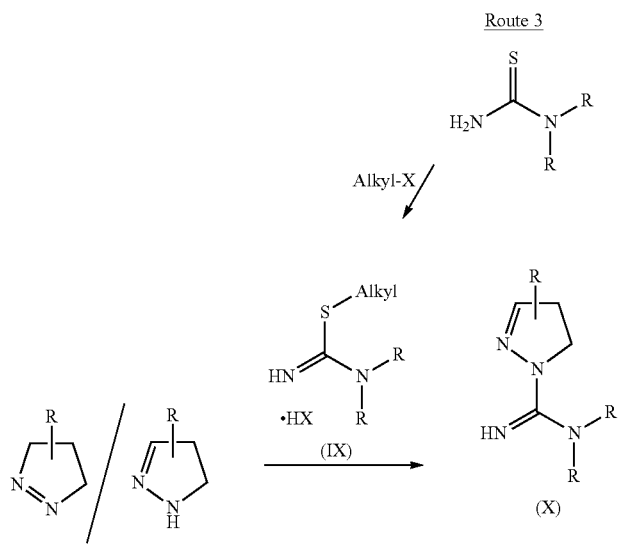

Route 3 employs alkyl-isothiourea fragments or suitable salt forms thereof of general formula (IX), conveniently prepared by reaction of thiourea building blocks with alkyl halides, such as methyl iodide, that can be reacted with pyrazolines in the presence of base to obtain pyrazoline carboxamidine derivatives of general formula (X). The latter can be reacted with sulfonyl halides (X═Br, Cl, F, for example, Cl) in the presence of base to obtain sulfonylpyrazoline carboxamidine derivatives of general formula (IV).

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Pharmaceutically acceptable salts may be obtained using standard procedures well known in the art, for example by mixing a compound of the present invention with a suitable acid, for instance an inorganic acid or an organic acid.

EXAMPLE 3

Syntheses of Pyrazoline Intermediates

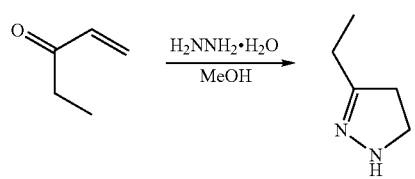

3-Ethyl-4,5-dihydro-1H-pyrazole

Hydrazine hydrate (24.55 mL) was dissolved in MeOH (50 mL) and cooled in an ice bath. To this solution, ethyl vinyl ketone (50 mL) was added at such a rate that the temperature was kept below 10° C. The ice bath was removed and the mixture was stirred for 2 h. at room temperature, after which the MeOH was evaporated under reduced pressure. The product was obtained by vacuum distillation (70° C., 20 mbar), yielding 7.22 g of a colorless liquid. $^1$H NMR (400 MHz, CDCl$_3$) δ 1.15 (t, J=8 Hz, 3H), 2.34 (q, J=8 Hz, 2H), 2.59 (t, J=10 Hz, 2H), 3.10 (br s, 1H), 3.34 (t, J=10 Hz, 2H).

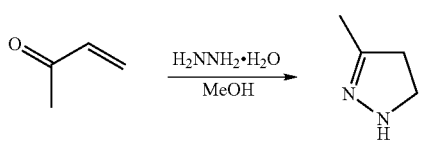

3-Methyl-4,5-dihydro-1H-pyrazole

Hydrazine hydrate (29.2 mL) was dissolved in MeOH (50 mL). To this solution, methyl vinyl ketone (50 mL) was added at such a rate that the temperature was kept below 50° C. The mixture was stirred for 2 h. at 50° C., after which the MeOH was evaporated under reduced pressure. The product was obtained by vacuum distillation (68-82° C., 20 mbar), yielding 11.8 g of a colorless liquid. $^1$H NMR (400 MHz, DMSO-d$_6$) δ 1.88 (s, 3H), 2.47 (t, J=10 Hz, 2H), 3.15 (t, J=10 Hz, 2H), 6.10 (br s, 1H).

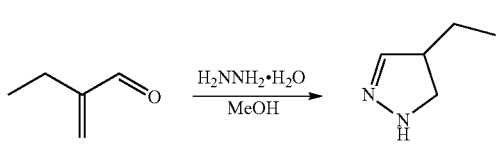

4-Ethyl-4,5-dihydro-1H-pyrazole

Hydrazine hydrate (58 mL) was dissolved in MeOH (300 mL) and cooled in an ice bath. To this mixture, a solution of 2-ethylacrolein (100 g) in MeOH (100 mL) was added at such a rate that the temperature was kept below 10° C. The ice bath was removed and the mixture was stirred overnight at room temperature, after which the MeOH was evaporated under reduced pressure. The product was obtained by vacuum distillation (70-80° C., 20 mbar), yielding 54.9 g of a colorless liquid. $^1$H NMR (400 MHz, CDCl$_3$) δ 0.98 (t, J=8 Hz, 3H), 1.42-1.70 (m, 2H), 2.89-3.02 (m, 2H), 3.43-3.54 (m, 1H), 6.78 (br s, 1H), NH invisible.

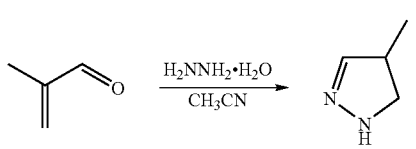

4-Methyl-4,5-dihydro-1H-pyrazole

Hydrazine hydrate (16.65 mL) was dissolved in CH$_3$CN (50 mL) and cooled in an ice bath. To this mixture, a solution of 2-methylacrolein (24.02 g) in CH$_3$CN (50 mL) was added. The ice bath was removed and the mixture was stirred overnight at room temperature, after which the CH$_3$CN was evaporated under reduced pressure. The product was obtained by vacuum distillation (102-108° C., 250 mbar), yielding 7.0 g of a colorless liquid. $^1$H NMR (400 MHz, CDCl$_3$) δ 1.18 (d, J=7 Hz, 3H), 2.90 (t, J=9 Hz, 1H), 3.00-3.12 (m, 1H), 3.51 (t, J=9 Hz, 1H), 5.48 (br s, 1H), 6.73 (br s, 1H).

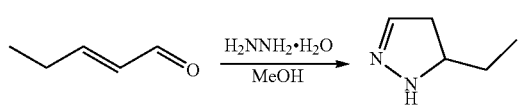

5-Ethyl-4,5-dihydro-1H-pyrazole

Hydrazine hydrate (12.1 mL) was dissolved in MeOH (50 mL) and cooled in an ice bath. To this mixture, a solution of 2-pentenal (24.4 mL) in MeOH (50 mL) was added at such a rate that the temperature was kept below 10° C. The ice bath was removed and the mixture was stirred for 2.5 h. at room temperature, followed by evaporation under reduced pressure. The product was obtained by vacuum distillation (68-72° C., 25 mbar), yielding 8.25 g of a colorless liquid. $^1$H NMR (400 MHz, CDCl$_3$) δ 0.92 (t, J=7.5 Hz, 3H), 1.42-1.61 (m, 2H), 2.36 (ddd, J=17, 8 and 2 Hz, 1H), 2.76 (ddd, J=17, 10 and 2 Hz, 1H), 3.51-3.62 (m, 1H), 5.35 (br s, 1H), 6.76 (br s, 1H).

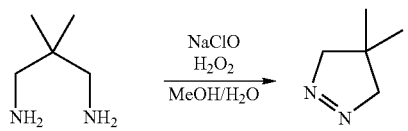

4,4-Dimethyl-4,5-dihydro-3H-pyrazole 2,2-Dimethyl-1,3-propanediamine (20.0 g) was dissolved in H$_2$O (80 mL) and MoOH (20 mL) and cooled in an ice bath. Simultaneously, H$_2$O$_2$ (30%, 120 mL) and NaClO (10%, 350 mL) were added dropwise. The reaction mixture was stirred overnight at room temperature, extracted with DCM, the organic layer dried over Na$_2$SO$_4$ and the solvent evaporated under reduced pressure. Vacuum distillation (102-105° C., 250 mbar), yielded 11.4 g of a colorless amorphous oily compound, $^1$H NMR (200 MHz, CDCl$_3$) δ 1.05 (s, 6H), 4.13 (s, 4H).

Alternatively, this compound was synthesized as follows:

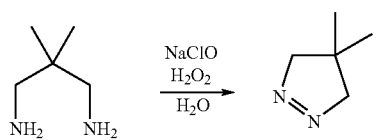

4,4-Dimethyl-4,5-dihydro-3H-pyrazole 2,2-Dimethyl-1,3-propanediamine (8.97 g) was dissolved in H$_2$O (45 mL) and cooled in an ice bath. Simultaneously, H$_2$O$_2$ (30%, 54 mL) and NaClO (10%, 157 mL) were added dropwise, keeping the temperature below 25° C. Subsequently, the reaction mixture was stirred for 1 h. at room temperature, and extracted with DCM (2×45 mL). The combined organic layers were extracted with aqueous sodium sulfite (20%, 25 mL), washed with water (2×25 mL) dried over $Na_2SO_4$, and evaporated under reduced pressure (>200 mbar at 50° C.) to give 8.89 g of a colorless fluid (containing some residual DCM). $^1$H NMR (200 MHz, $CDCl_3$) δ 1.05 (s, 6H), 4.13 (s, 4H).

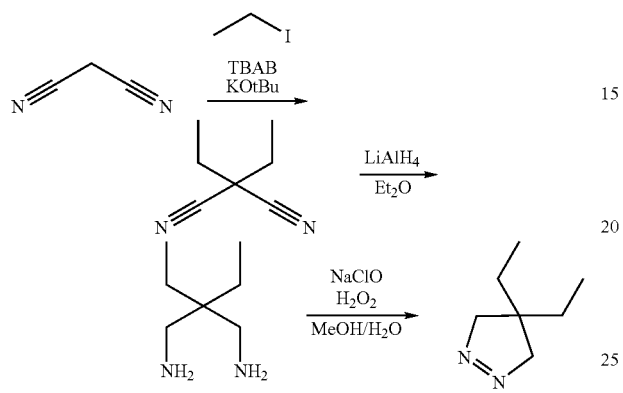

2,2-Diethyl-malononitrile

Malononitrile (15.2 g) was mixed with TBAB (3.0 g, 4 mol %) and ethyl iodide (36.8 mL, 2 equiv.). After stirring for 30 minutes at room temperature, the mixture was cooled in an ice bath, KOtBu (51.6 g, 2 equiv.) was added portionwise, the ice bath was removed, and the mixture was stirred for 30 minutes at room temperature. Extraction with $DCM/H_2O$, drying over $Na_2SO_4$ and evaporation under reduced pressure gave 40 grams of crude material, which was purified by flash chromatography eluting with DCM. This yielded 20.4 grams of an orange oil which solidified upon standing. $^1$H NMR (400 MHz, $CDCl_3$) δ 1.29 (t, J=7.5 Hz, 6H), 2.00 (q, J=7.5 Hz, 4H).

2,2-Diethyl-propane-1,3-diamine

A suspension of $LiAlH_4$ (4.66 g) in dry $Et_2O$ (100 mL) was cooled in an ice bath, and a solution of 2,2-diethyl-malononitrile (5.0 g) in $Et_2O$ (50 mL) was added dropwise at such a rate that the temperature was kept below 20° C. The mixture was stirred overnight at room temperature, cooled in an ice bath, and quenched by adding $H_2O$ (5 mL), 2M aqueous NaOH (10 mL) and again $H_2O$ (5 mL). The suspension was filtered, the filter cake was washed with $Et_2O$, and the combined filtrates were evaporated to dryness under reduced pressure to give 5.0 g of a clear, light-yellow liquid. $^1$H NMR (400 MHz, $CDCl_3$) δ 0.80 (t, J=8 Hz, 6H), 1.08 (br s, 4H), 1.22 (q, J=8 Hz, 4H), 2.52 (s, 4H).

4,4-Diethyl-4,5-dihydro-3H-pyrazole 2,2-Diethyl-propane-1,3-diamine (5.0 g) was taken up in a mixture of $H_2O$ (40 mL) and MeOH (10 mL), and cooled in an ice bath. Simultaneously, $H_2O_2$ (24.2 mL of a 30% solution, 6 equiv.) and NaClO (54.9 mL of a 10% solution, 2.4 equiv.) were added dropwise, the ice bath was removed, and the mixture was stirred for 2 h. at room temperature. Extraction with DCM, drying over $Na_2SO_4$ and evaporation under reduced pressure yielded 3.51 g of a clear, yellow liquid containing 77% of the anticipated product and 23% of the diamine starting material. This material was used in subsequent steps without further purification. $^1$H NMR (400 MHz, $CDCl_3$) δ 0.78 (t, J=7.5 Hz, 6H), 1.36 (q, J=7.5 Hz, 4H), 4.14 (s, 4H).

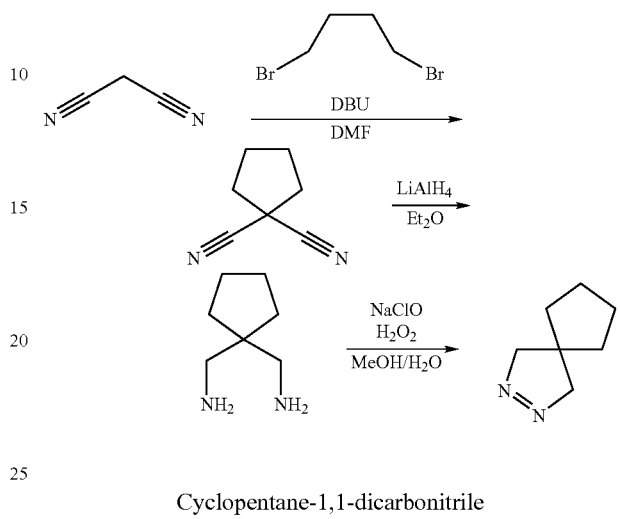

Cyclopentane-1,1-dicarbonitrile

Malononitrile (15.0 g) was dissolved in dry DMF (200 mL) and cooled in an ice bath. Subsequently, DBU (75 mL, 2.2. equiv.) and 1,4-dibromobutane (29.6 mL, 1.1 equiv.) were added dropwise. The ice bath was removed, an extra 100 mL of dry DMF was added, and the mixture was stirred at 80° C. for 2 h. After cooling to ambient temperature, DCM was added and the mixture was washed 5 times with 5% aqueous $NaHCO_3$. The organic phase was dried over $Na_2SO_4$ and evaporated under reduced pressure to give 40 g of a black oily substance. This was purified by flash chromatography eluting with PA:EA 9:1 ($R_f$=0.35, visualized with $I_2$) to give 23.4 g of a colorless liquid. $^1$H NMR (400 MHz, $CDCl_3$) δ 1.94-2.03 (m, 4H), 2.41 (t, J=7 Hz, 4H).

C-(1-Aminomethyl-cyclopentyl)-methylamine

A suspension of $LiAlH_4$ (4.74 g) in dry $Et_2O$ (100 mL) was cooled in an ice bath, and a solution of cyclopentane-1,1-dicarbonitrile (5.0 g) in $Et_2O$ (50 mL) was added dropwise at such a rate that the temperature was kept below 20° C. The mixture was stirred overnight at room temperature, cooled in an ice bath, and quenched by adding $H_2O$ (5 mL), 2M aqueous NaOH (10 mL) and again $H_2O$ (5 mL). The suspension was filtered, the filter cake was washed with $Et_2O$, and the combined filtrates were evaporated to dryness under reduced pressure to give 4.95 g of a clear, colorless liquid. $^1$H NMR (400 MHz, $CDCl_3$) δ 1.24 (br s, 4H), 1.22-1.40 (m, 4H), 1.55-1.64 (m, 4H), 2.62 (s, 4H).

2,3-Diaza-spiro[4.4]non-2-ene

C-(1-Aminomethyl-cyclopentyl)-methylamine (4.87 g) was taken up in a mixture of $H_2O$ (40 mL) and MeOH (10 mL), and cooled in an ice bath. Simultaneously, $H_2O_2$ (23.9 mL of a 30% solution, 6 equiv.) and NaClO (54.3 mL of a 10% solution, 2.4 equiv.) were added dropwise, the ice bath was removed, and the mixture was stirred for 2 h. at room temperature. Extraction with DCM, drying over $Na_2SO_4$ and evaporation under reduced pressure yielded 3.74 g of a clear, light-yellow liquid containing 90% of the anticipated product and 10% of the diamine starting material. This material was used in subsequent steps without further purification. $^1$H NMR (400 MHz, CDCl$_3$) δ 1.48-1.57 (m, 4H), 1.62-1.69 (m, 4H), 4.26 (s, 4H).

light-yellow liquid. $^1$H NMR (400 MHz, CDCl$_3$) δ 1.24-1.53 (m, 10H), 4.17 (s, 4H).

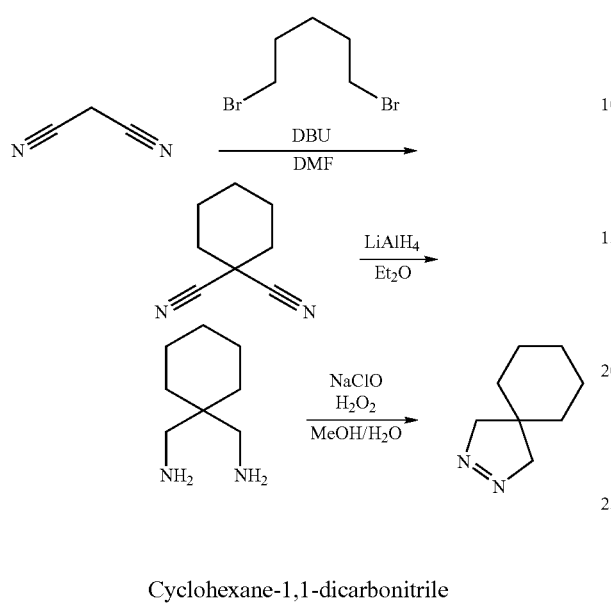
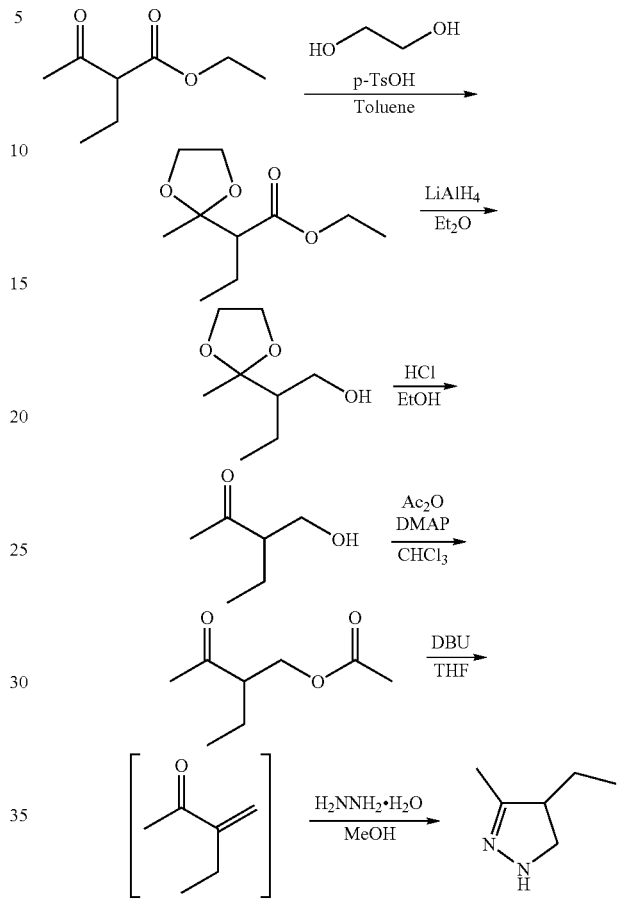

Cyclohexane-1,1-dicarbonitrile

Malononitril (15.0 g) was dissolved in dry DMF (200 mL). Subsequently, DBU (75 mL) and 1,5-dibromopentane (34 mL) were added at 0° C. (ice bath). The ice bath was removed and the reaction was stirred for 2 h at 80° C. After cooling down, the reaction was poured into DCM. The organic layer was washed several times with 5% NaHCO$_3$, the organic layer dried over Na$_2$SO$_4$ and the solvent evaporated under reduced pressure. The crude product was purified by flash chromatography eluting with PA:EtOAc (9:1) yielding 25.7 g white crystals. $^1$H NMR (400 MHz, CDCl$_3$) δ 1.48-1.61 (m, 2H), 1.68-1.84 (m, 4H), 2.13 (t, J=6 Hz, 4H).

C-(1-Aminomethyl-cyclohexyl)-methylamine

Cyclohexane-1,1-dicarbonitrile (20.0 g) was taken up in dry Et$_2$O (70 mL). This mixture was added dropwise to a suspension of LiAlH$_4$ (17.0 g) in dry Et$_2$O (250 mL) cooled in an ice bath. The mixture was stirred overnight at room temperature, cooled in an ice bath, and quenched by adding H$_2$O (17.0 mL), 2M aqueous NaOH (34.0 mL) and again H$_2$O (17 mL). The suspension was filtered, the filter cake was washed with Et$_2$O, and the combined filtrates were evaporated to dryness yielding 20.8 g of a clear, colorless liquid. $^1$H NMR (400 MHz, CDCl$_3$) δ 1.05-1.55 (m, 14H), 2.61 (s, 4H).

2,3-Diaza-spiro[4.5]dec-2-ene

C-(1-Aminomethyl-cyclohexyl)-methylamine (10.0 g) was taken up in a mixture of H$_2$O (40 mL) and MeOH (10 mL), and cooled in an ice bath. Simultaneously, H$_2$O$_2$ (44.3 mL of a 30% solution, 6 equiv.) and NaClO (125.5 mL of a 10% solution, 2.4 equiv.) were added dropwise, the ice bath was removed, and the mixture was stirred for 45 min. at room temperature. Extraction with DCM, drying over Na$_2$SO$_4$ and evaporation under reduced pressure, yielded 8.7 g of a clear, 2-(2-Methyl-[1,3]dioxolan-2-yl)-butyric acid ethyl ester Methyl-2-ethylacetoacetate (100 mL) was taken up in toluene (250 mL). Ethylene glycol (46.9 mL, 1.35 equiv.) and a catalytic amount of p-TsOH.H$_2$O were added, and the mixture was refluxed overnight under Dean-Stark conditions. After cooling to ambient temperature, the mixture was washed with 5% aqueous NaHCO$_3$ and saturated aqueous NaCl, the organic phase was dried over Na$_2$SO$_4$ and evaporated under reduced pressure. The residue was purified by repeated vacuum distillation (118-128° C., 15 mbar), yielding 85.5 g of product. $^1$H NMR (400 MHz, CDCl$_3$) δ 0.90 (t, J=7 Hz, 3H), 1.28 (t, J=7 Hz, 3H), 1.40 (s, 3H), 1.59-1.83 (m, 2H), 2.56 (dd, J=11.5 and 4 Hz, 1H), 3.90-4.06 (m, 4H), 4.18 (m, 2H).

2-(2-Methyl-[1,3]-dioxolan-2-yl)-butan-1-ol 2-(2-Methyl-[1,3]dioxolan-2-yl)-butyric acid ethyl ester (85.5 g) was taken up in dry Et$_2$O (50 mL). This mixture was added dropwise to a suspension of LiAlH$_4$ (16.1 g) in dry Et$_2$O (200 mL), cooled in an ice bath. The mixture was refluxed for 4 h., cooled in an ice bath, and quenched by adding H$_2$O (16.1 mL), 2M aqueous NaOH (32.2 mL) and again H$_2$O (16.1 mL). The suspension was filtered, the filter cake was washed with Et$_2$O, and the combined filtrates were evaporated to dryness. The residue (49 g) was purified by vacuum distillation (112-125° C., 15 mbar), yielding 43.5 g of a clear, colorless liquid. $^1$H NMR (400 MHz, CDCl$_3$) δ 0.98 (t, J=7.5 Hz, 3H), 1.10-1.24 (m, 1H), 1.31 (s, 3H), 1.50-1.75 (m, 2H), 3.12, (br s, 1H), 3.59-3.76 (m, 2H), 3.94-4.02 (m, 4H).

3-Hydroxymethyl-pentan-2-one 2-(2-Methyl-[1,3]dioxolan-2-yl)-butan-1-ol (43.5 g) was taken up in a mixture of H$_2$O (100 mL) and EtOH (10 mL), and concentrated aqueous HCl (1 mL) was added. The mixture was refluxed for 2 h., cooled to ambient temperature, neutralized with 2M aqueous NaOH, saturated with ammonium sulfate and extracted twice with Et$_2$O. The combined organic layers were dried over Na$_2$SO$_4$ and evaporated to dryness. The yellowish residue (25.7 g) was purified by vacuum distillation to give 20.7 g of a clear, colorless oil. $^1$H NMR (400 MHz, CDCl$_3$) δ 0.95 (t, J=7.5 Hz, 3H), 1.49-1.76 (m, 2H), 2.21 (s, 3H), 2.64 (m, 1H), 3.68-3.84 (m, 3H).

Acetic acid 2-ethyl-3-oxo-butyl ester

3-Hydroxymethyl-pentan-2-one (20.7 g) was dissolved in CHCl$_3$ (150 mL) and cooled in an ice bath. Acetic anhydride (80 mL) was added, followed by DMAP (2.18 g), and the mixture was stirred overnight at room temperature. After cooling in an ice bath, MeOH (120 mL) was added dropwise, and the mixture was poured into a saturated aqueous NaHCO$_3$ solution. After extraction with DCM twice, the combined organic phases were dried over Na$_2$SO$_4$ and evaporated under reduced pressure to give 28.0 g of a light-yellow liquid. $^1$H NMR (400 MHz, CDCl$_3$) δ 0.93 (t, J=8 Hz, 3H), 1.46-1.75 (m, 2H), 2.03 (s, 3H), 2.20 (s, 3H), 2.77 (quint., J=6.5 Hz, 1H), 4.20 (d, J=7 Hz, 3H).

4-Ethyl-3-methyl-4,5-dihydro-1H-pyrazole

Acetic acid 2-ethyl-3-oxo-butyl ester (23.0 g) was taken up in dry THF (75 mL) and DBS (23.9 mL) was added. The mixture was stirred at room temperature for 15 min. to form the intermediate 3-methylene-pentan-2-one. MeOH (75 mL) was added, followed by dropwise addition of hydrazine hydrate (7.75 mL). The resulting mixture was stirred overnight at room temperature and evaporated under reduced pressure. The residue was purified by vacuum distillation (94-106° C., 15 mbar), yielding 7.9 g of a clear, colorless liquid. $^1$H NMR (400 MHz, CDCl$_3$) δ 0.95 (t, J=7.5 Hz, 3H), 1.33-1.83 (m, 2H), 1.92 (s, 3H), 2.78 (m, 1H), 3.01 (t, J=9.5 Hz, 1H), 3.51 (t, J=9.5 Hz, 1H).

2-Dimethylaminomethyl-cyclohexanone

To cyclohexanone (259 mL) was added formaldehyde (37.2 mL of a 37% aqueous solution) and dimethylamine hydrochloride (40.8 g). The stirred mixture was slowly heated and refluxed for 1 h. After cooling to ambient temperature H$_2$O was added, and the mixture was extracted twice with Et$_2$O. The aqueous layer was made basic by addition of 50% aqueous NaOH (27.5 mL), and subsequently extracted twice with DCM. The combined organic phases were dried over Na$_2$SO$_4$ and evaporated under reduced pressure to give 66.6 g of a light-yellow liquid. $^1$H NMR (400 MHz, CDCl$_3$) δ 1.34-1.47 (m, 1H), 1.60-1.78 (m, 2H), 1.81-1.92 (m, 1H), 1.98-2.09 (m, 1H), 2.16-2.55 (m, 5H), 2.21 (s, 6H), 2.69 (dd, J=13 and 6 Hz, 1H).

3,3a,4,5,6,7-Hexahydro-2H-indazole

Hydrazine hydrate (28.0 mL) was dissolved in n-BuOH (200 mL) and cooled in an ice bath. A solution of 2-dimethylaminomethyl-cyclohexanone (64.0 g) in n-BuOH (50 mL) was added dropwise, the mixture was slowly warmed and refluxed for 20 hours. The solvent was evaporated under reduced pressure.

The residue was purified by vacuum distillation (64-67° C., 28 Pa), yielding 24.2 g of a clear, colorless liquid. This material was used in subsequent steps without further purification.

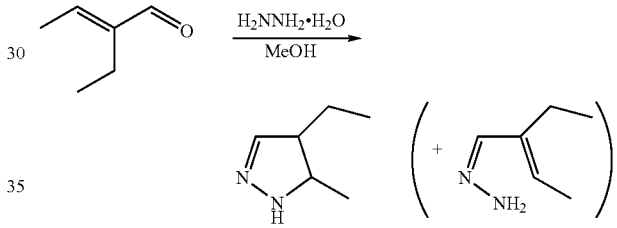

4-Ethyl-5-methyl-4,5-dihydro-1H-pyrazole

Hydrazine hydrate (12.4 mL) was dissolved in MeOH (100 mL) and cooled in an ice bath. To this mixture, a solution of 2-ethyl-but-2-enal (25 g) in MeOH (50 mL) was added at such a rate that the temperature was kept below 10° C. The ice bath was removed and the mixture was stirred at room temperature for 2 days. The solvent was evaporated under reduced pressure. Vacuum distillation (90-100° C., 20 mbar) yielded 16.9 g of a light-yellow liquid containing the desired product as a diastereomeric mixture and the hydrazone in approximately a 1:2 ratio. This material was used in subsequent steps without further purification.

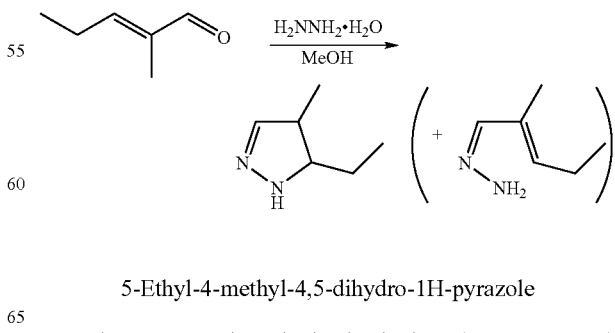

5-Ethyl-4-methyl-4,5-dihydro-1H-pyrazole

Under N$_2$ atmosphere, hydrazine hydrate (63.9 mL, 10 eq) was dissolved in MeOH (100 mL) and cooled in an ice bath.

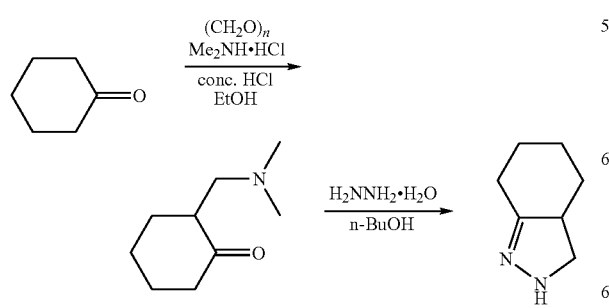

To this mixture, a solution of 2-methyl-pent-2-enal (15.0 mL) in MeOH (50 mL) was added at such a rate that the temperature was kept below 10° C. The ice bath was removed and the mixture was stirred at room temperature overnight. The solvent was evaporated under reduced pressure. Vacuum distillation (40-45° C., 15 mbar) yielded 9.5 g of a light-yellow liquid containing the desired product as a diastereomeric mixture and the hydrazone in approximately a 1:1 ratio. This material was used in subsequent steps without further purification.

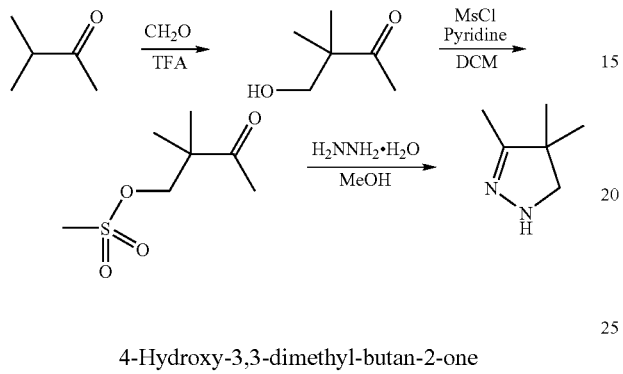

4-Hydroxy-3,3-dimethyl-butan-2-one

To 25 mL 3-methyl-butan-2-one was added 7.01 g paraformaldehyde and 36.0 mL trifluoroacetic acid. The mixture was refluxed for 7 hours. After cooling down, 300 mL $H_2O$ and 100 g (5 eq) $NaHCO_3$ were added. The suspension was filtered and the organic layer was separated. The filter cake was washed two times with DCM, the combined filtrates were dried over $Na_2SO_4$ and the solvent was evaporated under reduced pressure to give 23.7 g of an orange liquid. $^1$H NMR (400 MHz, $CDCl_3$) δ 1.17 (s, 6H), 2.17 (s, 3H), 2.38 (t, J=7 Hz, 1H), 3.65 (d, J=7 Hz, 2H).

Methanesulfonic acid 2,2-dimethyl-3-oxo-butyl ester 23.7 g 4-Hydroxy-3,3-dimethyl-butan-2-one was dissolved in 150 ml. DCM. 49.5 mL (3 eq) pyridine and 17.5 mL (1.1 eq) mesylchloride were added and the mixture was stirred at room temperature for 20 hours. The suspension was filtered and the filter cake was washed two times with DCM. The filtrate was washed with 1 M HCl and the aqueous layer was extracted two times with DCM. The combined filtrates were dried over $Na_2SO_4$ and the solvent was evaporated under reduced pressure to give 41.2 g of a brown liquid. $^1$H NMR (400 MHz, $CDCl_3$) δ 1.24 (s, 6H), 2.20 (s, 3H), 3.03 (s, 3H), 4.21 (s, 2H).

3,4,4-Trimethyl-4,5-dihydro-1H-pyrazole 39.2 g Methanesulfonic acid 2,2-dimethyl-3-oxo-butyl ester was dissolved in 200 mL MeOH and cooled in an ice bath. 21.6 mL (2.2 eq) hydrazine hydrate was added dropwise and the reaction mixture was stirred at room temperature for 1 hour. The reaction mixture was concentrated, 5% $NaHCO_3$ was added and extracted 3 times with DCM. The combined organic layers were dried over $Na_2SO_4$ and the solvent was evaporated under reduced pressure to give 19.5 g of an orange liquid. Vacuum distillation of 10 g of this liquid yielded 6.4 g light-yellow liquid (76-78° C., 20 mbar). $^1$H NMR (400 MHz, $CDCl_3$) δ 1.14 (s, 6H), 1.86 (s, 3H), 3.14 (s, 2H), 4.00 (br s, 1H).

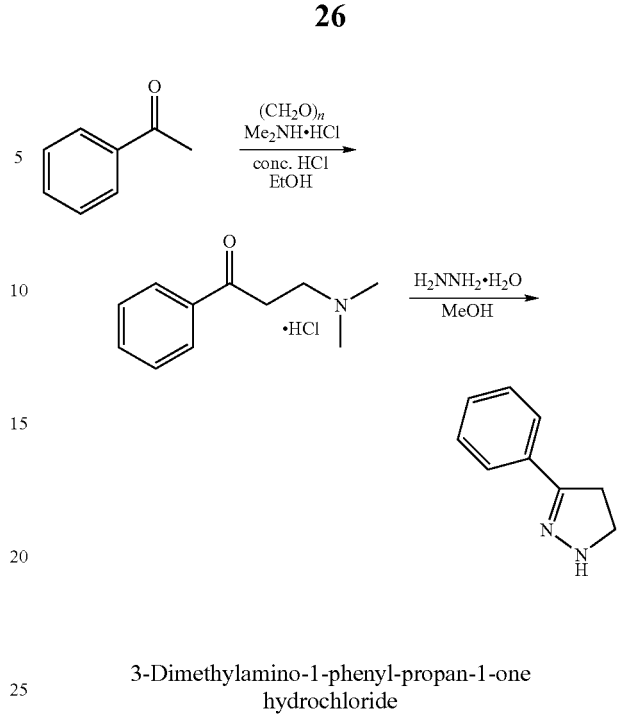

3-Dimethylamino-1-phenyl-propan-1-one hydrochloride

To a solution of 0.5 mL concentrated aqueous HCl in 40 mL EtOH, acetophenone (30.0 g), paraformaldehyde (10.0 g) and dimethylamine hydrochloride (26.5 g) were added and the mixture was refluxed for 3 h. The mixture was cooled to room temperature, and the precipitate was filtered, washed with acetone and dried in vacuo to obtain 37.2 g of white crystalline material. $^1$H NMR (200 MHz, DMSO-$d_6$) δ 2.84 (s, 6H), 3.38-3.55 (m, 2H), 3.57-3.74 (m, 2H), 7.48-7.73 (m, 3H), 7.97-8.10 (m, 2H).

3-Phenyl-4,5-dihydro-1H-pyrazole

Under $N_2$ atmosphere, 3-dimethylamino-1-phenyl-propan-1-one hydrochloride (37.2 g) was dissolved in warm MeOH (75 mL), and slowly added to a solution of hydrazine hydrate (23 mL) and 50% aqueous NaOH (12 mL) in MeOH (30 mL) stirred at 50° C. The mixture was refluxed for 2 hours and evaporated under reduced pressure. Ice water was added to the residue and after stirring for 5 minutes the formed solid was filtered off. The residue was taken up in $Et_2O$, dried over $Na_2SO_4$, and evaporated to dryness under reduced pressure to give 19.7 g of a yellow oil being 80% pure, which was used in subsequent steps without further purification.

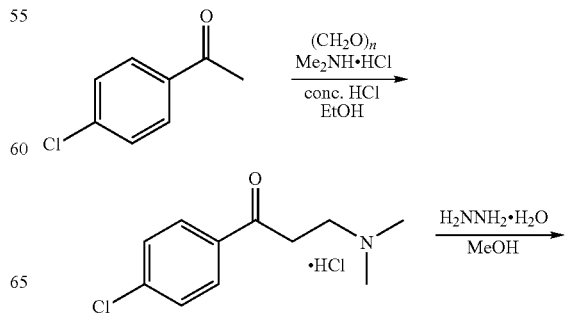

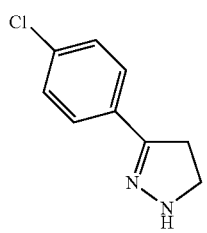

1-(4-Chloro-phenyl)-3-dimethylamino-propan-1-one hydrochloride

To EtOH (80 mL), p-chloroacetophenone (77.3 g, 0.50 mol), dimethylamine hydrochloride (52.7 g, 0.65 mol), paraformaldehyde (19.8 g, 0.66 mol) and concentrated aqueous HCl (1 mL) were added and the mixture was refluxed for 5 h. The mixture was cooled to 40° C., acetone (400 mL) was added, and under stirring the mixture was cooled further to 20° C. The precipitate was filtered, washed with acetone and PA, and air dried to obtain 69.5 g of product which was used without further purification in the subsequent step.

3-(4-Chloro-phenyl)-4,5-dihydro-1H-pyrazole

Under $N_2$ atmosphere, 1-(4-chloro-phenyl)-3-dimethylamino-propan-1-one hydrochloride (37.2 g) was dissolved in warm MeOH (75 mL), and slowly added to a solution of hydrazine hydrate (23 mL) and 50% aqueous NaOH (12 mL) in MeOH (30 mL) stirred at 50° C. The mixture was refluxed for 2 hours, and evaporated under reduced pressure. Water was added to the residue, followed by extraction with DCM. The organic phase was washed twice with water, dried and evaporated under reduced pressure, to give 25.0 g of a yellow solid, m.p. 90-100° C.

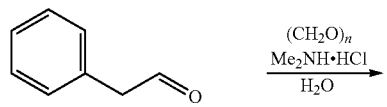

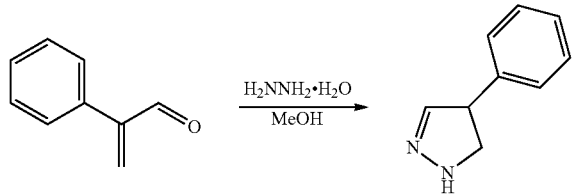

4-Phenyl-4,5-dihydro-1H-pyrazole

Under $N_2$ atmosphere, dimethylamine hydrochloride (7.27 g) and formaline (37%) (6.63 mL) were added to phenyl acetaldehyde (10 mL) and stirred overnight at room temperature. The reaction mixture was extracted once with diethyl ether, the organic layer was dried over $MgSO_4$ and the solution containing the intermediate 2-phenyl-propenal was taken up in MeOH. Hydrazine hydrate (7.87 mL) was added, and the reaction mixture was stirred for 2 hours at 50° C. ($Et_2O$ evaporated). The mixture was concentrated under reduced pressure. The residue was dissolved in DCM and dried over $MgSO_4$, followed by evaporation under reduced pressure, yielding 3.12 g of a yellow oil which was used in the subsequent step without further purification.

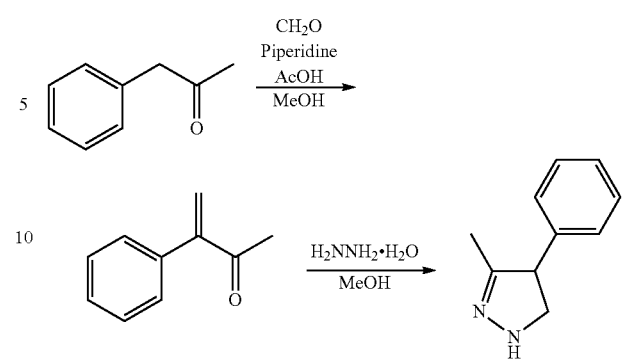

3-Phenyl-but-3-en-2-one

1-Phenyl-propan-2-one (40.8 g) was dissolved in 200 ml of MeOH. Formaline (37%) (79 mL), piperidine (4 ml) and HOAc (4 ml) where added and de reaction was stirred for 3 h at 60° C. The reaction mixture was evaporated to dryness under reduced pressure. The residue was taken up in diethyl ether, and extracted with water. The organic layer was washed with 1M HCl, dried over $MgSO_4$ and evaporated under reduced pressure to yield 36.3 g of a yellow liquid. $^1$H NMR (400 MHz, $CDCl_3$) δ 2.41 (s, 3H), 5.87 (s, 1H), 6.18 (s, 1H), 7.24-7.40 (m, 5H).

3-Methyl-4-phenyl-4,5-dihydro-1H-pyrazole

Hydrazine hydrate (12.06 mL) was added to 3-Phenyl-but-3-en-2-one (36.3 g) in MeOH (200 mL). The reaction was stirred overnight at reflux temperature. The solvent was evaporated under reduced pressure. The residue was taken up in diethyl ether and washed with water. The organic phase was dried over $Na_2SO_4$ and evaporated under reduced pressure. The crude material was purified by flash column chromatography eluting with DCM:MeOH=98:2 to give 19.7 g of a orange oil, containing 65% of the desired product, which was used in subsequent steps without further purification.

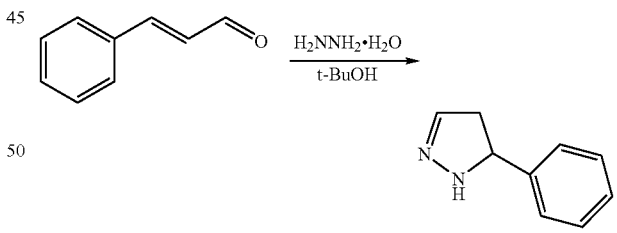

5-Phenyl-4,5-dihydro-1H-pyrazole

Under $N_2$ atmosphere, hydrazine hydrate (9.2 mL) was added to a solution of cinnamaldehyde (10.0 g) in t-BuOH (20 mL). The mixture was refluxed overnight, followed by concentration under reduced pressure. Water was added to the residue, and the aqueous phase was extracted twice with DCM. The combined organic layers were washed with water, dried over $Na_2SO_4$ and concentrated under reduced pressure. This gave 10.46 g of a yellow oil containing 85% of the desired product, which was used in subsequent steps without further purification. $^1$H NMR (200 MHz, $CDCl_3$) δ 2.61-2.80

(m, 1H), 3.04-3.23 (m, 1H), 4.72 (dd, J=8 and 10 Hz, 1H), 5.60-6.10 (br s, 1H), 6.77-6.87 (m, 1H), 7.18-7.47 (m, 5H).

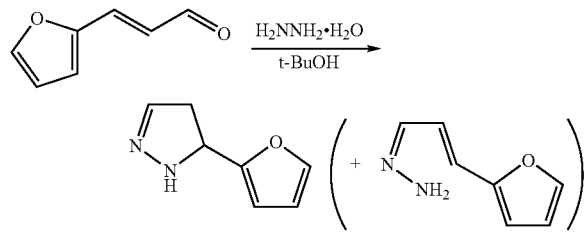

5-Furan-2-yl-4,5-dihydro-1H-pyrazole

Under N₂ atmosphere, hydrazine hydrate (4.0 mL) was added to a solution of 3-(2-furyl)acrolein (5.0 g) in t-BuOH (25 mL). The mixture was refluxed for 2 days, followed by evaporation under reduced pressure. The residue was taken up in DCM and extracted twice with 5% aqueous NaHCO₃. The organic phase was dried over Na₂SO₄ and evaporated under reduced pressure. This gave 5.3 g of a yellow oil, containing 45% of the anticipated product and 55% of the hydrazone intermediate that failed to undergo ring-closure. Additional 24 h reflux in n-BuOH gave (after workup) 5.6 g of a brown oil, containing 58% of the anticipated product and 42% of the hydrazone. This material was used in subsequent steps without further purification. Characteristic pyrazoline signals in ¹H NMR (400 MHz, CDCl₃): δ 2.87-3.08 (m, 2H), 4.72-4.81 (m, 1H), 6.87 (br s, 1H).

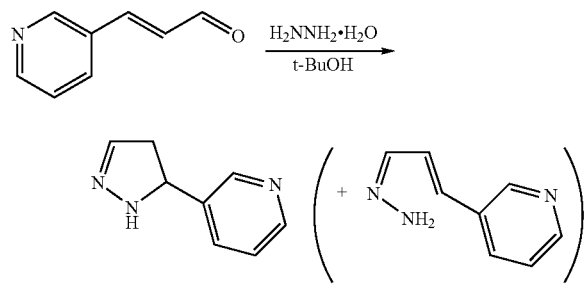

3-(3,4-Dihydro-2H-pyrazol-3-yl)-pyridine

Under N₂ atmosphere, hydrazine hydrate (3.65 mL, 2 equiv.) was added to a solution of 3-(3-pyridyl)acrolein (5.0 g) in t-BuOH (25 mL). The mixture was refluxed for 3 days, followed by evaporation under reduced pressure. The residue was taken up in DCM and washed with 5% aqueous NaHCO₃. The organic phase was dried over Na₂SO₄ and evaporated under reduced pressure. This gave 5.0 g of a red oil, containing 74% of the anticipated product and 26% of the hydrazone intermediate that failed to undergo ring-closure. This material was used in subsequent steps without further purification. Characteristic pyrazoline signals in ¹H NMR (400 MHz, CDCl₃): δ 2.63-2.75 (m, 1H), 3.13-3.25 (m, 1H), 4.72-4.82 (m, 1H), 6.85 (br s, 1H).

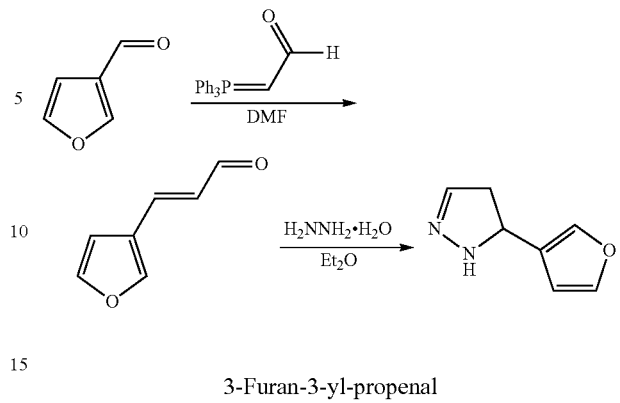

3-Furan-3-yl-propenal 6.08 g (triphenylphosphoranylidene)acetaldehyde was suspended in 10 mL dry DMF. Added was 1.67 mL (1 equiv.) 3-furaldehyde and the mixture was stirred overnight at 80° C. The mixture was taken up in EA and washed 4 times with 5% aqueous NaHCO₃, the organic phase was dried over Na₂SO₄, filtrated and concentrated in vacuo. The residue was suspended in PA, filtrated and concentrated in vacuo to yield 1.47 g of a light brown oil containing 68% of the desired product. This material was used in subsequent steps without further purification. Characteristic signals in ¹H NMR (400 MHz, CDCl₃): δ 6.45 (dd, J=8 and 16 Hz, 1H), 9.63 (d, J=8 Hz, 1H).

5-Furan-3-yl-4,5-dihydro-1H-pyrazole 5.84 ml (10 equiv.) hydrazine hydrate was added to 20 mL diethylether. The emulsion was cooled with an ice/NaCl bath to −10° C. A solution of 1.47 g 3-furan-3-yl-propenal in 20 mL diethylether was added dropwise. The mixture was stirred overnight (with ice bath) and allowed to slowly reach room temperature. 5% aqueous NaHCO₃ was added and the mixture was extracted 3 times with EA. The combined organic layers were dried over Na₂SO₄, filtrated and concentrated in vacuo. The residue was caught on an SCX ion exchange column, washed with MeOH and eluted with 1M NH₃ in MeOH to yield 950 mg of an orange oil containing 85% of the desired product after evaporation. This material was used in subsequent steps without further purification. ¹H NMR (400 MHz, CDCl₃) δ 2.62-2.72 (m, 1H), 2.97-3.07 (m, 1H), 4.62-4.71 (m, 1H), 5.57-5.74 (br s, 1H), 6.36 (br s, 1H), 6.87 (br s, 1H), 7.35-7.41 (m, 2H).

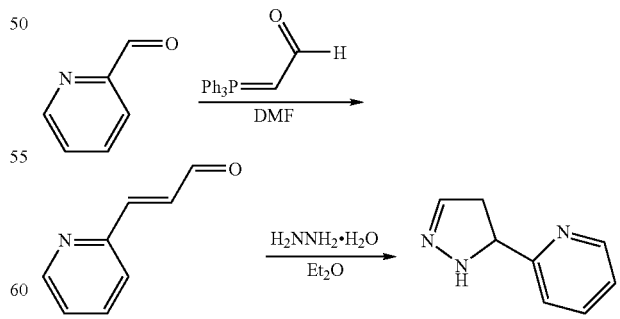

3-Pyridin-2-yl-propenal 6.08 g (triphenylphosphoranylidene)acetaldehyde was suspended in 10 mL dry DMF. Added was 1.90 mL (1 equiv.)

pyridine-2-carbaldehyde and the mixture was stirred overnight at room temperature. The mixture was taken up in EA and washed 4 times with 5% aqueous NaHCO₃, the organic phase was dried over Na₂SO₄, filtrated and concentrated in vacuo. The residue was suspended in PA, filtrated and concentrated in vacuo to yield 1.50 g of a dark yellow oil containing 80% of the desired product. This material was used in subsequent steps without further purification. ¹H NMR (400 MHz, CDCl₃) δ 7.09 (dd, J=8 and 16 Hz, 1H), 7.30-7.36 (m, 1H), 7.49-7.59 (m, 2H), 7.77 (dt, J=8, 8 and 2 Hz, 1H), 8.67-8.74 (m, 1H), 9.81 (d, J=8 Hz, 1H).

2-(3,4-Dihydro-2H-pyrazol-3-yl)-pyridine 4.56 ml (10 equiv.) hydrazine hydrate was added to 20 mL diethylether. The emulsion was cooled with an ice/NaCl bath to −10° C. A solution of 1.25 g 3-pyridin-2-yl-propenal in 20 mL diethylether was added dropwise. The mixture was stirred overnight (with ice bath) and allowed to slowly reach room temperature. 5% aqueous NaHCO₃ was added and extracted 5 times with EA. The combined organic layers were dried over Na₂SO₄, filtrated and concentrated in vacuo. The residue was caught on an SCX ion exchange column, washed with MeOH and eluted with 1M NH₃ in MeOH to yield 1.28 g of a brown oil containing 90% of the desired product. This material was used in subsequent steps without further purification. ¹H NMR (400 MHz, CDCl₃) δ 2.84-2.94 (m, 1H), 3.19-3.29 (m, 1H), 4.82-4.90 (m, 1H), 6.83 (br s, 1H), 7.17-7.23 (m, 1H), 7.35-7.40 (m, 1H), 7.69 (dt, J=7.5, 7.5 and 2 Hz, 1H), 8.53-8.58 (m, 1H).

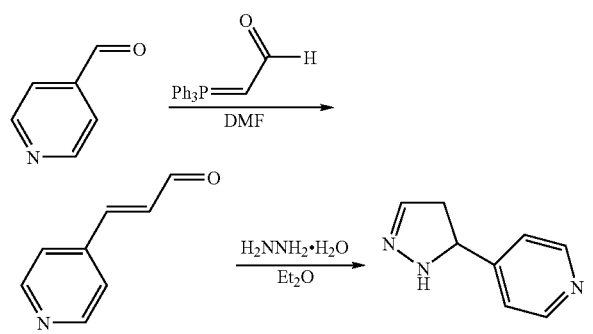

3-Pyridin-4-yl-propenal 6.08 g (triphenylphosphoranylidene)acetaldehyde was suspended in 10 mL dry DMF. Added was 1.93 mL (1 equiv.) pyridine-4-carbaldehyde and the mixture was stirred overnight at room temperature. The mixture was taken up in EA and washed 4 times with 5% aqueous NaHCO₃, the organic phase was dried over Na₂SO₄, filtrated and concentrated in vacuo. The residue was suspended in PA, filtrated and concentrated in vacuo to yield 1.17 g of a yellow oil containing 80% of the desired product. This material was used in subsequent steps without further purification. ¹H NMR (400 MHz, CDCl₃) δ 6.85 (dd, J=8 and 16 Hz, 1H), 7.39-7.47 (m, 3H), 8.70-8.74 (m, 2H), 9.78 (d, J=8 Hz, 1H).

4-(3,4-Dihydro-2H-pyrazol-3-yl)-pyridine 4.27 ml (10 equiv.) hydrazine hydrate was added to 20 mL diethylether. The emulsion was cooled with an ice/NaCl bath to −10° C. A solution of 1.17 g 3-pyridin-4-yl-propenal in 20 mL diethylether was added dropwise. The mixture was stirred overnight (with ice bath) and allowed to slowly reach room temperature. 5% aqueous NaHCO₃ was added and extracted 5 times with EA. The combined organic layers were dried over Na₂SO₄, filtrated and concentrated in vacuo. The residue was caught on an SCX ion exchange column, washed with MeOH and eluted with 1M NH₃ in MeOH to yield 1.23 g of a brown oil containing 90% of the desired product. This material was used in subsequent steps without further purification. ¹H NMR (400 MHz, CDCl₃) δ 2.61-2.71 (m, 1H), 3.15-3.25 (m, 1H), 4.68-4.76 (m, 1H), 6.82 (br s, 1H), 7.25-7.30 (m, 2H), 8.55-8.60 (m, 2H).

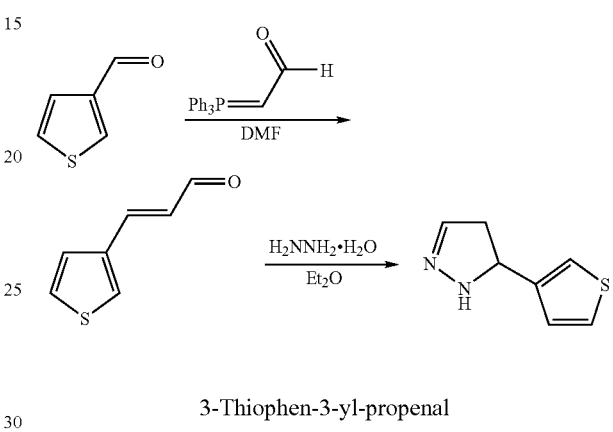

3-Thiophen-3-yl-propenal 10.0 g (triphenylphosphoranylidene)acetaldehyde was suspended in 10 mL dry DMF. Added was 2.88 mL (1 equiv.) thiophene-3-carbaldehyde and the mixture was stirred overnight at 80° C. The mixture was taken up in EA and washed 4 times with 5% aqueous NaHCO₃, the organic phase was dried over Na₂SO₄, filtrated and concentrated in vacuo. The residue was suspended in PA, filtrated and concentrated in vacuo to yield 4.16 g of an orange oil containing 54% of the desired product. This material was used in subsequent steps without further purification. Characteristic signals in ¹H NMR (400 MHz, CDCl₃): δ 6.54 (dd, J=8 and 16 Hz, 1H), 9.66 (d, J=8 Hz, 1H).

5-Thiophen-3-yl-4,5-dihydro-1H-pyrazole 14.6 ml (10 equiv.) hydrazine hydrate was added to 50 mL diethylether. The emulsion was cooled with an ice/NaCl bath to −10° C. A solution of 4.16 g 3-thiophen-3-yl-propenal in 25 mL diethylether was added dropwise. The mixture was stirred overnight (with ice bath) and allowed to slowly reach room temperature. 5% aqueous NaHCO₃ was added and extracted 3 times with EA. The combined organic layers were dried over Na₂SO₄, filtrated and concentrated in vacuo to yield 4.12 g of an orange oil containing 70% of the desired product. This material was used in subsequent steps without further purification. Characteristic pyrazoline signals in ¹H NMR (400 MHz, CDCl₃): δ 2.78-2.88 (m, 1H), 3.03-3.13 (m, 1H), 4.77-4.86 (m, 1H), 6.86 (br s, 1H).

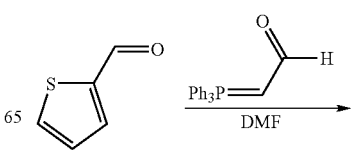

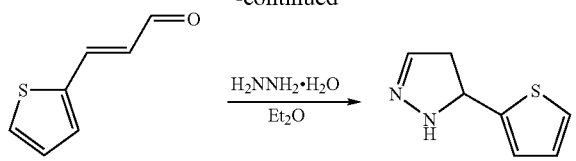

3-Thiophen-2-yl-propenal 10.0 g (triphenylphosphoranylidene)acetaldehyde was suspended in 10 mL dry DMF. Added was 3.07 mL (1 equiv.) thiophene-2-carbaldehyde and the mixture was stirred overnight at 80° C. The mixture was taken up in EA and washed 4 times with 5% aqueous NaHCO$_3$, the organic phase was dried over Na$_2$SO$_4$, filtrated and concentrated in vacuo. The residue was suspended in PA, filtrated and concentrated in vacuo to yield 4.27 g of an orange oil containing 50% of the desired product. This material was used in subsequent steps without further purification. Characteristic signals in $^1$H NMR (400 MHz, CDCl$_3$): δ 6.52 (dd, J=8 and 16 Hz, 1H), 9.63 (d, J=8 Hz, 1H).

5-Thiophen-2-yl-4,5-dihydro-1H-pyrazole 15.0 ml (10 equiv.) hydrazine hydrate was added to 50 mL diethylether. The emulsion was cooled with an ice/NaCl bath to −10° C. A solution of 4.27 g 3-thiophen-2-yl-propenal in 25 mL diethylether was added dropwise. The mixture was stirred overnight (with ice bath) and allowed to slowly reach room temperature. 5% aqueous NaHCO$_3$ was added and extracted 3 times with EA. The combined organic layers were dried over Na$_2$SO$_4$, filtrated and concentrated in vacuo to yield 5.58 g of an orange oil containing 70% of the desired product. This material was used in subsequent steps without further purification. Characteristic pyrazoline signals in $^1$H NMR (400 MHz, CDCl$_3$): δ 2.77-2.86 (m, 1H), 3.08-3.18 (m, 1H), 4.95-5.03 (m, 1H), 6.88 (br s, 1H).

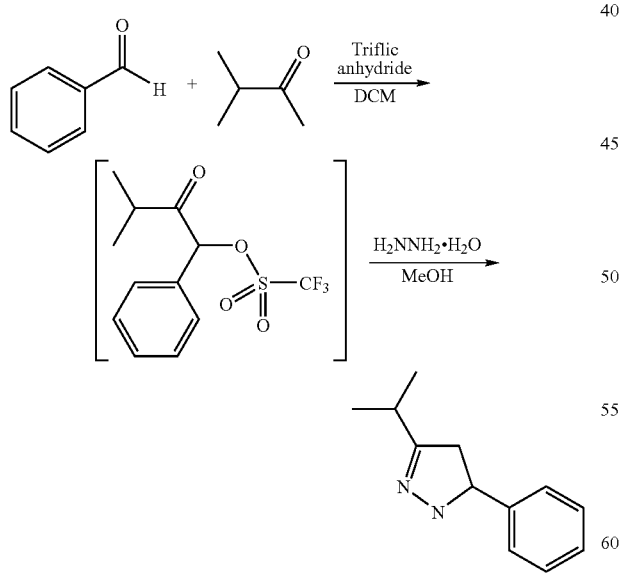

3-Isopropyl-5-phenyl-4,5-dihydro-1H-pyrazole 0.38 mL 3-methyl-2-butanone was dissolved in 10 mL DCM. Added was 0.36 mL (1 equiv.) benzaldehyde, followed by dropwise addition of 1.50 mL triflic anhydride. The mixture was stirred for 1 hour at room temperature. Subsequently, 10 mL MeOH and 0.87 mL (5 equiv.) hydrazine hydrate were added. The mixture was stirred for 30 minutes at room temperature, and concentrated in vacuo. The residue was taken up in DCM, extracted with 5% aqueous NaHCO$_3$, and the organic phase was dried over Na$_2$SO$_4$, filtrated and concentrated in vacuo to yield 520 mg of a brown oil containing about 50% of the desired product, which was used in subsequent steps without further purification.

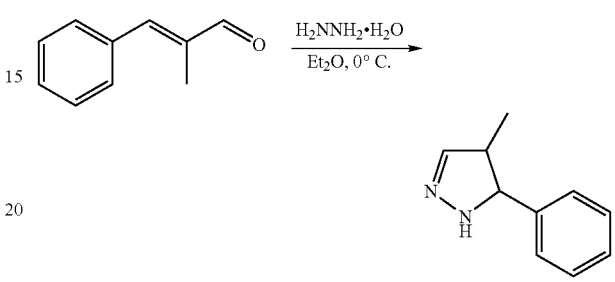

4-Methyl-5-phenyl-4,5-dihydro-1H-pyrazole 5.22 ml (1 equiv.) hydrazine hydrate was added to 100 mL diethylether. The emulsion was cooled with an ice bath. 15.0 mL 2-Methyl-3-phenyl-propenal was added dropwise, and the mixture was stirred overnight at room temperature. H$_2$O was added, the organic layer was separated and the aqueous layer was extracted with diethylether. The combined organic layers were dried over Na$_2$SO$_4$, filtrated and concentrated in vacuo. Vacuum destillation yielded 5.9 g of desired product (mixture of diastereomeric pairs) as a clear fluid (76-82° C., 0.2-0.3 mbar). $^1$H NMR (400 MHz, CDCl$_3$) of first diastereomeric pair: δ 0.71 (d, J=7 Hz), 3H), 3.20-3.31 (m, 1H), 4.77 (d, J=10 Hz, 1H), 6.73 (br s, 1H), 7.23-7.42 (m, 5H), 8.55-8.60 (m, 2H). $^1$H NMR (400 MHz, CDCl$_3$) of second diastereomeric pair: δ 1.24 (d, J=7 Hz), 3H), 2.90-3.11 (m, 1H), 4.22 (d, J=11 Hz, 1H), 6.71 (br s, 1H), 7.23-7.42 (m, 5H), 8.55-8.60 (m, 2H).

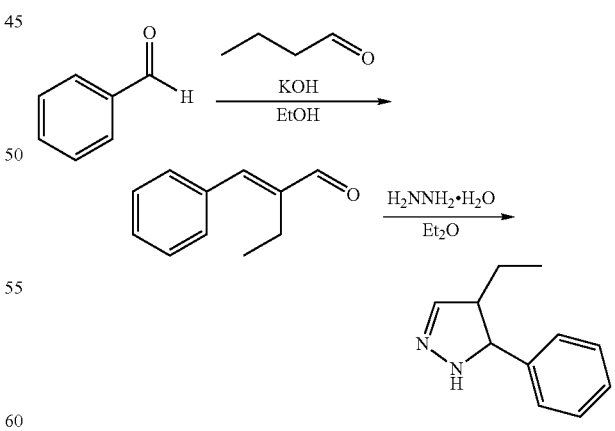

2-Benzylidene-butyraldehyde 30.0 mL Benzaldehyde was dissolved in 150 mL EtOH and cooled with an ice bath. Added was 5.01 mL. 45% KOH (0.2 equiv.), followed by dropwise addition of 16.5 mL butyraldehyde. The mixture was stirred for 3 days at room temperature, acidified with 1M HCl and extracted with ether. The organic layer was dried over $Na_2SO_4$, filtrated and concentrated in vacuo. Vacuum destillation yielded 20.4 g of a yellow fluid (78-82° C., 0.6 mbar) containing 70% of the desired product. This material was used in subsequent steps without further purification. Characteristic signals in $^1$H NMR (400 MHz, $CDCl_3$): δ 1.15 (t, J=7.5 Hz, 3H), 2.57 (q, J=7.5 Hz, 1H), 7.22 (s, 1H), 9.56 (s, 1H).

4-Ethyl-5-phenyl-4,5-dihydro-1H-pyrazole 62 ml (10 equiv.) hydrazine hydrate was added to 150 mL diethylether. The emulsion was cooled with an ice/NaCl bath to −10° C. A solution of 20.4 g 2-benzylidene-butyraldehyde in 100 mL ether was added dropwise at −10° C. and stirred at −10° C. for 3 hours. The mixture was stirred overnight (with ice bath) and allowed to slowly reach room temperature. $H_2O$ was added, the organic layer was separated and the aqueous layer was extracted 2 times with diethylether. The combined organic layers were dried over $Na_2SO_4$, filtrated and concentrated in vacuo. Vacuum destillation yielded 6.1 g of a clear fluid (102-106° C., 0.6 mbar) containing 94% of the desired product (mixture of diastereomeric pairs). Characteristic signals of the first diastereomeric pair: $^1$H NMR (400 MHz, $CDCl_3$) δ 0.83 (t, J=6.5 Hz, 3H), 3.03-3.13 (m, 1H), 4.74-4.81 (m, 1H), 6.83 (br s, 1H). Characteristic signals of the second diastereomeric pair: $^1$H NMR (400 MHz, $CDCl_3$) δ 1.00 (t, J=7.5 Hz, 3H), 2.84-2.93 (m, 1H), 4.28-4.34 (m, 1H), 6.76 (br s, 1H).

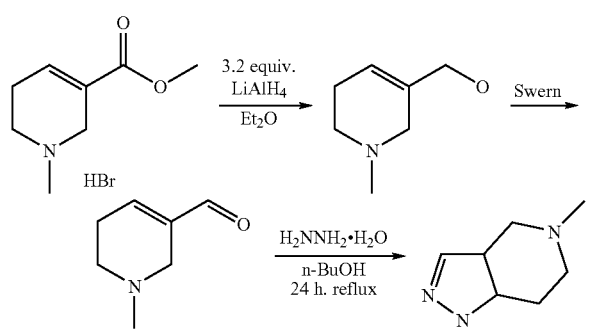

(1-Methyl-1,2,5,6-tetrahydro-pyridin-3-yl)-methanol 15.0 g of 1-Methyl-1,2,5,6-tetrahydro-pyridine-3-carboxylic acid methyl ester hydrobromide was taken up in EA and extracted with 2M NaOH. The organic layer was separated and the aqueous layer again extracted with EA. The combined organic layers were dried over $Na_2SO_4$, filtrated and concentrated to yield 8.27 g of the free base as a yellow oil (84%).

6.5 g of $LiAlH_4$ (3.2 equiv.) was suspended in 100 mL dry THF and cooled with an ice bath. To this was added dropwise a solution of 8.27 g 1-Methyl-1,2,5,6-tetrahydro-pyridine-3-carboxylic acid methyl ester (free base) in 50 mL dry THF. The mixture was stirred for 3 hours at room temperature. The mixture was cooled with an ice bath and 6.5 mL $H_2O$, 13 mL 2 M NaOH and 6.5 mL $H_2O$ were added dropwise. The residue was filtered, washed with ether and the filtrate was concentrated in vacuo to yield 6.7 g of a colorless oil. $^1$H NMR (400 MHz, $CDCl_3$) δ 2.18-2.26 (m, 2H), 2.36 (s, 3H), 2.49 (t, J=6 Hz, 2H), 2.92-2.97 (m, 2H), 4.00 (br s, 2H), 5.68 (br s, 1H).

1-Methyl-1,2,5,6-tetrahydro-pyridine-3-carbaldehyde 2.88 mL oxalyl chloride (2.4 equiv.) was dissolved in 20 mL DCM. The mixture was cooled to −78° C. and a solution of 3.37 mL DMSO (2.0 equiv.) in 10 mL DCM was added dropwise. The mixture was stirred for 15 minutes at −78° C. A solution of 3.0 g (1-Methyl-1,2,5,6-tetrahydro-pyridin-3-yl)-methanol in 10 mL DCM was added dropwise while keeping the temperature below −65° C. The mixture was stirred for 15 minutes at −78° C. 9.81 mL Triethylamine (3.0 equiv.) was added dropwise and subsequently the mixture was allowed to warm to room temperature. 50 mL DCM was added to keep the mixture stirrable. The mixture was stirred for 1 hour at room temperature. $H_2O$ was added, the organic layer was separated and the aqueous layer again extracted with DCM. The combined organic layers were dried over $Na_2SO_4$, filtrated and concentrated to yield 3.24 g of an orange oil (85% pure) which was used without further purification in the subsequent step. $^1$H NMR (400 MHz, $CDCl_3$) δ 2.43 (s, 3H), 2.48-2.60 (m, 4H), 3.11-3.15 (m, 2H), 6.85 (m, 1H), 9.43 (s, 1H).

5-Methyl-3a,4,5,6,7,7a-hexahydro-1H-pyrazolo[4,3-c]pyridine 3.2 g 1-Methyl-1,2,5,6-tetrahydro-pyridine-3-carbaldehyde was dissolved in 10 mL n-BuOH. Added were 2 equiv. of hydrazine hydrate, the mixture was refluxed for 24 hours and subsequently concentrated in vacuo. The residue was taken up in DCM and extracted with 2M NaOH, and the organic phase was dried over $Na_2SO_4$, filtrated and concentrated in vacuo to yield 1.78 g of a brown oil which was used without further purification in the subsequent step.

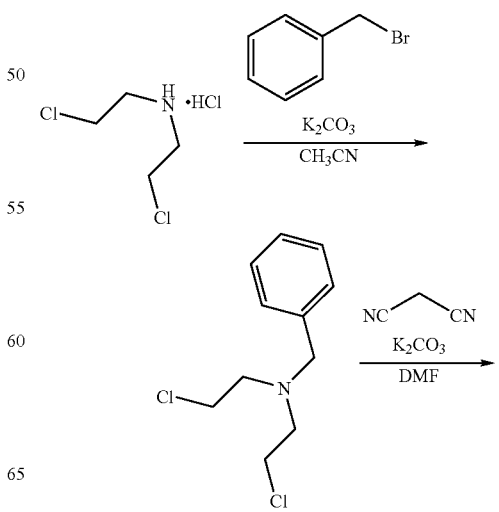

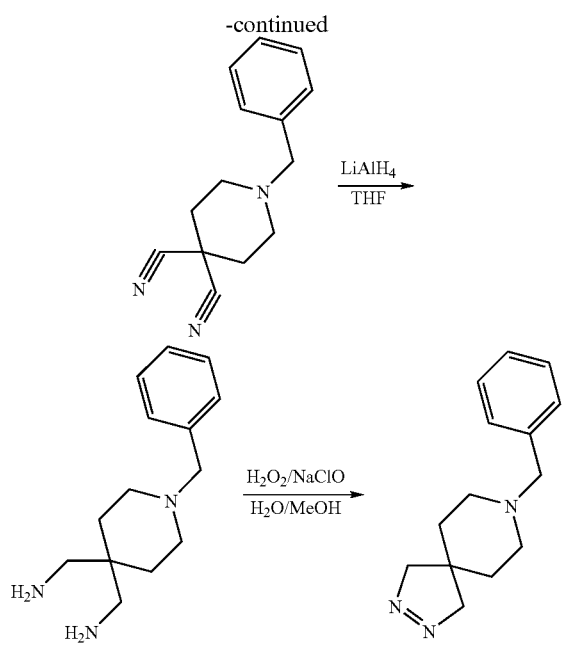

Benzyl-bis-(2-chloro-ethyl)-amine

Bis-(2-chloro-ethyl)-amine hydrochloride was suspended in 150 mL acetonitrile. Added were 34.8 g $K_2CO_3$ (3 equiv.) and 10.0 mL benzylbromide (1 equiv.). The mixture was refluxed overnight. Concentration on silica and purification with flash column chromatography (eluents PA:ether=95:5) yielded 4.11 g of a colorless oil. $^1$H NMR (400 MHz, $CDCl_3$) δ 2.93 (t, J=7 Hz, 4H), 3.50 (t, J=7 Hz, 4H), 3.74 (s, 2H), 7.22-7.37 (m, 5H).

1-Benzyl-piperide-4,4-dicarbonitrile 0.57 g Malonitrile was dissolved in 20 mL DMF. Added was 1.31 g $K_2CO_3$ (1.1 equiv.) and the mixture was stirred for 2 hours at 65° C. A solution of 2.0 g benzyl-bis-(2-chloro-ethyl)-amine (1 equiv.) in 10 mL DMF was added dropwise at 65° C., and the mixture was stirred for another 3 h. at 65° C. After cooling down, the mixture was diluted with EA and extracted with 5% aqueous $NaHCO_3$. The organic phase was dried over $Na_2SO_4$, filtrated and concentrated in vacuo to yield 2.02 g of an orange oil containing 85% of the anticipated product and 15% benzyl-bis-(2-chloro-ethyl)-amine. This material was used in the subsequent step without further purification. $^1$H NMR (400 MHz, $CDCl_3$) δ 2.24 (t, J=5.5 Hz, 4H), 2.50-2.75 (br s, 4H), 3.55 (s, 2H), 7.22-7.42 (m, 5H).

C-(4-Aminomethyl-1-benzyl-piperidin-4-yl)-methylamine 1.50 g of $LiAlH_4$ (3 equiv.) was suspended in 100 mL dry diethylether and cooled with an ice bath. To this was added dropwise a solution of 2.99 g 1-Benzyl-piperide-4,4-dicarbonitrile in 50 mL dry THF. The mixture was stirred overnight at room temperature. The mixture was cooled with an ice bath and 1.5 mL $H_2O$, 3 mL 2 M NaOH and 1.5 mL $H_2O$ were added dropwise. The residue was filtered, washed with THF and the filtrate was concentrated in vacuo to yield 2.63 g of a yellow oil containing about 60% of the desired product, which was used without further purification in the subsequent step. $^1$H NMR (400 MHz, $CDCl_3$) δ 1.00-1.60 (br s, 2H), 1.46 (t, J=5.5 Hz, 4H), 2.40 (t, J=5.5 Hz, 4H), 2.65 (s, 4H), 3.50 (s, 2H) 7.20-7.36 (m, 5H).

8-Benzyl-2,3,8-triaza-spiro[4.5]dec-2-ene 2.48 g of C-(4-Aminomethyl-1-benzyl-piperidin-4-yl)-methylamine was suspended in 40 mL $H_2O$ and 10 mL MeOH and cooled with an ice bath. Simultaneously, 6.7 mL 30% $H_2O_2$ (6 equiv.) and 15.2 mL 10% NaClO (2.4 equiv.) were added dropwise. The mixture was stirred at room temperature for 1 hour. The mixture was extracted 2 times with DCM, the combined organic layers were dried over $Na_2SO_4$, filtrated and concentrated to yield 2.20 g of a yellow oil which was used without further purification in the subsequent step.

Following route 2, compound 155 was prepared with this pyrazoline building block. From this, benzyl deprotection (ACE-chloride in 1,2-DCE followed by MeOH) gave compound 156, which was methylated by reductive alkylation (($CH_2O$)$_n$ in the presence of $NaBH(OAc)_3$ in 1,2-DCE) to give compound 157.

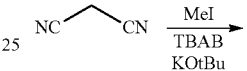

Methylmalonitrile

To malonitrile (10.00 g; 151.32 mmol; 2.0 equiv.) was added iodomethane (4.71 ml; 75.66 mmol; 1.0 equiv.) and tetrabutylammonium bromide (0.98 g; 3.03 mmol; 0.04 equiv.). The mixture was stirred at room temperature for 30 minutes, subsequently cooled with an ice bath, and potassium tert-butoxide (8.49 g; 75.66 mmol; 1.0 equiv.) was added slowly (addition started before mixture solidifies). The mixture was stirred for 2 hours at room temperature. Water was added, followed by extraction with DCM twice. Drying over $Na_2SO_4$, filtration and removal of the solvent yielded 10 g of a brown fluid, that was purified by flash-column chromatography with eluents DCM:PA=1:1, 3:1 and DCM to yield 3.25 g of a clear fluid (solidified upon standing). $^1$H NMR (400 MHz, $CDCl_3$) δ 1.79 (d, J=7.5 Hz, 3H), 3.79 (q, J=7.5 Hz, 1H).

2-Benzyloxymethyl-2-methyl-malononitrile

Methylmalonitrile (3.22 g; 39.40 mmol; 1.0 equiv.) was dissolved in THF (35 ml). Benzyl chloromethyl ether (7.54 g; 43.35 mmol; 1.1 equiv.) and sodium iodide (0.20 g; 1.33 mmol; 0.03 equiv.) were added. The yellow suspension was cooled with an ice bath and sodium hydride (1.89 g; 47.29 mmol; 1.2 equiv.) was added in small portions. More white precipitate was formed. The mixture was stirred for 30 min at room temperature, diluted with ether, and extracted with 5% aqueous $NaHCO_3$. The organic phase was dried over $Na_2SO_4$, filtrated and concentrated in vacuo to give 9.6 g of a yellow fluid/oil. Purification by flash column chromatography (eluens EA:PA=1:4) yielded 6.2 g of a yellow oil. $^1$H NMR (400 MHz, $CDCl_3$) δ 1.78 (s, 3H), 3.72 (s, 1H), 4.71 (s, 2H), 7.31-7.43 (m, 5H).

2-Benzyloxymethyl-2-methyl-propane-1,3-diamine $LiAlH_4$ (3.22 g; 84.84 mmol; 3.0 equiv.) was suspended in 30 mL dry diethylether and cooled with an ice bath. A solution of 2-Benzyloxymethyl-2-methyl-malononitrile (5.72 g; 28.28 mmol; 1.0 equiv.) in 20 mL dry diethylether was added dropwise. The suspension was stirred at room temperature for 4 hours, and subsequently cooled with an ice bath. To this was added 3.22 mL $H_2O$, 6.44 mL 2 M NaOH and 3.22 mL $H_2O$. The precipitate was filtered off and washed with ether. The filtrate was concentrated under reduced pressure to yield 5.47 g (84%) of a colorless oil. $^1$H NMR (400 MHz, $CDCl_3$) δ 0.84 (s, 3H), 2.59-2.69 (m, 4H) 3.29 (s, 2H), 4.49 (s, 2H), 7.24-7.39 (m, 5H).

4-Benzyloxymethyl-4-methyl-4,5-dihydro-3H-pyrazole 5.92 g 2-Benzyloxymethyl-2-methyl-propane-1,3-diamine was dissolved in water (40 mL) and MeOH (10 mL) and cooled with an ice bath. Simultaneously, 30% $H_2O_2$ (16.1 mL) and 10% NaClO (36.5 mL) were added dropwise. The resulting white emulsion was stirred overnight at room temperature. The mixture was extracted with DCM, the organic phase was dried over $Na_2SO_4$, filtrated and concentrated in vacuo to yield 5.69 g of a pale yellow oil, containing about 70% of the desired product, which was used without further purification in the subsequent step. $^1$H NMR (400 MHz, $CDCl_3$) δ 1.05 (s, 3H), 3.22 (s, 2H), 4.11-4.20 (m, 2H), 4.29-4.38 (m, 2H), 4.48 (s, 2H), 7.24-7.39 (m, 5H).

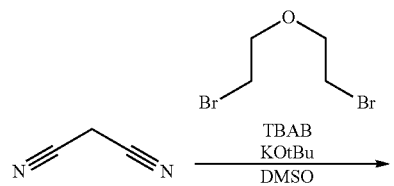

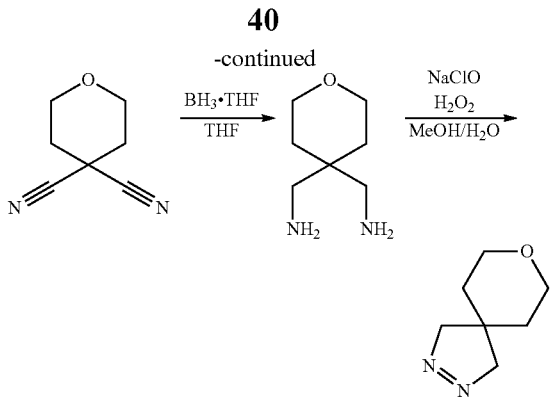

Tetrahydro-pyran-4,4-dicarbonitrile

Malononitrile (5.0 g) was dissolved in DMSO (5 mL). Subsequently, bis(2-bromoethyl)ether (9.49 mL) and TBAB (1.22 g) were added, followed by portionwise addition of KOtBu (8.49 g). The mixture was stirred for 4 h. at room temperature, taken up in DCM and extracted 3 times with 5% aqueous $NaHCO_3$. The organic phase was dried over $Na_2SO_4$ and evaporated under reduced pressure. The crude material was purified by flash chromatography eluting with PA:$Et_2O$ 65:35 ($R_f$=0.24, visualized with $KMnO_4$) to give 2.49 g (24%) of a solid. $^1$H NMR (400 MHz, $CDCl_3$) δ 2.24 (t, 4H), 3.87 (t, 4H).

C-(4-Aminomethyl-tetrahydro-pyran-4-yl)-methylamine

Tetrahydro-pyran-4,4-dicarbonitrile (1.52 g) was dissolved in dry THF (25 mL) and cooled to −10° C. To this solution, $BH_3$.THF (56 mL of an 1M solution in THF, 5 equiv.) was added dropwise, the mixture was allowed to warm to room temperature, and subsequently stirred at 60° C. for 6 h. The mixture was cooled in an ice bath, and HCl (24.2 mL of a 6M aqueous solution, 13 equiv.) was added. The mixture was allowed to warm to room temperature and stirred for 2 h. The mixture was neutralized with 2M aqueous NaOH and extracted three times with DCM. The aqueous layer was evaporated to dryness, the residue was stirred with $CHCl_3$, the solids were filtered off and the organic phase was evaporated under reduced pressure to yield 1.0 g (62%) of a yellow oil. $^1$H NMR (400 MHz, $CDCl_3$) δ 1.46 (t, 4H), 2.74 (s, 4H), 3.67 (t, 4H).

8-Oxa-2,3-diaza-spiro[4,5]dec-2-ene

C-(4-Aminomethyl-tetrahydro-pyran-4-yl)-methylamine (1.0 g) was taken up in a mixture of $H_2O$ (10 mL) and MeOH (2.5 mL), and cooled in an ice bath. Simultaneously, $H_2O_2$ (4.8 mL of a 30% solution, 6 equiv.) and NaClO (12.4 mL of a 10% solution, 2.4 equiv.) were added dropwise, the ice bath was removed, and the mixture was stirred overnight at room temperature. Extraction with DCM, drying over $Na_2SO_4$ and evaporation under reduced pressure yielded 380 mg of a clear, light-yellow liquid containing 85% of the anticipated product and 15% of the diamine starting material. This material was used in subsequent steps without further purification. $^1$H NMR (400 MHz, $CDCl_3$) δ 1.49 (t, 4H), 3.65 (t, 4H), 4.28 (s, 4H).

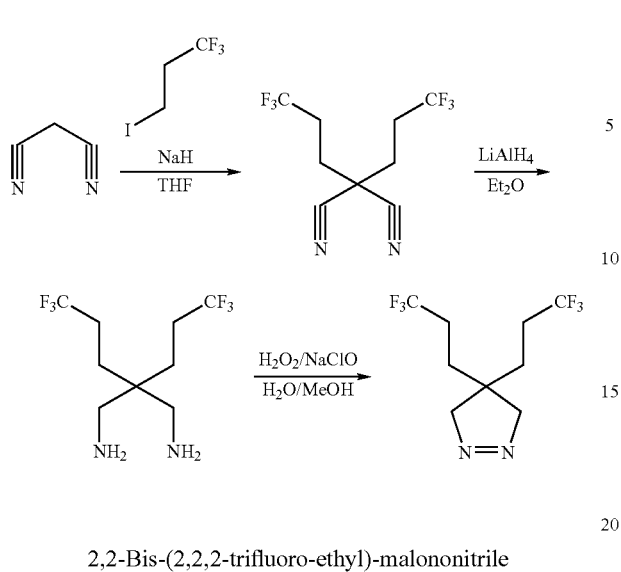

2,2-Bis-(2,2,2-trifluoro-ethyl)-malononitrile

Malononitril (20.15 mmol) and 1-iodo-3,3,3-trifluoropropane (42.65 mmol) were dissolved in 30 ml dry THF, and the mixture was cooled with an ice/salt bath. 1.61 g NaH (40.3 mmol) was added portionwise, keeping the temperature below 5° C. The reaction mixture was stirred at room temperature for 2 hours and evaporated under reduced pressure. The crude material was purified by flash chromatography eluting with DCM, yielding 0.76 grams of an oil. $^1$H NMR (400 MHz, CDCl$_3$) δ 2.62-2.49 (m, 4H), 2.31-2.24 (m, 4H)

2,2-Bis-(2,2,2-trifluoro-ethyl)-propane-1,3-diamine 340 mg LiAlH$_4$ (8.95 mmol) was suspended in 15 ml dry Et$_2$O and cooled in an ice bath. A solution of 760 mg 2,2-Bis-(2,2,2-trifluoro-ethyl)-malononitrile in Et$_2$O was added dropwise at such a rate that the temperature was kept below 20° C. The mixture was stirred overnight at room temperature, cooled in an ice bath, and quenched by adding H$_2$O (0.35 ml), 2M aqueous NaOH (0.70 ml), and again H$_2$O (0.35 ml). The suspension was filtered, the filtercake was washed with Et$_2$O, and the combined filtrates were evaporated to dryness under reduced pressure to give 0.72 g of an oil. This material was used in the subsequent step without further purification.

4,4-Bis-(2,2,2-trifluoro-ethyl)-4,5-dihydro-3H-pyrazole 2,2-Bis-(2,2,2-trifluoro-ethyl)-propane-1,3-diamine (720 mg) was taken up in a mixture of H$_2$O (3 ml) and MeOH (0.75 ml), and cooled in an ice bath. Simultaneously, H$_2$O$_2$ (1.7 mL of a 30% solution, 6 equiv.) and NaClO (3.85 mL of a 10% solution, 2.4 equiv.) were added dropwise, the ice bath was removed, and the mixture was stirred overnight at room temperature. The mixture was extracted with DCM, the organic phase was dried over MgSO$_4$, and evaporation under reduced pressure yielded 0.82 g of an oil containing 50% of the anticipated product and 50% of the diamine starting material. This material was used in the subsequent step without further purification. $^1$H NMR (400 MHz, CDCl$_3$) δ 4.25 (s, 2 H), 2.24-1.85 (m, 4 H), 1.85-1.43 (m, 4H).

EXAMPLE 4

Syntheses of Specific Compounds

Route 1

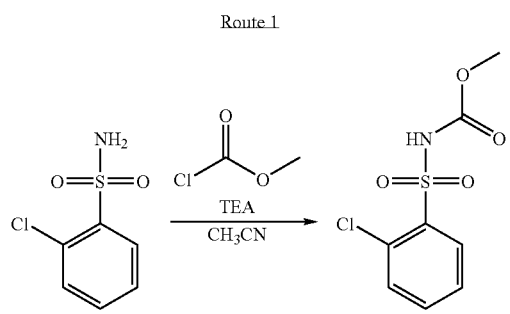

(2-Chloro-benzenesulfonyl)-carbamic acid methyl ester

To 25.0 g 2-chloro-benzenesulfonamide was added 75 mL acetonitrile and 45.2 mL (2.5 eq) triethylamine. The mixture was cooled with an ice bath and 15.1 mL methyl chloroformate was slowly added dropwise. The mixture was stirred overnight at room temperature and concentrated in vacuo. Water was added and de aqueous layer was washed two times with ether. Acidification of the aqueous layer with 2 M HCl led to formation of a white precipitate. The suspension was filtered, the residue was washed with H$_2$O and dried in vacuo to yield 19.1 g of a white solid. $^1$H NMR (400 MHz, DMSO-d$_6$) δ 3.58 (s, 3H), 7.52-7.61 (m, 1H), 7.62-7.72 (m, 2H), 8.10 (dd, J=8 and 1.5 Hz, 1H), 12.42 (br s, 1H).

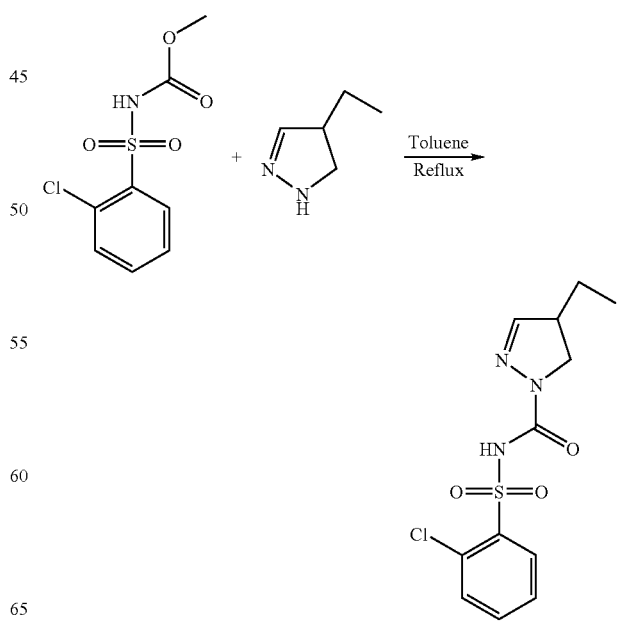

2-Chloro-N-4-ethyl-4,5-dihydro-pyrazole-1-carbonyl)benzenesulfonamide 8.5 g 4-Ethyl-4,5-dihydro-1H-pyrazole was dissolved in 75 mL toluene. 19.0 g (2-chloro-benzenesulfonyl)-carbamic acid methyl ester was added and the mixture was refluxed for 4 hours. After cooling down a precipitate was formed. The suspension was filtered, the residue was washed with PA and dried in vacuo to yield 20.3 g white crystals. $^1$H NMR (200 MHz, DMSO-$d_6$) δ 0.90 (t, J=7.5 Hz, 3H), 1.30-1.70 (m, 2H), 3.00-3.40 (m, 1H), 3.25 (t, J=10.5 Hz, 1H), 3.74 (t, J=10.5 Hz, 1H), 7.08 (s, 1H), 7.40-7.73 (m, 3H), 8.03-8.16 (m, 1H), 10.00 (br s, 1H).

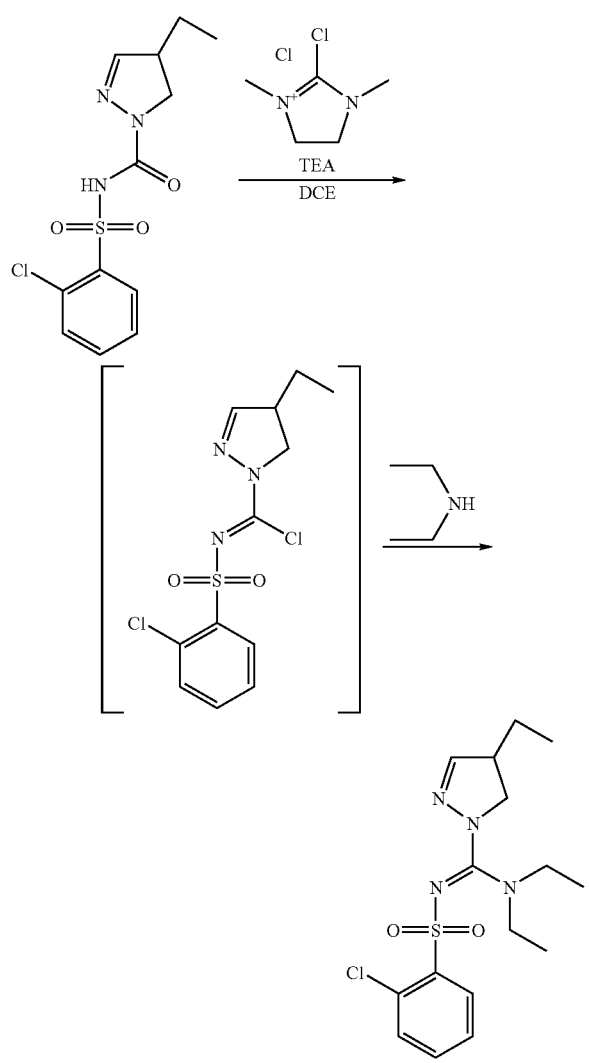

2-Chloro-N-[diethylamino-4-ethyl-4,5-dihydro-pyrazol-1-yl]-methylene]-benzene-sulfonamide (compound 1)

2.0 g 2-Chloro-N-4-ethyl-4,5-dihydro-pyrazole-1-carbonyl)benzenesulfonamide was dissolved in 10 mL DCE. 1.07 g 2-Chloro-1,3-dimethylimidazolinium chloride (DMC) and 1.75 mL TEA were added and the mixture was refluxed for 1.5 hours to generate the chloroimine intermediate in situ. Subsequently, 5 mL (excess) diethylamine was added and the mixture was stirred overnight at room temperature. The mixture was concentrated in vacuo and H$_2$O was added. Extraction with DCM (2 times), drying of the combined organic layers over Na$_2$SO$_4$, evaporation to dryness and purification with flash chromatography (ether, R$_f$=0.35) yielded 320 mg of a yellow oil $^1$H NMR (400 MHz, CDCl$_3$) δ 0.95 (t, J=7.5 Hz, 3H), 1.16 (t, J=7 Hz, 6H), 1.44-1.66 (m, 2H), 3.00-3.10 (m, 1H), 3.48 (q, J=7 Hz, 4H), 3.70 (dd, J=11 and 7 Hz, 1H), 4.11 (t, J=11 Hz, 1H), 6.97 (d, J=2 Hz, 1H), 7.30-7.41 (m, 2H), 7.46 (dd, J=7.5 and 2 Hz, 1H), 8.16 (dd, J=7.5 and 2 Hz, 1H).

Route 2

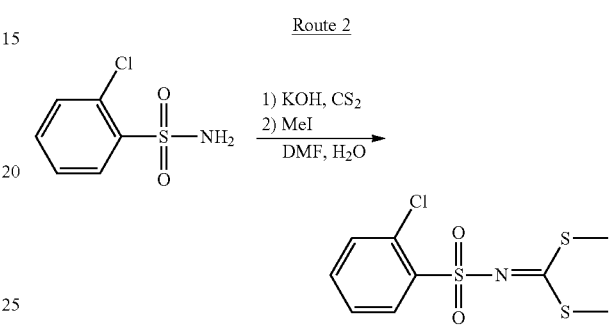

N-(Bis-methylsulfanyl-methylene)-2-chloro-benzenesulfonamide

To 41.6 g 2-chloro-benzenesulfonamide was added 300 mL DMF and 22 mL carbondisulfide. The mixture was cooled with an ice bath. A solution of 29 g KOH (15.0 mL) in 100 mL H$_2$O was added dropwise at such a rate that the temperature was kept below 10° C. The mixture was stirred for 30 minutes at 5° C. Subsequently, 32 mL MeI was added dropwise at such a rate that the temperature was kept below 10° C. Then, the mixture was allowed to warm to room temperature and stirred for another 30 minutes. H$_2$O was added and a precipitate formed. This was filtered off and washed with H$_2$O. The residue was triturated with EtOH, filtered off and dried in vacuo to yield 42.6 g white crystals. $^1$H NMR (200 MHz, CDCl$_3$) δ 2.57 (s, 6H), 7.32-7.60 (m, 3H), 8.11-8.27 (br d, J=7.5 Hz, 1H).

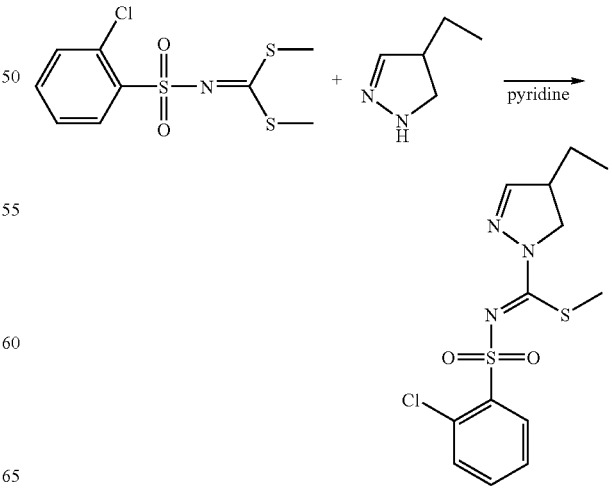

2-Chloro-N-[(4-ethyl-4,5-dihydro-pyrazol-1-yl)-methyl-sulfanyl-methylene]benzenesulfon-amide 500 mg 4-Ethyl-4,5-dihydro-1H-pyrazole was dissolved in 10 mL pyridine, 1.51 g N-(Bis-methylsulfanyl-methylene)-2-chloro-benzenesulfonamide was added and the mixture was refluxed overnight. The mixture was concentrated in vacuo and $H_2O$ was added, followed by extraction twice with DCM. The combined organic layers were dried over $Na_2SO_4$ and concentrated in vacuo. The crude product was purified with flash chromatography (gradient DCM:acetone=100:0 to 95:5) to yield 1.30 g of a yellow oil. $^1H$ NMR (400 MHz, $CDCl_3$) δ 1.02 (t, J=7.5 Hz, 3H), 1.55-1.77 (m, 2H), 2.28 (s, 3H), 3.27-3.39 (m, 1H), 4.13 (dd, J=11.5 and 6.5 Hz, 1H), 4.58 (t, J=11.5 Hz, 1H), 7.16 (d, J=2 Hz, 1H), 7.39 (dt, J=7.5 and 2 Hz, 1H), 7.46 (dt, J=7.5 and 2 Hz, 1H), 7.52 (dd, J=7.5 and 2 Hz, 1H), 8.17 (dd, J=7.5 and 2 Hz, 1H).

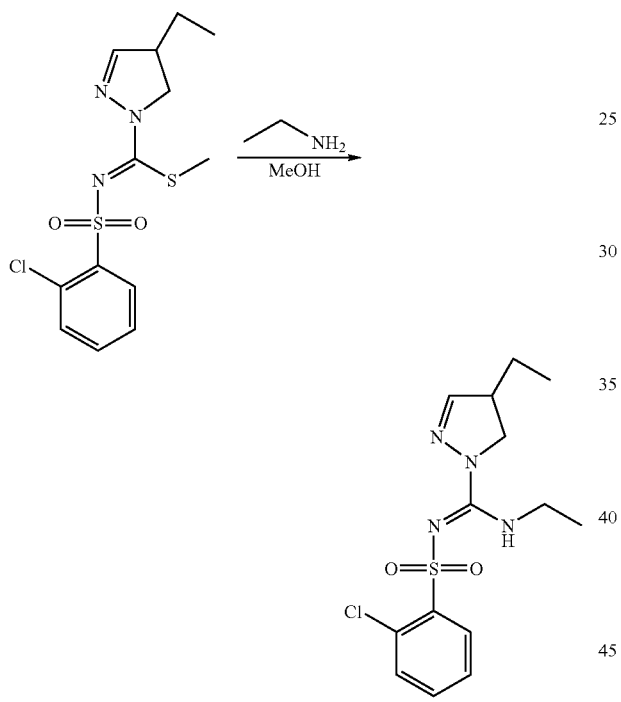

2-Chloro-N-[ethylamino-(4-ethyl-4,5-dihydro-pyrazol-1-yl)-methylene]-benzenesulfon-amide (compound 2)

1.30 g 2-Chloro-N-[(4-ethyl-4,5-dihydro-pyrazol-1-yl)-methyl-sulfanyl-methylene]-benzenesulfon-amide was dissolved in 10 mL MeOH. 5 mL (excess) of a 70% solution of ethylamine in $H_2O$ was added and the mixture was stirred for 1 hour at room temperature. The mixture was concentrated in vacuo and the crude product was purified by flash chromatography (ether, $R_f$=0.33) to yield 1.09 g of a colorless oil. $^1H$ NMR (400 MHz, $CDCl_2$) δ 0.95 (t, J=7.5 Hz, 3H), 1.16 (t, J=7 Hz, 3H), 1.44-1.69 (m, 2H), 3.03-3.18 (m, 1H), 3.44-3.58 (m, 2H), 3.71 (br dd, J=11 and 7.5 Hz, 1H), 4.12 (br t, J=11 Hz, 1H), 6.86 fors, 1H), 6.94 (d, J=2 Hz, 1H), 7.35 (dt, J=7.5 and 2 Hz, 1H), 7.40 (dt, J=7.5 and 2 Hz, 1H), 7.48 (dt, J=7.5 and 2 Hz, 1H), 8.18 (dd, J=7.5 and 2 Hz, 1H).

In an analogous manner, the compounds in the table below marked 'route 2' have been prepared.

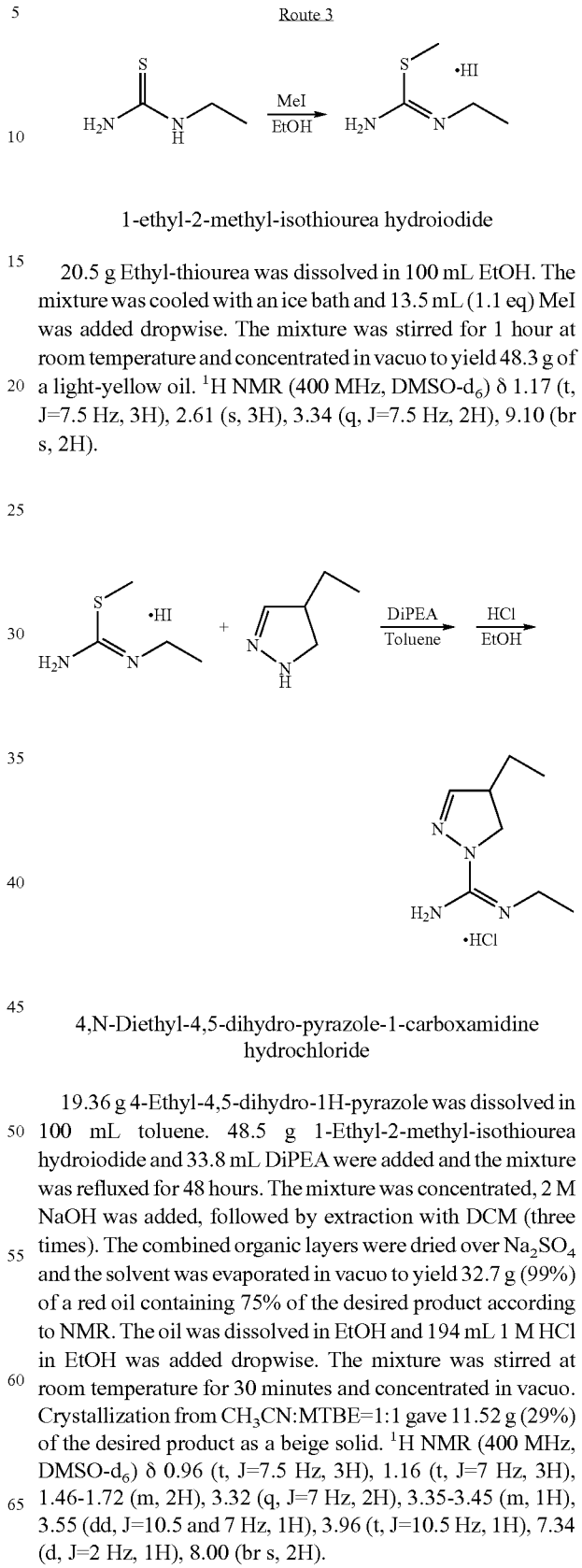

1-ethyl-2-methyl-isothiourea hydroiodide 20.5 g Ethyl-thiourea was dissolved in 100 mL EtOH. The mixture was cooled with an ice bath and 13.5 mL (1.1 eq) MeI was added dropwise. The mixture was stirred for 1 hour at room temperature and concentrated in vacuo to yield 48.3 g of a light-yellow oil. $^1H$ NMR (400 MHz, DMSO-$d_6$) δ 1.17 (t, J=7.5 Hz, 3H), 2.61 (s, 3H), 3.34 (q, J=7.5 Hz, 2H), 9.10 (br s, 2H).

4,N-Diethyl-4,5-dihydro-pyrazole-1-carboxamidine hydrochloride 19.36 g 4-Ethyl-4,5-dihydro-1H-pyrazole was dissolved in 100 mL toluene. 48.5 g 1-Ethyl-2-methyl-isothiourea hydroiodide and 33.8 mL DiPEA were added and the mixture was refluxed for 48 hours. The mixture was concentrated, 2 M NaOH was added, followed by extraction with DCM (three times). The combined organic layers were dried over $Na_2SO_4$ and the solvent was evaporated in vacuo to yield 32.7 g (99%) of a red oil containing 75% of the desired product according to NMR. The oil was dissolved in EtOH and 194 mL 1 M HCl in EtOH was added dropwise. The mixture was stirred at room temperature for 30 minutes and concentrated in vacuo. Crystallization from $CH_3CN$:MTBE=1:1 gave 11.52 g (29%) of the desired product as a beige solid. $^1H$ NMR (400 MHz, DMSO-$d_6$) δ 0.96 (t, J=7.5 Hz, 3H), 1.16 (t, J=7 Hz, 3H), 1.46-1.72 (m, 2H), 3.32 (q, J=7 Hz, 2H), 3.35-3.45 (m, 1H), 3.55 (dd, J=10.5 and 7 Hz, 1H), 3.96 (t, J=10.5 Hz, 1H), 7.34 (d, J=2 Hz, 1H), 8.00 (br s, 2H).

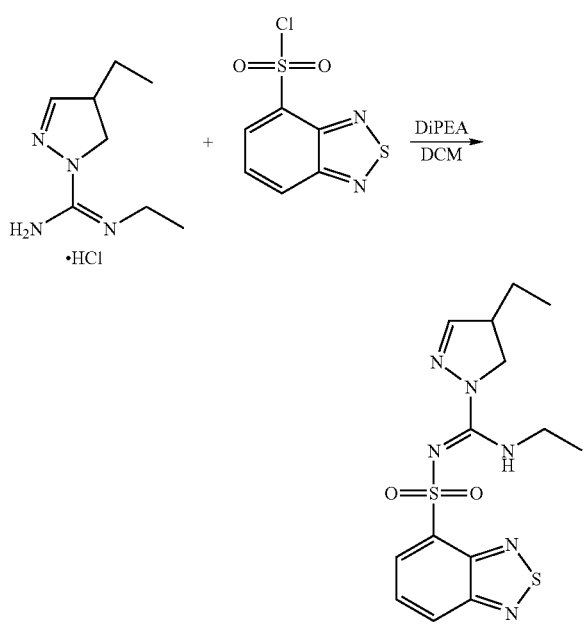

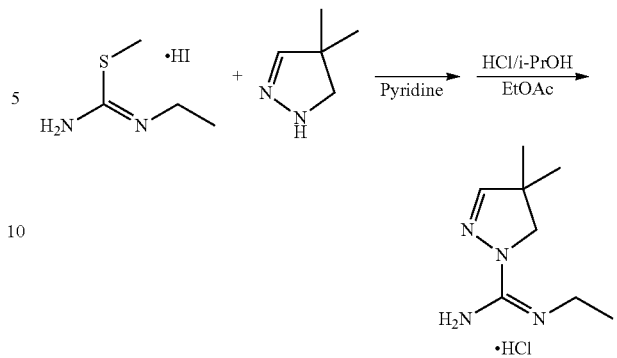

N-Ethyl-4,4-dimethyl-4,5-dihydro-pyrazole-1-carboxamidine hydrochloride 2.0 g 4,4-dimethyl-4,5-dihydro-3H-pyrazole was dissolved in 100 mL pyridine. A solution of 30.0 g 1-Ethyl-2-methyl-isothiourea hydroiodide in 50 mL pyridine was added and the mixture was refluxed for 20 hours. The mixture was cooled to room temperature and concentrated under reduced pressure, and the residue was taken up in DCM (120 mL). The organic phase was extracted with 2M NaOH (2×120 mL), washed with water (120 mL), dried over $Na_2SO_4$ and evaporated under reduced pressure to yield 16.3 g (79%) of an orange oil. The oil (10.0 g) was taken up in EtOAc (50 mL) and heated to 60° C. After removal of the heat source, a 5-6M solution of HCl in isopropanol (20 mL) was dosed over a period of 4 minutes. After cooling to room temperature, EtOAc (50 mL) was added over a period of 4 minutes, and the mixture was stirred at 20° C. for 90 minutes. The formed crystals were collected by filtration and washed with EtOAc (20 mL), followed by drying under reduced pressure at mild heating, to give 6.52 g (54%) of the desired product as a yellow solid. $^1$H NMR (400 MHz, DMSO-$d_6$) δ 1.13 (t, J=7 Hz, 3H), 1.24 (s, 6H), 3.27-3.34 (m, 2H), 3.64 (s, 2H), 7.26 (s, 1H), 8.03 (br s, 2H), 8.13 (br s, 1H).

Benzo[1,2,5]thiadiazole-4-sulfonic acid ethylamino-(4-ethyl-4,5-dihydro-pyrazol-1-yl)-methyleneamide (compound 78)

300 mg 4,N-Diethyl-4,5-dihydro-pyrazole-1-carboxamidine hydrochloride was suspended in 10 mL. DCM. 0.53 mL DiPEA and 310 mg benzo[1,2,5]thiadiazole-4-sulfonylchloride were added and the mixture was stirred overnight at room temperature. The mixture was washed with 5% $NaHCO_3$ and 2 M NaOH, the organic layer dried over $Na_2SO_4$ and the solvent evaporated in vacuo to yield 410 mg of a red/brown oil. The crude product was purified by flash chromatography (DCM:aceton=98:2, $R_f$=0.18) to yield 350 mg (65%) of an orange oil. $^1$H NMR (400 MHz, $CDCl_3$) δ 0.93 (t, J=7.5 Hz, 3H), 1.16 (br t, J=7 Hz, 3H), 1.41-1.66 (m, 2H), 3.01-3.16 (m, 1H), 3.39-3.55 (m, 2H), 3.59-3.74 (m, 1H), 3.95-4.15 (m, 1H), 6.94 (br s, 1H), 6.95 (br s, 1H), 7.68 (dd, J=9 and 7 Hz, 1H), 8.15 (br d, J=9 Hz, 1H), 8.31 (br d, J=7 Hz, 1H).

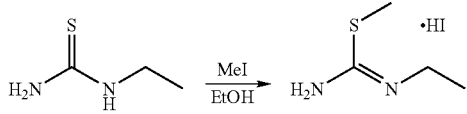

1-ethyl-2-methyl-isothiourea hydroiodide 20.0 g Ethyl-thiourea was suspended in 100 mL EtOH, and 30 g (1.1 eq) MeI was added dropwise, during which the mixture became a clear yellow solution. Subsequently, the mixture was stirred for 1 hour at room temperature and concentrated in vacuo to yield 48.1 g of a yellow oil. $^1$H NMR (400 MHz, DMSO-$d_6$) δ 1.17 (t, J=7.5 Hz, 3H), 2.61 (s, 3H), 3.34 (q, J=7.5 Hz, 2H), 9.10 (br s, 2H).

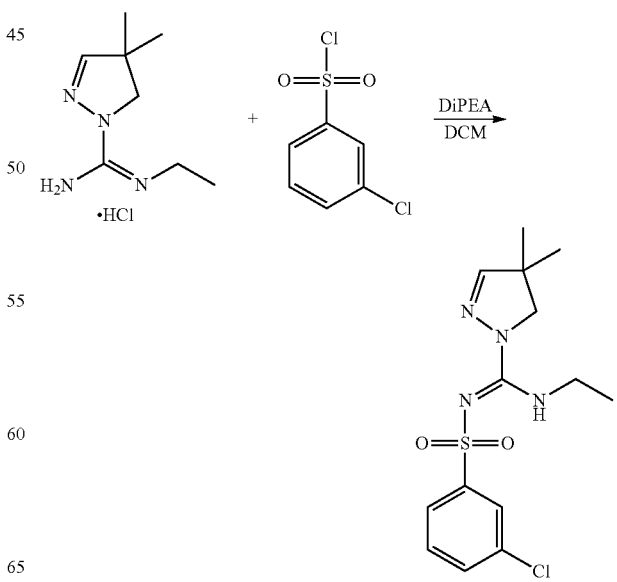

3-Chloro-N-[(4,4-dimethyl-4,5-dihydro-pyrazol-1-yl)-ethylamino-methylene]-benzenesulfonamide (compound 33)

6.39 g N-Ethyl-4,4-dimethyl-4,5-dihydro-pyrazole-1-carboxamidine hydrochloride was suspended in 65 mL DCM. 12.0 mL DiPEA and 3.96 mL 3-chloro-benzenesulfonyl chloride were added and the suspension was stirred for 20 h. at room temperature, resulting in a dark brown turbid solution. The mixture was extracted with 2M NaOH (2×125 mL) and 1M HCl (2×125 mL), washed with water (100 mL), and the organic layer was dried over $Na_2SO_4$ followed by evaporation under reduced pressure to yield 7.70 g of a brown oil. The oil (1.0 g) was dissolved in MTBE (3 mL) under reflux, and the solution was slowly cooled to room temperature, initializing crystallization The suspension was stirred for 10 min at room temperature, hexane (6 mL) was added over a period of 1 minute. The resulting suspension was stirred for 20 min. at room temperature and 50 min. at 0° C., and product was collected by filtration and washed with hexane (1 mL). Drying under reduced pressure at 40° C. yielded 0.85 g of a light-brown solid, m.p. 62-67° C.

In an analogous manner, the compounds in the table below marked 'route 3' have been prepared.

| Comp | structure | S* | Physico-chemical prop. | | | pharmacology | |
| | | | TLC Rf (x) | LCMS Rt | m.p. °C. | 5-HT$_6$ pA$_2$ | pK$_i$ |
| --- | --- | --- | --- | --- | --- | --- | --- |
| 1 | | 1 | 0.35 (a) | 1.99 | | 6.5 | |
| 2 | | 2 | 0.33 (a) | 1.84 | — | 8.5 | 7.3 |
| 3 | | 2 | — | 1.69 | 161-163 | | |
| 4 | | 2 | 0.20 (a) | 1.54 | — | | |
| 5 | | 2 | — | 1.77 | 94-95 | | |
| 6 | | 2 | 0.19 (a) | 1.80 | 91-93 | | |

-continued

| Comp | structure | S* | TLC Rf (x) | LCMS Rt | m.p. °C. | 5-HT₆ pA₂ | pK$_i$ |
|---|---|---|---|---|---|---|---|
| 7 | | 2 | — | 1.96 | — | | |
| 8 | | 2 | 0.35 (a) | 1.83 | | | |
| 9 | | 2 | — | 2.27 | | | |
| 10 | | 2 | 0.25 (b) | 1.12 | | | |
| 11 | | 2 | — | 1.40 | 131-138 | | |
| 12 | | 2 | 0.27 (a) | 1.80 | 128-130 | | |
| 13 | | 2 | — | 2.16 | — | 6.7 | 7.1 |

-continued

| Comp | structure | S* | TLC Rf(x) | LCMS Rt | m.p. °C. | 5-HT$_6$ pA$_2$ | pK$_i$ |
|---|---|---|---|---|---|---|---|
| 14 | | 2 | — | 1.21 | | | |
| 15 | | 2 | — | 1.42 | | | |
| 16 | | 2 | — | 1.17 | 162-173 | | 6.7 |
| 17 | | 2 | — | 1.34 | — | | |
| 18 | | 2 | — | 1.46 | | | |

-continued

| Comp | structure | S* | TLC Rf (x) | LCMS Rt | m.p. °C. | 5-HT$_6$ pA$_2$ | pK$_i$ |
|---|---|---|---|---|---|---|---|
| 19 | | 2 | 0.25 (a) | 1.67 | — | | |
| 20 | | 2 & 3 | 0.17 (c) | 2.04 | 58-61 | | |
| (+)-20 | (+)-enantiomer +98° (1%, MeOH) | 2 | | 2.04 | | 8.0 | 8.6 |
| (−)-20 | (−)-enantiomer −95° (1%, MeOH) | 2 | | 2.04 | | 7.7 | 7.8 |
| 21 | | 2 | — | 1.75 | 84-86 | | |
| 22 | | 2 | — | 1.62 | — | | |
| 23 | | 2 | — | 1.66 | | | |
| 24 | | 2 | 0.19 (a) | 1.44 | 43-45 | | |
| 25 | | 2 | — | 1.48 | | 8.0 | 7.8 |

-continued

| Comp | structure | S* | TLC Rf (x) | LCMS Rt | m.p. °C. | 5-HT$_6$ pA$_2$ | pK$_i$ |
|---|---|---|---|---|---|---|---|
| 26 | | 2 | — | 1.68 | | | |
| 27 | | 2 | — | 1.40 | | | |
| 28 | | 2 | 0.20 (a) | 1.78 | | 7.1 | 7.7 |
| 29 | | 2 | 0.65 (q) | 1.76 | 141-142 | | |
| 30 | | 2 | | 1.79 | 114-115 | 5.9 | |
| 31 | | 2 | | 1.67 | 131-133 | | |
| 32 | | 2 | 0.30 (e) | 2.08 | 79-80 | | |
| 33 | | 2 & 3 | 0.45 (a) | 1.99 | 62-67 | 7.9 | 7.8 |

| Comp | structure | S* | TLC Rf (x) | LCMS Rt | m.p. °C. | pA₂ | pK_i |
|---|---|---|---|---|---|---|---|
| 34 | | 2 | — | 2.08 | | | |
| 35 | | 2 | — | 1.74 | | | |
| 36 | | 2 | 0.18 (a) | 1.87 | | | |
| 37 | | 2 | | 2.33 | | | |
| 38 | | 2 | | 2.16 | | | |
| 39 | | 2 | | 2.04 | | | |
| 40 | | 2 | | 2.09 | | | |
| 41 | | 2 | 0.23 (a) | 1.71 | 141-142 | | |
| (+)-41 | (+)-enantiomer +9° (1%, MeOH) | 2 | 0.22 (a) | | 96-101 | | 8.9 |

-continued

| Comp | structure | S* | TLC Rf (x) | LCMS Rt | m.p. °C. | 5-HT₆ pA₂ | pK$_i$ |
|---|---|---|---|---|---|---|---|
| (−)-41 | (−)-enantiomer −6° (1%, MeOH) | 2 | 0.22 (a) | | 99-105 | | |
| 42 | | 2 | 0.29 (f) | 1.83 | | 6.9 | 6.7 |
| 43 | | 2 | 0.60 (r) | | | | |
| 44 | | 2 | 0.15 (l) | | | | |
| 45 | | 2 | 0.26 (n) | | | | |
| 46 | | 2 | 0.52 (l) | | | | |
| 47 | | 2 | 0.30 (o) | | | | |
| 48 | | 2 | 0.22 (c) | 2.19 | | | |

| Comp | structure | S* | TLC Rf(x) | LCMS Rt | m.p. °C. | 5-HT$_6$ pA$_2$ | pK$_i$ |
|---|---|---|---|---|---|---|---|
| 49 | | 2 | 0.22 (s) | 2.11 | | | |
| 50 | | 2 | | 2.13 | | | |
| 51 | | 3 | 0.39 (g) | | | 6.7 | 6.9 |
| 52 | | 3 | 0.26 (g) | | | | |
| 53 | | 3 | 0.38 (g) | | | | |
| 54 | | 3 | 0.37 (g) | | | | |
| 55 | | 3 | 0.39 (g) | | | | |
| 56 | | 3 | 0.45 (g) | | | | |

-continued

| | | | Physico-chemical prop. | | | pharmacology | |
| | | | TLC | LCMS | | 5-HT$_6$ | |
| Comp | structure | S* | Rf (x) | Rt | m.p. °C. | pA$_2$ | pK$_i$ |
|---|---|---|---|---|---|---|---|
| 57 | | 3 | 0.51 (g) | | | | |
| 58 | | 3 | 0.42 (g) | | | | |
| 59 | | 3 | 0.37 (g) | | | | |
| 60 | | 3 | 0.43 (g) | | | | |
| 61 | | 3 | 0.53 (g) | | | | |
| 62 | | 3 | 0.46 (g) | | | | |
| 63 | | 3 | 0.49 (g) | | | | |

-continued

| Comp | structure | S* | TLC Rf (x) | LCMS Rt | m.p. °C. | 5-HT$_6$ pA$_2$ | pK$_i$ |
|------|-----------|----|------------|---------|----------|-----------------|--------|
| 64 | | 3 | 0.58 (g) | | | | |
| 65 | | 3 | 0.48 (g) | | | | |
| 66 | | 3 | 0.45 (g) | | | | |
| 67 | | 3 | 0.38 (g) | | | | |
| 68 | | 3 | 0.47 (g) | | | | |
| 69 | | 3 | 0.46 (g) | | | | |
| 70 | | 3 | 0.33 (g) | | | | |

|  |  |  | Physico-chemical prop. | | | pharmacology | |
|---|---|---|---|---|---|---|---|
|  |  |  | TLC | LCMS | | 5-HT$_6$ | |
| Comp | structure | S* | Rf (x) | Rt | m.p. °C. | pA$_2$ | pK$_i$ |
| 71 | | 3 | 0.42 (g) | | | | |
| 72 | | 3 | 0.43 (g) | | | | |
| 73 | | 3 | 0.44 (g) | | | | |
| 74 | | 3 | 0.45 (g) | | | | |
| 75 | | 3 | 0.34 (g) | | | | |
| 76 | | 3 | 0.45 (g) | | | | |
| 77 | | 3 | 0.44 (g) | | | | |
| 78 | | 3 | 0.18 (e) | 1.79 | | 7.1 | 7.2 |

|  |  |  | Physico-chemical prop. | | | pharmacology | |
|---|---|---|---|---|---|---|---|
|  |  |  | TLC | LCMS |  | 5-HT$_6$ | |
| Comp | structure | S* | Rf (x) | Rt | m.p. °C. | pA$_2$ | pK$_i$ |
| 79 |  | 3 | 0.22 (f) | 1.76 |  |  |  |
| 80 |  | 3 | 0.17 (g) | 1.45 |  |  |  |
| 81 |  | 3 | 0.44 (g) |  |  | 7.0 | 7.2 |
| 82 |  | 3 | 0.19 (h) | 1.73 | 57-61 |  |  |
| (+)-82 | (+)-enantiomer +89° (1%, MeOH) | 2 | 0.19 (h) | 1.78 | 54-57 | 9.1 | 8.6 |
| (−)-82 | (−)-enantiomer −85° (1%, MeOH) | 2 | 0.19 (h) | 1.78 | 54-57 | 8.7 | 8.0 |
| 83 |  | 3 | 0.49 (g) |  |  | 7.2 | 7.1 |
| 84 |  | 3 | 0.64 (g) |  |  |  |  |
| 85 |  | 3 | 0.62 (g) |  |  |  |  |

-continued

| Comp | structure | S* | TLC Rf (x) | LCMS Rt | m.p. °C. | 5-HT$_6$ pA$_2$ | pK$_i$ |
|---|---|---|---|---|---|---|---|
| 86 | 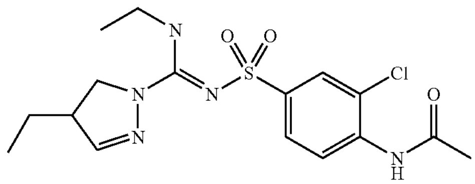 [SMILES: CCN/C(=N\S(=O)(=O)c1ccc(NC(C)=O)c(Cl)c1)N1CC(CC)C=N1] | 3 | 0.32 (g) | | | | |
| 87 | 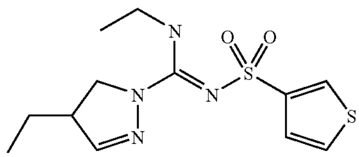 [SMILES: CCN/C(=N\S(=O)(=O)c1ccsc1)N1CC(CC)C=N1] | 3 | 0.45 (g) | | | | |
| 88 | 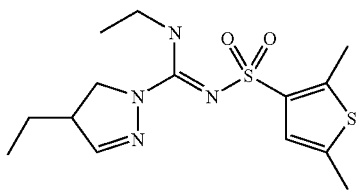 [SMILES: CCN/C(=N\S(=O)(=O)c1cc(C)sc1C)N1CC(CC)C=N1] | 3 | 0.48 (g) | | | | |
| 89 | 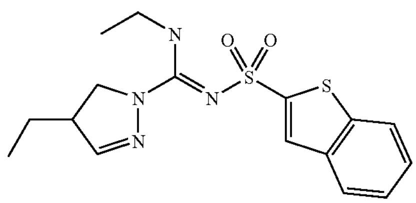 [SMILES: CCN/C(=N\S(=O)(=O)c1cc2ccccc2s1)N1CC(CC)C=N1] | 3 | 0.56 (g) | | | 9.1 | 8.3 |
| 90 | 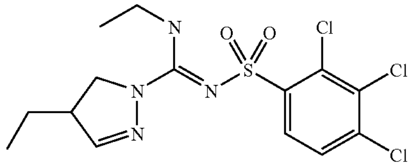 [SMILES: CCN/C(=N\S(=O)(=O)c1ccc(Cl)c(Cl)c1Cl)N1CC(CC)C=N1] | 3 | 0.62 (g) | | | | |
| 91 | 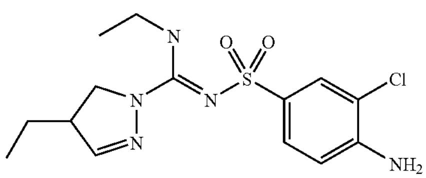 [SMILES: CCN/C(=N\S(=O)(=O)c1ccc(N)c(Cl)c1)N1CC(CC)C=N1] | 3 | 0.34 (g) 0.15 (j) | | | | |
| 92 | 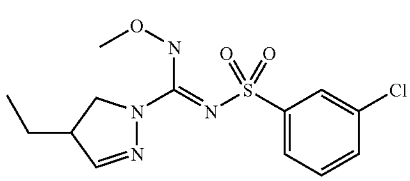 [SMILES: CCC1C=NN(/C(=N/S(=O)(=O)c2cccc(Cl)c2)NOC)C1] | 2 | | 1.99 | | | |
| 93 | 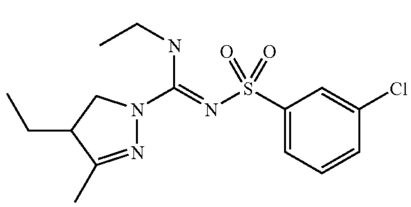 [SMILES: CCN/C(=N\S(=O)(=O)c1cccc(Cl)c1)N1CC(CC)C(C)=N1] | 2 | 0.20 (c) | 2.22 | | | |

-continued

| Comp | structure | S* | TLC Rf (x) | LCMS Rt | m.p. °C. | 5-HT6 pA2 | pKi |
|---|---|---|---|---|---|---|---|
| 94 | | 2 | 0.22 (c) | 2.06 | | | |
| 95 | | 2 | 0.19 (c) | 2.09 | | | |
| 96 | | 2 | 0.14 (c) | 1.79 | | | |
| 97 | | 2 | 0.19 (s) | | 146-147 | | |
| 98 | | 2 | 0.20 (t) | | | | |
| 99 | | 2 | 0.29 (a) | | | | |
| 100 | | 2 | 0.28 (a) | | | | |
| 101 | | 2 | | 1.72 | | | |

-continued

| Comp | structure | S* | TLC Rf (x) | LCMS Rt | m.p. °C. | 5-HT₆ pA₂ | pK$_i$ |
|---|---|---|---|---|---|---|---|
| 102 | | 2 | | 1.62 | 162-164 | | |
| 103 | | 2 | 0.15 (h) | 1.62 | | 7.3 | 7.1 |
| 104 | | 2 | 0.10 (h) | 1.62 | | | |
| 105 | | 2 | | 1.64 | 115-116 | | |
| 106 | | 2 | 0.43 (a) | | | | |
| 107 | | 2 | 0.50 (a) | | 184 | | |
| 108 | | 2 | | | | | |
| 109 | | 2 | 0.07 (h) | 1.65 | 155-156 | | |
| 110 | | 2 | | 1.66 | | | |

-continued

| Comp | structure | S* | TLC Rf (x) | LCMS Rt | m.p. °C. | 5-HT$_6$ pA$_2$ | pK$_i$ |
|---|---|---|---|---|---|---|---|
| 111 | | 2 | | 1.66 | | | |
| 112 | | 2 | | 1.79 | | 7.2 | 6.7 |
| 113 | | 2 | 0.16 (h) | 1.69 | 121-123 | | |
| 114 | | 2 | 0.27 (a) | | 139-141 | | |
| 115 | | 2 | | 1.65 | 135-137 | | |
| 116 | | 2 | 0.08 (c) | 1.64 | | | |
| 117 | | 2 | | 1.51 | 169-171 | | |
| 118 | | 2 | 0.09 (i) | 1.73 | | | |

-continued

| Comp | structure | S* | TLC Rf(x) | LCMS Rt | m.p. °C. | 5-HT$_6$ pA$_2$ | pK$_i$ |
|---|---|---|---|---|---|---|---|
| 119 | | 2 | 0.09 (j) | 1.44 | | | |
| 120 | | 2 | 0.15 (j) | 1.54 | | | |
| 121 | | 2 | 0.63 (a) | | 155-156 | | |
| 122 | | 2 | 0.10 (j) | | | | |
| (−)-122 | (−)-enantiomer −88° (1%, MeOH) | 2 | | 1.84 | | | |
| (+)122 | (+)-enantiomer +82° (1%, MeOH) | 2 | | 1.84 | | | |
| 123 | | 2 | 0.35 (a) | | | | |
| (−)-123 | (−)-enantiomer −93° (1%, DMSO) | 2 | | 1.58 | 176-178 | | |
| (+)123 | (+)-enantiomer +95° (1%, DMSO) | 2 | | 1.58 | 146-147 | | |
| 124 | | 2 | 0.55 (a) | | | | |

-continued

| Comp | structure | S* | TLC Rf (x) | LCMS Rt | m.p. ° C. | 5-HT₆ pA₂ | pK_i |
|---|---|---|---|---|---|---|---|
| 125 | | 2 | 0.43 (a) | | | | |
| 126 | | 2 | 0.25 (a) | | | | |
| 127 | | 2 | 0.35 (a) | | 198-199 | | |
| 128 | | 2 | 0.10 (j) | | | | |
| 129 | | 2 | 0.15 (j) | | | | |
| 130 | | 2 | 0.15 (j) | | 139-140 | 8.2 | 7.1 |
| 131 | | 2 | 0.35 (o) | | 174-177 | | |
| 132 | | 2 | 0.20 (j) | | | | |

-continued

| Comp | structure | S* | TLC Rf (x) | LCMS Rt | m.p. °C. | 5-HT$_6$ pA$_2$ | pK$_i$ |
|---|---|---|---|---|---|---|---|
| 133 | | 2 | 0.30 (j) | | 146-147 | 9.8 | 8.8 |
| 134 | | 3 | 0.17 (a) | | 122-125 | | |
| 135 | | 1 | | | 188-189 | | |
| 136 | | 1 | | | 179-184 | | |
| 137 | | 1 | | | 149-150 | | |

-continued

| Comp | structure | S* | TLC Rf (x) | LCMS Rt | m.p. °C. | 5-HT$_6$ pA$_2$ | pK$_i$ |
|---|---|---|---|---|---|---|---|
| 138 | | 2 | | 1.86 | 138-140 | | 6.2 |
| 139 | | 2 | 0.40 (c) | 2.09 | | 6.5 | 6.6 |
| 140 | | 2 | 0.18 (e) | 2.27 | | | 6.7 |
| 141 | | 2 | | 2.13 | 165-166 | | 6.8 |
| 142 | | 2 | | 1.76 | 164-166 | 7.3 | |
| 143 | | 2 | | 1.72 | 124-126 | 7.7 | 7.7 |
| (−)-143 | (−)-enantiomer −37° (1% in CHCl$_3$) | 2 | | 1.72 | | 8.1 | 8.1 |
| (+)143 | (+)-enantiomer −38° (1%, CHCl$_3$) | 2 | | 1.72 | | | 6.3 |

-continued

| Comp | structure | S* | TLC Rf (x) | LCMS Rt | m.p. °C. | 5-HT$_6$ pA$_2$ | pK$_i$ |
|---|---|---|---|---|---|---|---|
| 144 | | 2 | 0.16 (c) | 1.74 | | 8.1 | 8.1 |
| 145 | | 2 | 0.15 (g) | 1.38 | | 7.9 | 7.5 |
| 146 | | 2 | 0.17 (c) | 1.76 | | 7.4 | 7.7 |
| 147 | | 2 | 0.42 (g) | 1.58 | | 6.1 | 6.5 |
| 148 | | 2 | 0.17 (g) | 1.42 | | 6.9 | 6.3 |
| 149 | | 2 | 0.28 (e) | 1.81 | | 7.5 | 7.9 |
| 150 | | 2 | 0.30 (e) | 1.83 | | 7.5 | 7.5 |

-continued

| Comp | structure | S* | TLC Rf (x) | LCMS Rt | m.p. °C. | 5-HT₆ pA₂ | pK$_i$ |
|---|---|---|---|---|---|---|---|
| 151 | | 2 | 0.28 (c) | 2.17 | | 6.3 | 6.7 |
| 152 | | 2 | 0.30 & 0.40 (e) | 1.91 | | | 6.8 |
| cis(−)-152 | cis (−)-enantiomer −137° (1%, MeOH) | 2 | | | 129-132 | | |
| cis(+)-152 | cis (+)-enantiomer +166° (1%, MeOH) | 2 | | | 132-134 | | |
| trans-(−)-152 | trans (−)-enantiomer −96° (1%, MeOH) | 2 | | | 146-149 | | |
| trans-(+)-152 | trans (+)-enantiomer +72° (1%, MeOH) | 2 | | | 134-139 | | |
| 153 | | 2 | 0.14 & 0.20 (c) | 2.02 | | | 6.8 |
| cis(−)-153 | cis (−)-enantiomer −125° (1%, MeOH) | 2 | | | | | 7.3 |
| cis(+)-153 | cis (+)-enantiomer +127° (1%, MeOH) | 2 | | | | | 5.9 |
| trans-(−)-153 | trans (−)-enantiomer −106° (1%, CHCl₃) | 2 | | | | | 6.4 |
| trans-(+)-153 | trans (+)-enantiomer +117° (1%, CHCl₃) | 2 | | | | | 6.9 |
| 154 | | 2 | 0.07 (g) | 1.27 | | 8.4 | 8.0 |
| 155 | | 2 | 0.25 (g) | 1.54 | | | |

-continued

| Comp | structure | S* | TLC Rf (x) | LCMS Rt | m.p. °C. | 5-HT$_6$ pA$_2$ | pK$_i$ |
|---|---|---|---|---|---|---|---|
| 156 | | 2 | 0.63 (v) | 1.35 | | 8.7 | 8.5 |
| 157 | | 2 | 0.23 (w) | 1.35 | | 8.1 | 8.2 |
| 158 | | 2 | 0.09 (l) | 2.26 | | | |
| 159 | | 2 | 0.29 (o) | | 108-110 | 8.0 | 7.2 |
| 160 | | 2 | 0.28 (o) | | | 6.7 | 7.1 |
| 161 | | 2 | 0.15 (a) | | | 7.0 | 7.1 |
| 162 | | 2 | 0.23 (o) | | | 7.9 | 7.2 |
| 163 | | 2 | 0.32 (o) | | | 8.0 | 6.6 |

-continued

| Comp | structure | S* | TLC Rf (x) | LCMS Rt | m.p. °C. | 5-HT6 pA2 | pKi |
|---|---|---|---|---|---|---|---|
| 164 | | 2 | 0.15 (o) | | | 7.4 | 7.3 |
| 165 | | 2 | 0.21 (x) | | | 7.7 | 7.6 |
| 166 | | 2 | 0.14 (y) | | | 7.1 | 7.0 |
| 167 | | 2 | 0.14 (a) | | | 7.5 | 7.2 |
| 168 | | 2 | | 1.93 | | | 6.5 |
| 169 | | 2 | | 1.85 | | | |
| 170 | | 2 | 0.20 (z) | | | | |
| 171 | | 2 | | 1.31 | 60-61 | | |

-continued

| Comp | structure | S* | TLC Rf (x) | LCMS Rt | m.p. °C. | pA₂ | pK$_i$ |
|---|---|---|---|---|---|---|---|
| 172 | | 2 | | 1.67 | | | 6.5 |
| 173 | | 2 | | 1.60 | | | |
| 174 | | 2 | | 1.63 | | | 7.0 |
| 175 | | 3 | 0.18 (d) | 1.72 | | | 6.8 |
| 176 | | 3 | 0.19 (d) | 1.76 | | | |
| 177 | | 3 | | 1.87 | | | |
| 178 | | 3 | | 1.88 | | | |
| 179 | | 3 | | 1.23 | | | |

Physico-chemical prop. / pharmacology 5-HT₆

-continued

| Comp | structure | S* | TLC Rf(x) | LCMS Rt | m.p. °C | 5-HT₆ pA₂ | pK$_i$ |
|---|---|---|---|---|---|---|---|
| 180 | | 3 | | 1.43 | | | |
| 181 | | 3 | | 1.52 | | | |
| 182 | | 3 | | 1.32 | | | |
| 183 | | 3 | | 1.06 | | | |
| 184 | | 3 | | 1.53 | | | |
| 185 | | 3 | | 1.33 | | | |
| 186 | | 3 | | 1.49 | | | |

-continued

| Comp | structure | S* | TLC Rf(x) | LCMS Rt | m.p. °C. | 5-HT6 pA2 | pKi |
|---|---|---|---|---|---|---|---|
| 187 | | 3 | | 1.47 | | | |
| 188 | | 3 | | 1.34 | | | |
| 189 | | 3 | | 1.37 | | | |
| 190 | | 3 | | 1.29 | | | |
| 191 | | 3 | | 1.51 | | | |
| 192 | | 3 | | 1.21 | | | |
| 193 | | 3 | | 1.18 | | | |

| Comp | structure | S* | TLC Rf (x) | LCMS Rt | m.p. °C | 5-HT$_6$ pA$_2$ | pK$_i$ |
|---|---|---|---|---|---|---|---|
| 194 | | 3 | | 1.34 | | | |
| 195 | | 3 | | 1.29 | | | |
| 196 | | 3 | | 1.27 | | | |
| 197 | | 3 | | 1.66 | | | |
| 198 | | 3 | | 1.25 | | | |
| 199 | | 3 | | 1.41 | | | |
| 200 | | 3 | | 1.25 | | | |

-continued

| Comp | structure | TLC S* | Rf(x) | LCMS Rt | m.p. °C. | 5-HT₆ pA₂ | pK$_i$ |
|---|---|---|---|---|---|---|---|
| 201 | | 3 | | 1.33 | | | |
| 202 | | 3 | | 1.38 | | | |
| 203 | | 3 | | 1.49 | | | |
| 204 | | 3 | | 1.22 | | | |
| 205 | | 3 | | 1.64 | | | |
| 206 | | 3 | | 1.33 | | | |
| 207 | | 3 | | 1.35 | | | |

-continued
| | | | Physico-chemical prop. | | | pharmacology | |
| | | | TLC | LCMS | | 5-HT$_6$ | |
| Comp | structure | S* | Rf (x) | Rt | m.p. °C. | pA$_2$ | pK$_i$ |
| 208 | | | 3 | 1.25 | | | |
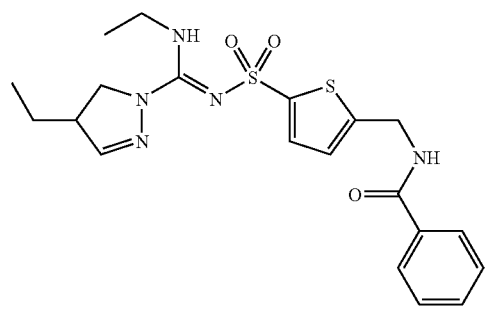 [SMILES: CCN/C(=N\S(=O)(=O)c1ccc(CNC(=O)c2ccccc2)s1)N1CC(CC)C=N1]
| 209 | | | 3 | 1.32 | | | |
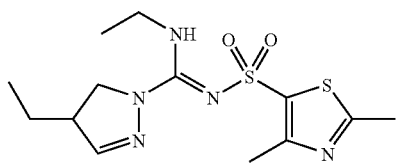 [SMILES: CCN/C(=N\S(=O)(=O)c1sc(C)nc1C)N1CC(CC)C=N1]
| 210 | | | 3 | 1.35 | | | |
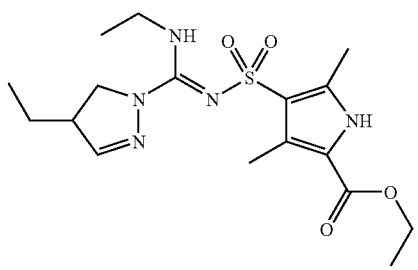 [SMILES: CCN/C(=N\S(=O)(=O)c1c(C)[nH]c(C(=O)OCC)c1C)N1CC(CC)C=N1]
| 211 | | | 3 | 1.64 | | | |
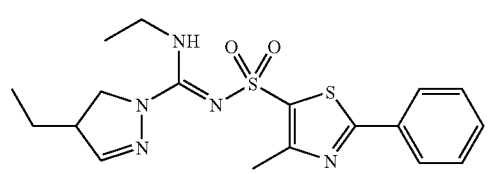 [SMILES: CCN/C(=N\S(=O)(=O)c1sc(-c2ccccc2)nc1C)N1CC(CC)C=N1]

| Comp | structure | S* | Physico-chemical prop. | | | pharmacology | |
| | | | TLC Rf (x) | LCMS Rt | m.p. °C. | 5-HT$_6$ pA$_2$ | pK$_i$ |
|---|---|---|---|---|---|---|---|
| 212 | | 3 | | 1.53 | | | |

S* = synthetic route; RF (x) = Rf-value, between brackets: TLC mobile phase:
(a) = diethylether;
(b) = MeOH:TEA = 97:3;
(c) = DCM:acetone = 99:1;
(d) = DCM:MeOH = 99:1;
(e) = DCM:acetone = 98:2;
(f) = DCM:acetone = 95:5;
(g) = DCM:MeOH = 98:2;
(h) = EA:PA = 1:2;
(i) = EA:PA = 1:3;
(j) = EA:PA = 1:1;
(k) = EA:PA = 1:4;
(l) = DCM;
(m) = DCM:MeOH = 97:3;
(n) = DCM:MeOH = 95:5;
(o) = EA;
(p) = EA:MeOH:NH$_4$OH = 94.5:5:0.5;
(q) = DCM:EA = 3:1;
(r) = DCM:dieethylether = 1:4;
(s) = dieethylether:PA = 7:3;
(t) = dieethylether:PA = 8:2;
(u) = EA:PA = 3:1;
(v) = DCM:MeOH:NH$_4$OH = 78:20:2;
(w) = DCM:MeOH:NH$_4$OH = 94.5:5:0.5;
(x) = Et$_2$O:EA = 8:2;
(y) = Et$_2$O:EA = 9:1;
(z) = EA:PA = 5:95;
Rt = retention time (in minutes) in LC-MS analysis The compounds of the invention are new. As indicated in the table above, they have a high affinity (pK$_i$) for 5-HT$_6$ receptors, and are potent antagonists (pA$_2$). Structurally the most closely related compounds disclosed in the literature are some of the sulfonylpyrrolidine derivatives disclosed in WO 02/030881:

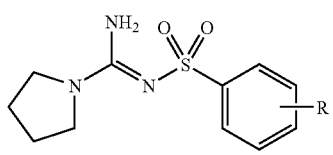

In WO 02/030881, for examples 18 (R=p-CH$_3$), 25 (R=p-Cl), 26 (R=H) and 27 (R=o-NO$_2$) no pharmacological data were given, but they are claimed to be modulators of gabapentin binding sites, useful in the therapy of a number of symptoms and disorders, including pain and migraine. These compounds are unlikely to have affinity for 5-HT$_6$ receptors, because during the synthetic explorations around the compounds of the present invention a series of compounds was synthesized with ring systems different from the pyrazoline ring (present in all compounds of the invention), and all of those were found to be inactive as 5-HT$_6$ antagonists. The closest to those disclosed in WO 02/030881 was:

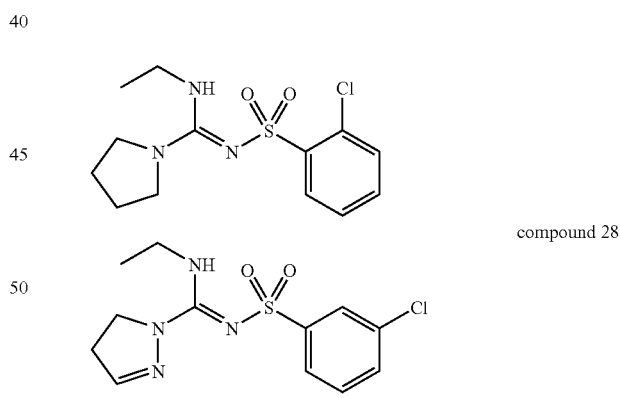

compound 28

This compound was found to be inactive (pA$_2$<5.0), in sharp contrast to compounds with pyrazoline rings (e.g. compound 28 has a pA$_2$-value of 7.7). Apart from the compound with the pyrrolidine ring, shown above, also compounds with exactly the same structure, but with different rings were synthesized (using routes similar to those disclosed above) and tested. Specifically: compounds with a phenyl, 2-pyridinyl, 2-pyrazinyl, 2-furanyl, 5-isoxazolyl, 2-quinolyl and 1-isoquinolyl ring (instead of the 1-pyrrolidine ring in the compound shown above) were all found to be inactive (pA$_2$<5.0), indicating that the pyrazoline ring of the compounds of the invention is important for interaction with 5-HT$_6$ receptors.

The specific compounds of which the synthesis is described above are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only.

EXAMPLE 5

Formulations Used in Animal Studies

For oral (p.o.) administration: to the desired quantity (0.5-5 mg) of the solid compound of general formula (1) in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (i.p.) administration: to the desired quantity (0.5-15 mg) of the solid compound of general formula (1) in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

EXAMPLE 6

Pharmacological Methods

In Vitro Affinity for Human 5-$HT_6$ Receptors

Affinity for human 5-$HT_6$ receptors was measured in a membrane preparation of CHO-cells transfected with human 5-$HT_6$ receptors by binding studies using [$^3$H]-N-Methyl-Lysergic acid diethylamide ([$^3$H]-LSD) as ligand. The membrane preparation was prepared from cells supplied by Euroscreen (Brussels). CHO/Gα16/mtAEQ/h5HT6-A1 cells were grown in T-flasks in CHO-S-SFM II medium (Gibco BRL), supplemented with 1% dialysed FCS, 2 mM L-glutamine, Geneticin 500 μg/ml and Zeocin 200 μg/ml. Cells were harvested using 0.25% Trypsin (1 ml/T175-flask), centrifuged and subsequently suspended in CHO-S-SFM II medium and frozen at −80° C. After thawing cells were centrifuged during 3 minutes at 1500 g at 4° C. From the pellet, cell membranes were prepared by two cycles of homogenization (Potter-Elvehjem 10 strokes, 600 rpm) and centrifugation (40,000 g for 15 min, 4° C.). The assay was established so as to achieve steady state conditions and to optimize specific binding. For the 5-$HT_6$ receptor, membranes from $5.10^5$ cells were incubated with 5.0 nM [$^3$H]-LSD at 37° C. for 30 minutes. Nonspecific binding was determined using $10^{-5}$ M serotonin. Assays were terminated by vacuum filtration through glass fiber filters (GF/B) which had been pretreated with 0.5% polyethyleneimine. Total and bound radioactivity was determined by liquid scintillation counting. Greater than 80% specific binding was achieved in each of these assays. Compounds were tested at a 4 log concentration range; all determinations were performed as triplicates. $IC_{50}$ values were determined by non-linear regression analysis using Hill equation curve fitting. The inhibition constants ($K_i$-values) were calculated from the Cheng-Preushoff equation:

$$K_i = IC_{50} : (1 + L/K_d)$$

wherein L represents the concentration radioligand ([$^3$H]-LSD) in the assay, and $K_d$ the affinity of the radioligand for the receptor. Results are expressed as $pK_i$-values, means±SD of at least three separate experiments.

In Vitro Functional Activity ((Ant)Agonism) on Human 5-$HT_6$ Receptors

The CHO-human-5$HT_6$-Aeqorin assay was bought from Euroscreen, Brussels (Euroscreen, Technical dossier, Human recombinant serotonin 5-$HT_6$-A1 receptor, DNA clone and CHO AequoScreen™ recombinant cell line, catalog no: ES-316-A, February 2003). Human-5-$HT_6$-Aequorin cells express mitochondrial targeted apo-Aequorin. Cells have to be loaded with coelanterazine, in order to reconstitute active Aequorin. After binding of agonists to the human 5-$HT_6$ receptor the intracellular calcium concentration increases and binding of calcium to the apo-Aequorin/coelenterazine complex leads to an oxidation reaction of coelenterazine, which results in the production of apo-Aequorin, coelenteramide, $CO_2$ and light ($\lambda_{max}$ 469 nm). This luminescent response is dependent on the agonist concentration. Luminescence is measured using the MicroBeta Jet (Perkin Elmer). Agonistic effects of compounds are expressed as $pEC_{50}$. Antagonistic effects of compounds were determined as inhibition of $10^{-8}$ M α-methylserotonin induced luminescence and the $pA_2$ was calculated according to Cheng-Preushoff equation. Compounds were tested at a 5 log concentration range, and 3 independent experiments were performed in duplicate.

EXAMPLE 7

Pharmaceutical Preparations

For clinical use, compounds of formula (1) are formulated into a pharmaceutical compositions that are important and novel embodiments of the invention because they contain the compounds, more particularly specific compounds disclosed herein. Types of pharmaceutical compositions that may be used include, but are not limited to, tablets, chewable tablets, capsules (including microcapsules), solutions, parenteral solutions, ointments (creams and gels), suppositories, suspensions, and other types disclosed herein, or apparent to a person skilled in the art from the specification and general knowledge in the art. The active ingredient for instance, may also be in the form of an inclusion complex in cyclodextrins, their ethers or their esters. The compositions are used for oral, intravenous, subcutaneous, tracheal, bronchial, intranasal, pulmonary, transdermal, buccal, rectal, parenteral or other ways to administer. The pharmaceutical formulation contains at least one compound of formula (1) in admixture with a pharmaceutically acceptable adjuvant, diluent and/or carrier. The total amount of active ingredients suitably is in the range of from about 0.1% (w/w) to about 95% (w/w) of the formulation, suitably from 0.5% to 50% (w/w) or from 1% to 25% (w/w).

The compounds of the invention can be brought into forms suitable for administration by means of usual processes using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets. A tablet is prepared using the ingredients below:

| Ingredient | Quantity (mg/tablet) |
|---|---|
| COMPOUND No. 20 | 10 |
| Cellulose, microcrystalline | 200 |
| Silicon dioxide, fumed | 10 |
| Stearic acid | 10 |
| Total | 230 |

The components are blended and compressed to form tablets each weighing 230 mg.

The active ingredients may be separately premixed with the other non-active ingredients, before being mixed to form a formulation. The active ingredients may also be mixed with each other, before being mixed with the non-active ingredients to form a formulation.

Soft gelatin capsules may be prepared with capsules containing a mixture of the active ingredients of the invention, vegetable oil, fat, or other suitable vehicle for soft gelatin capsules. Hard gelatin capsules may contain granules of the active ingredients. Hard gelatin capsules may also contain the active ingredients together with solid powdered ingredients such as lactose, saccharose, sorbitol, mannitol, potato starch, corn starch, amylopectin, cellulose derivatives or gelatin. Hard gelatin capsules can be prepared using the following ingredients:

| Ingredient | Quantity (mg/capsule) |
|---|---|
| COMPOUND No. 20 | 10 |
| Starch, dried | 95 |
| Magnesium stearate | 14 |
| Total | 120 |

The above ingredients are mixed and filled into hard gelatin capsules in 120 mg quantities.

Dosage units for rectal administration may be prepared (i) in the form of suppositories that contain the active substance mixed with a neutral fat base; (ii) in the form of a gelatin rectal capsule that contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration. Suppositories, each containing 1 mg of active ingredient, may be made as follows:

| Ingredient | Quantity (mg/suppository) |
|---|---|
| COMPOUND No. 20 | 20 |
| Saturated fatty acid glycerides | 2,000 |
| Total | 2,020 |

The active ingredient is passed through a appropriately sized mesh sieve and suspended in the saturated fatty acid glycerides previously melted using the minimum heat necessary. The mixture is then poured into a suppository mold of normal 2 g capacity and allowed to cool.

Liquid preparations may be prepared in the form of syrups, elixirs, concentrated drops or suspensions, e.g. solutions or suspensions containing the active ingredients and the remainder consisting, for example, of sugar or sugar alcohols and a mixture of ethanol, water, glycerol, propylene glycol and polyethylene glycol. An intravenous formulation may be prepared as follows:

| Ingredient | Quantity |
|---|---|
| COMPOUND No. 20 | 1 g |
| Arlatone G ™ | 100 ml |
| EtOH | 100 ml |
| Water, sterile | 800 ml |

The compound is dissolved in the Arlatone G™, EtOH and water, and then the solution is slowly diluted with further water.

If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the present invention are formulations and 'kits of parts' comprising one or more containers filled with one or more of the ingredients of a pharmaceutical composition of the invention, for use in medical therapy. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. The use of formulations of the present invention in the manufacture of medicaments for use in treating a condition in which antagonism of $5\text{-HT}_6$ receptors is required or desired, and methods of medical treatment or comprising the administration of a therapeutically effective total amount of at least one compound of formula (1) to a patient suffering from, or susceptible to, a condition in which antagonism of $5\text{-HT}_6$ receptors is required or desired.

By way of example and not of limitation, several pharmaceutical compositions are given, comprising examples of active compounds for systemic use or topical application. Other compounds of the invention or combinations thereof, may be used in place of (or in addition to) said compounds. The concentration of the active ingredient may be varied over a wide range as discussed herein. The amounts and types of ingredients that may be included are well known in the art.

BIBLIOGRAPHY

Bentley, J. C. et al. J. Psychopharmacol. Suppl. A64, 255 (1997).
Bentley, J. C. et al. Br J Pharmacol. Suppl. 126, P66 (1999$^a$).
Bentley, J. C., et al. Br J Pharmacal 126(7): 1537-42 (1999$^b$).

Berge, S. M.: "*Pharmaceutical salts*", J. Pharmaceutical Science, 66, 1-19 (1977).
Bickel, M. H.,: "*The pharmacology and Biochemistry of N-oxides*", Pharmacological Reviews, 21(4), 325-355, (1969).
Bundgaard, H. (editor), "*Design of Prodrugs*", Elsevier, (1985).
Byrn et al., Pharmaceutical Research, 12(7), 945-954, (1995).
Dwyer & Mellor,: "*Chelating agents and Metal Chelates*", Academic Press, chapter 7, (1964).
Ettmayer, P. et al., "*Lessons learned from marketed and investigational prodrugs*", J. Med. Chem., 47, 2393-2404, (2004).
Järvinen, T. et al., "*Design and Pharmaceutical applications of prodrugs*", pages 733-796 in: S. C. Gad (editor): "*Drug Discovery Handbook*", John Wiley & Sons Inc., New Jersey, U.S.A., (2005).
King, F. D., (editor), page 215 in: "*Medicinal Chemistry: Principles and Practice*", (1994), ISBN 0-85186-494-5.
Kohen, R., et al. J Neurochem 66(1): 47-56 (1996).
Martin, E. W. (Editor), "*Remington: The Science and Practice of Pharmacy*", Mack Publishing Company, 19$^{th}$ Edition, Easton, Pa., Vol 2., Chapter 83, 1447-1462, (1995).
Rogers, D. C., et al. Br J Pharamcol 127(suppl.). 22P (1999).
Roth, B. L., et al. J Pharmacol Exp Ther. 268(3): 1403-10 (1994).
Ruat, M. et al. Biochem. Biophys. Res. Commun. 193: 268-276 (1993).
Sebben, M. et al. NeuroReport 5: 2553-2557 (1994).
Sibley, D. R. et al., Mol. Pharmacol., 43, 320-327 (1993).
Sleight, A. J., et al., Neurotransmission, 11, 1-5 (1995).
Sleight, A. J., et al., Serotonin ID Research Alert, 2(3), 115-8) (1997).
Sleight, A. J., et al. Br J Pharmacol 124(3): 556-62 (1998).
Stella, J., "*Prodrugs as therapeutics*", Expert Opin. Ther. Patents, 14(3), 277-280, (2004).
Woolley M. L. et al. Neuropharmacology 41: 210-219 (2001).
WO 01/070700 and WO 02/030881.

What is claimed is:
1. A compound of formula ($1^X$):

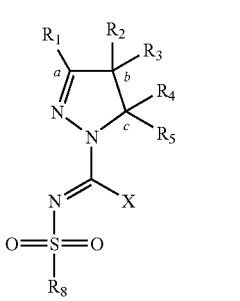

or a stereoisomer, N-oxide thereof, or pharmacologically acceptable salt of any of the foregoing, wherein:
X is chosen from halogen and S-alkyl($C_{1-4}$);
$R_1$ is chosen from hydrogen, an unsubstituted alkyl($C_{1-4}$) group, and an alkyl($C_{1-4}$) group substituted with one or more halogen atoms;
$R_2$ and $R_3$ independently are chosen from hydrogen, an unsubstituted alkyl($C_{1-4}$) group, an alkyl-($C_{1-4}$) group substituted with one or more halogen atoms, and a phenyl-alkoxy($C_{1-4}$)-alkyl($C_{1-4}$) group optionally substituted with one or more halogen atoms, or, $R_1$ and $R_2$, together with the carbon atoms marked 'a' and 'b' form a $C_{5-8}$-cycloalkyl ring, or
$R_2$ and $R_3$, together with the carbon atom marked 'b' form a $C_{3-8}$-cycloalkyl ring, or,
$R_2$ and $R_3$, together with the carbon atom marked 'b' form an $C_{5-8}$-heterocycloalkyl ring optionally substituted with one or more substituents Y, wherein Y is chosen from ($C_{1-3}$)alkyl, tri-fluoromethyl, fluoro, chloro, bromo, hydroxyl, ($C_{1-3}$)alkyloxy, trifluoromethoxy, and amino;
$R_4$ and $R_5$ independently are chosen from hydrogen, an unsubstituted alkyl($C_{1-4}$) group, an alkyl-($C_{1-4}$) group substituted with one or more halogen atoms, a monocyclic or a fused-bicyclic aromatic or hetero-aromatic group, optionally substituted with one or more substituents Y, as defined above, or,
$R_3$ and $R_4$, together with the carbon atoms marked 'b' and 'c' form a $C_{3-8}$-cycloalkyl ring, or,
$R_3$ and $R_4$, together with the carbon atoms marked 'b' and 'c' form a $C_{5-8}$-heterocycloalkyl ring, optionally substituted with one or more substituents Y, as defined above; and
$R_8$ is a monocyclic or a fused-bicyclic aromatic or hetero-aromatic group, optionally substituted with one or more substituents Y, as defined above, or,
$R_8$ is a —$CR_9$=$CR_{10}$-aryl group wherein $R_9$ and $R_{10}$ independently are chosen from hydrogen and an alkyl-($C_{1-3}$) group, and wherein aryl is chosen from a monocyclic, a fused bicyclic aromatic, and a hetero-aromatic group, or,
$R_8$ is chosen from a —C≡C-aryl group, wherein aryl is chosen from a monocyclic, a fused bicyclic aromatic, and a hetero-aromatic group, a piperidinyl group optionally substituted with one or more substituents Y, as defined above, and a —$NR_{11}R_{12}$ group, wherein $R_{11}$ and $R_{12}$ independently are chosen from hydrogen, an unsubstituted alkyl-($C_{1-3}$) group, and a phenyl or benzyl group, wherein the phenyl or benzyl group is optionally substituted with one or more substituents Y, as defined above.

2. A compound of formula ($1^Z$):

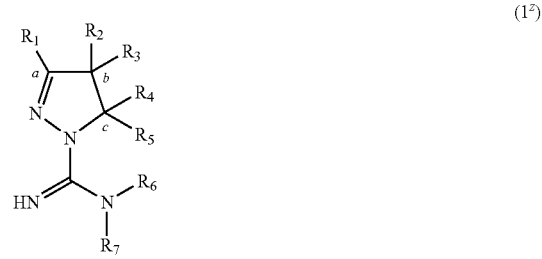

or a stereoisomer, N-oxide thereof, or pharmacologically acceptable salt of any of the foregoing, wherein:
$R_1$ is chosen from hydrogen, an unsubstituted alkyl($C_{1-4}$) group, and an alkyl($C_{1-4}$) group substituted with one or more halogen atoms;
$R_2$ and $R_3$ independently are chosen from hydrogen, an unsubstituted alkyl($C_{1-4}$) group, an alkyl-($C_{1-4}$) group substituted with one or more halogen atoms, and a phenyl-alkoxy($C_{1-4}$)-alkyl($C_{1-4}$) group optionally substituted with one or more halogen atoms, or,
$R_1$ and $R_2$, together with the carbon atoms marked 'a' and 'b' form a $C_{5-8}$-cycloalkyl ring, or $R_2$ and $R_3$, together with the carbon atom marked 'b' form a $C_{3-8}$-cycloalkyl ring, or, $R_2$ and $R_3$, together with the carbon atom marked 'b' form an $C_{5-8}$-heterocycloalkyl ring optionally substituted with one or more substituents Y, wherein Y is chosen from $(C_{1-3})$alkyl, tri-fluoromethyl, fluoro, chloro, bromo, hydroxyl, $(C_{1-3})$alkyloxy, trifluoromethoxy, and amino;

$R_4$ and $R_5$ independently are chosen from hydrogen, an unsubstituted alkyl$(C_{1-4})$ group, an alkyl-$(C_{1-4})$ group substituted with one or more halogen atoms, a monocyclic or a fused-bicyclic aromatic or hetero-aromatic group, optionally substituted with one or more substituents Y, as defined above, or, $R_3$ and $R_4$, together with the carbon atoms marked 'b' and 'c' form a $C_{3-8}$-cycloalkyl ring, or, $R_3$ and $R_4$, together with the carbon atoms marked 'b' and 'c' form a $C_{5-8}$-heterocycloalkyl ring, optionally substituted with one or more substituents Y, as defined above; and $R_6$ and $R_7$ independently are chosen from a hydrogen atom, an alkyl$(C_{1-4})$ group, an alkyl$(C_{1-4})$ group substituted with one or more halogen atoms, a $(C_{1-3})$alkoxy group, a dialkyl$(C_{1-3})$-amino-alkyl$(C_{1-3})$ group, a monocyclic or fused bicyclic aromatic or hetero-aromatic group, optionally substituted with one or more substitutents Y, as defined above, a $C_{5-8}$-cycloalkyl or a $C_{5-8}$-heterocycloalkyl group, optionally substituted with one or more substituents Y, as defined above, and a benzyl group, or $R_6$ and $R_7$, together with the nitrogen atom to which they are attached, form a $C_{5-8}$-hetero-cycloalkyl group, optionally substituted with one or more substituents Y, as defined above, with the proviso that when $R_2$, $R_3$, $R_6$, and $R_7$ are hydrogen, and $R_4$ or $R_5$ is phenyl optionally substituted with one or more substituents Y, as defined above, $R_1$ is not methyl, and with the proviso that $R_1$, $R_2$, $R_3$, $R_4$, $R_5$, $R_6$, and $R_7$, are not simultaneously all hydrogen atoms.

3. A process for preparing a compound of formula (1'), comprising:

(i) reacting a compound of formula (X), obtained by reacting a compound of formula (IX) with an alkyl halide, with a pyrazoline of formula

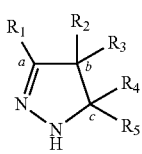

in the presence of a base, to yield a compound of formula ($1^Z$), and (ii) reacting a compound of formula ($1^Z$) with a sulfonyl halide of formula $R_8$—$SO_2$—X, wherein X is Br, Cl or F, in an aprotic solvent, in the presence of a base,

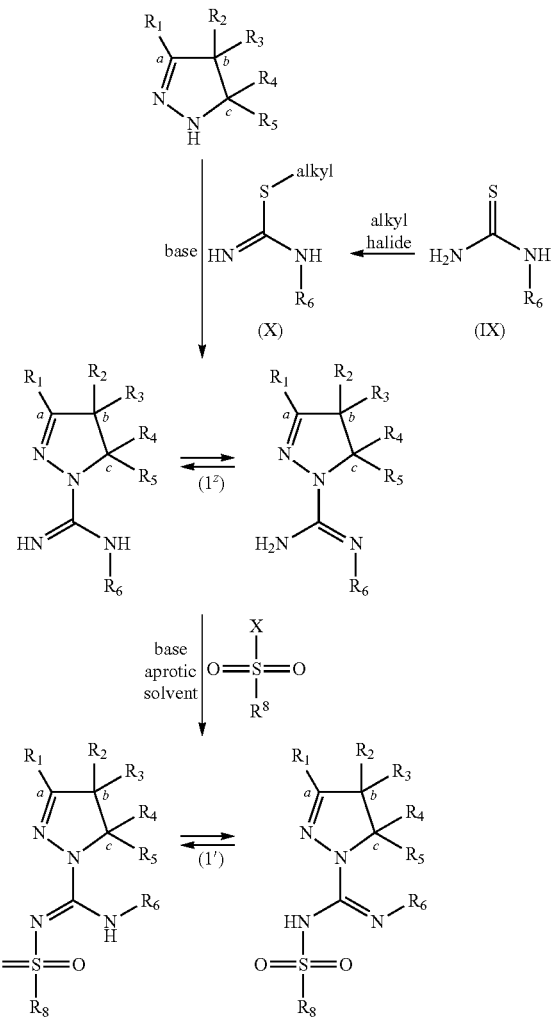

wherein:

$R_1$ is chosen from hydrogen, an unsubstituted alkyl$(C_{1-4})$ group, and an alkyl$(C_{1-4})$ group substituted with one or more halogen atoms;

$R_2$ and $R_3$ independently are chosen from hydrogen, an unsubstituted alkyl$(C_{1-4})$ group, an alkyl-$(C_{1-4})$ group substituted with one or more halogen atoms, and a phenyl-alkoxy$(C_{1-4}$-alkyl$(C_{1-4})$ group optionally substituted with one or more halogen atoms, or, $R_1$ and $R_2$, together with the carbon atoms marked 'a' and 'b' form a $C_{5-8}$-cycloalkyl ring, or $R_2$ and $R_3$, together with the carbon atom marked 'b' form a $C_{3-8}$-cycloalkyl ring, or, $R_2$ and $R_3$, together with the carbon atom marked 'b' form an $C_{5-8}$-heterocycloalkyl ring optionally substituted with one or more substituents Y, wherein Y is chosen from $(C_{1-3})$alkyl, tri-fluoromethyl, fluoro, chloro, bromo, hydroxyl, $(C_{1-3})$alkyloxy, trifluoromethoxy, and amino;

$R_4$ and $R_5$ independently are chosen from hydrogen, an unsubstituted alkyl$(C_{1-4})$ group, an alkyl-$(C_{1-4})$ group substituted with one or more halogen atoms, a monocyclic or a fused-bicyclic aromatic or hetero-aromatic group, optionally substituted with one or more substituents Y, as defined above, or, $R_3$ and $R_4$, together with the carbon atoms marked 'b' and 'c' form a $C_{3-8}$-cycloalkyl ring, or, $R_3$ and $R_4$, together with the carbon atoms marked 'b' and 'c' form a $C_{5-8}$-heterocycloalkyl ring, optionally substituted with one or more substituents Y, as defined above;

$R_6$ independently is chosen from a hydrogen atom, an alkyl($C_{1-4}$) group, an alkyl($C_{1-4}$) group substituted with one or more halogen atoms, a ($C_{1-3}$)alkoxy group, a dialkyl($C_{1-3}$)-amino-alkyl($C_{1-3}$) group, a monocyclic or fused bicyclic aromatic or hetero-aromatic group, optionally substituted with one or more substitutents Y, as defined above, a $C_{5-8}$-cycloalkyl or a $C_{5-8}$-heterocycloalkyl group, optionally substituted with one or more substituents Y, as defined above, and a benzyl group; and $R_8$ is a monocyclic or a fused-bicyclic aromatic or heteroaromatic group, optionally substituted with one or more substituents Y, as defined above, or, $R_8$ is a —$CR_9$=$CR_{10}$-aryl group wherein $R_9$ and $R_{10}$ independently are chosen from hydrogen and an alkyl-($C_{1-3}$) group, and wherein aryl is chosen from a monocyclic, a fused bicyclic aromatic, and a hetero-aromatic group, or, $R_8$ is chosen from a —C≡C-aryl group, wherein aryl is chosen from a monocyclic, a fused bicyclic aromatic, and a hetero-aromatic group, a piperidinyl group optionally substituted with one or more substituents Y, as defined above, and a —$NR_{11}R_{12}$ group, wherein $R_{11}$ and $R_{12}$ independently are chosen from hydrogen, an unsubstituted alkyl-($C_{1-3}$) group, and a phenyl or benzyl group, wherein the phenyl or benzyl group is optionally substituted with one or more substituents Y, as defined above.

* * * * *